US008454612B2

(12) United States Patent
Lambrecht et al.

(10) Patent No.: US 8,454,612 B2
(45) Date of Patent: Jun. 4, 2013

(54) METHOD FOR VERTEBRAL ENDPLATE RECONSTRUCTION

(75) Inventors: Gregory Lambrecht, Natick, MA (US); Thomas Boyajian, Wilmington, MA (US); Almir Velagic, Melrose, MA (US); Robert Kevin Moore, Natick, MA (US); Christopher Tarapata, North Andover, MA (US); Jacob Einhorn, Brookline, MA (US); Sean Kavanaugh, Eastham, MA (US)

(73) Assignee: Intrinsic Therapeutics, Inc., Woburn, MA (US)

(*) Notice: Subject to any disclaimer, the term of this patent is extended or adjusted under 35 U.S.C. 154(b) by 580 days.

(21) Appl. No.: 12/545,020

(22) Filed: Aug. 20, 2009

(65) Prior Publication Data
US 2010/0049259 A1    Feb. 25, 2010

Related U.S. Application Data

(63) Continuation of application No. 12/524,334, filed as application No. PCT/US2008/075496 on Sep. 5, 2008.

(60) Provisional application No. 60/967,782, filed on Sep. 7, 2007, provisional application No. 61/066,334, filed on Feb. 20, 2008, provisional application No. 61/066,700, filed on Feb. 22, 2008, provisional application No. 61/126,548, filed on May 5, 2008.

(51) Int. Cl.
*A61F 2/46* (2006.01)

(52) U.S. Cl.
USPC ........................................ 606/86 R

(58) Field of Classification Search
USPC ................... 606/86 R, 279, 246
See application file for complete search history.

(56) References Cited

U.S. PATENT DOCUMENTS

| 3,526,567 A | 9/1970 | Macone |
| 3,867,728 A | 2/1975 | Stubstad et al. |

(Continued)

FOREIGN PATENT DOCUMENTS

| EP | 0277678 | 8/1988 |
| EP | 0298233 | 1/1989 |

(Continued)

OTHER PUBLICATIONS

Cauthen, Joseph, Draft Abstract entitled *Microsurgical Annular Reconstruction (Annuloplasty) Following Lumbar Microdiscectomy: Preliminary Report of a New Technique*, from abstracts@neurosurgery.org, reportedly published in Feb. 1999 and dated Sep. 4, 1998, and contextual documents, 39 pages.

(Continued)

*Primary Examiner* — Kevin T Truong
*Assistant Examiner* — Sameh Boles
(74) *Attorney, Agent, or Firm* — Knobbe, Martens, Olson & Bear LLP

(57) ABSTRACT

Embodiments relate generally to tissue anchors and methods of delivering same to the intervertebral disc or other sites within the body. In some embodiments, the anchors provide increased pull-out resistance, stability and/or contact with tissue involving a reduced amount of penetration. In some embodiments, delivery methods are minimally invasive and can include linear, lateral, and off-angle implantation or driving of anchors along, against or within tissue surfaces. Several embodiments disclose anchors and anchoring systems that effectively reconstruct or augment vertebral endplate surfaces.

8 Claims, 76 Drawing Sheets

U.S. PATENT DOCUMENTS

| | | |
|---|---|---|
| 3,875,595 A | 4/1975 | Froning |
| 3,921,632 A | 11/1975 | Bardani |
| 3,997,138 A | 12/1976 | Crock et al. |
| 4,041,550 A | 8/1977 | Frazier |
| 4,078,559 A | 3/1978 | Nissinen |
| 4,280,954 A | 7/1981 | Yannas et al. |
| 4,349,921 A | 9/1982 | Kuntz |
| 4,365,357 A | 12/1982 | Draenert |
| 4,473,070 A | 9/1984 | Matthews et al. |
| 4,502,161 A | 3/1985 | Wall |
| 4,532,926 A | 8/1985 | O'Holla |
| 4,573,454 A | 3/1986 | Hoffman |
| 4,665,906 A | 5/1987 | Jervis |
| 4,738,251 A | 4/1988 | Plaza |
| 4,741,330 A | 5/1988 | Hayhurst |
| 4,743,256 A | 5/1988 | Brantigan |
| 4,744,364 A | 5/1988 | Kensey |
| 4,755,184 A | 7/1988 | Silverberg |
| 4,772,287 A | 9/1988 | Ray et al. |
| 4,781,190 A | 11/1988 | Lee |
| 4,798,205 A | 1/1989 | Bonomo et al. |
| 4,815,453 A | 3/1989 | Cotrel |
| 4,821,942 A | 4/1989 | Richards et al. |
| 4,837,285 A | 6/1989 | Berg et al. |
| 4,852,568 A | 8/1989 | Kensey |
| 4,854,304 A | 8/1989 | Zielke |
| 4,863,477 A | 9/1989 | Monson |
| 4,871,094 A | 10/1989 | Gall et al. |
| 4,873,976 A | 10/1989 | Schreiber |
| 4,874,389 A | 10/1989 | Downey |
| 4,890,612 A | 1/1990 | Kensey |
| 4,904,260 A | 2/1990 | Ray et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,936,844 A | 6/1990 | Chandler et al. |
| 4,946,378 A | 8/1990 | Hirayama et al. |
| 4,946,467 A | 8/1990 | Ohi et al. |
| 4,955,908 A | 9/1990 | Frey et al. |
| 4,994,073 A | 2/1991 | Green et al. |
| 5,002,576 A | 3/1991 | Fuhrmann et al. |
| 5,007,909 A | 4/1991 | Rogozinski |
| 5,015,255 A | 5/1991 | Kuslich |
| 5,021,059 A | 6/1991 | Kensey et al. |
| 5,035,716 A | 7/1991 | Downey |
| 5,046,513 A | 9/1991 | Gatturna et al. |
| 5,047,055 A | 9/1991 | Bao et al. |
| 5,053,046 A | 10/1991 | Janese |
| 5,059,206 A | 10/1991 | Winters |
| 5,061,274 A | 10/1991 | Kensey |
| 5,071,437 A | 12/1991 | Steffee |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,155 A | 6/1992 | Eberbach |
| 5,123,926 A | 6/1992 | Pisharodi |
| 5,129,906 A | 7/1992 | Ross et al. |
| 5,141,515 A | 8/1992 | Eberbach |
| 5,147,374 A | 9/1992 | Fernandez |
| 5,147,387 A | 9/1992 | Jansen et al. |
| 5,171,252 A | 12/1992 | Friedland |
| 5,171,259 A | 12/1992 | Inoue |
| 5,171,279 A | 12/1992 | Mathews |
| 5,171,280 A | 12/1992 | Baumgartner |
| 5,171,281 A | 12/1992 | Parsons et al. |
| 5,176,692 A | 1/1993 | Wilk et al. |
| 5,180,393 A | 1/1993 | Commarmond |
| 5,189,789 A | 3/1993 | Hall |
| 5,192,300 A | 3/1993 | Fowler |
| 5,192,301 A | 3/1993 | Kamiya et al. |
| 5,192,326 A | 3/1993 | Bao et al. |
| 5,201,729 A | 4/1993 | Hertzmann et al. |
| 5,203,787 A | 4/1993 | Noblitt et al. |
| 5,207,649 A | 5/1993 | Aruny |
| 5,217,471 A | 6/1993 | Burkhart |
| 5,219,359 A | 6/1993 | McQuilkin et al. |
| 5,222,962 A | 6/1993 | Burkhart |
| 5,222,974 A | 6/1993 | Kensey et al. |
| 5,236,438 A | 8/1993 | Wilk |
| 5,239,982 A | 8/1993 | Trauthen |
| 5,242,448 A | 9/1993 | Pettine et al. |
| 5,254,133 A | 10/1993 | Seid |
| 5,258,000 A | 11/1993 | Gianturco |
| 5,258,031 A | 11/1993 | Salib et al. |
| 5,258,043 A | 11/1993 | Stone |
| 5,269,783 A | 12/1993 | Sander |
| 5,282,827 A | 2/1994 | Kensey et al. |
| 5,292,332 A | 3/1994 | Lee |
| 5,306,311 A | 4/1994 | Stone et al. |
| 5,312,435 A | 5/1994 | Nash et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,352,224 A | 10/1994 | Westermann |
| 5,356,432 A | 10/1994 | Rutkow et al. |
| 5,366,460 A | 11/1994 | Eberbach |
| 5,368,602 A | 11/1994 | de la Torre |
| 5,370,697 A | 12/1994 | Baumgartner |
| 5,383,477 A | 1/1995 | DeMatteis |
| 5,383,905 A | 1/1995 | Golds et al. |
| 5,387,213 A | 2/1995 | Breard et al. |
| 5,391,182 A | 2/1995 | Chin |
| 5,397,331 A | 3/1995 | Himpens et al. |
| 5,397,332 A | 3/1995 | Kammerer et al. |
| 5,397,355 A | 3/1995 | Marin et al. |
| 5,405,360 A | 4/1995 | Tovey |
| 5,425,773 A | 6/1995 | Boyd et al. |
| 5,431,658 A | 7/1995 | Moskovich |
| 5,437,631 A | 8/1995 | Janzen |
| 5,445,639 A | 8/1995 | Kuslich et al. |
| 5,456,720 A | 10/1995 | Schultz et al. |
| 5,464,407 A | 11/1995 | McGuire |
| 5,478,353 A | 12/1995 | Yoon |
| 5,500,000 A | 3/1996 | Feagin et al. |
| 5,507,754 A | 4/1996 | Green et al. |
| 5,514,130 A | 5/1996 | Baker |
| 5,514,180 A | 5/1996 | Heggeness et al. |
| 5,520,700 A | 5/1996 | Beyar et al. |
| 5,522,898 A | 6/1996 | Bao et al. |
| 5,531,759 A | 7/1996 | Kensey et al. |
| 5,534,028 A | 7/1996 | Bao et al. |
| 5,534,030 A | 7/1996 | Navarro et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,552,100 A | 9/1996 | Shannon et al. |
| 5,556,428 A | 9/1996 | Shah |
| 5,556,429 A | 9/1996 | Felt |
| 5,562,689 A | 10/1996 | Green et al. |
| 5,562,735 A | 10/1996 | Margulies |
| 5,562,736 A | 10/1996 | Ray et al. |
| 5,562,738 A | 10/1996 | Boyd et al. |
| 5,569,252 A | 10/1996 | Justin et al. |
| 5,571,189 A | 11/1996 | Kuslich |
| 5,582,616 A | 12/1996 | Bolduc et al. |
| 5,591,204 A | 1/1997 | Jansen et al. |
| 5,591,223 A | 1/1997 | Lock et al. |
| 5,591,235 A | 1/1997 | Kuslich |
| 5,609,634 A | 3/1997 | Voydeville |
| 5,611,801 A | 3/1997 | Songer |
| 5,613,974 A | 3/1997 | Andreas et al. |
| 5,620,012 A | 4/1997 | Benderev et al. |
| 5,624,463 A | 4/1997 | Stone et al. |
| 5,626,613 A | 5/1997 | Schmieding |
| 5,634,931 A | 6/1997 | Kugel |
| 5,634,936 A | 6/1997 | Linden et al. |
| 5,641,373 A | 6/1997 | Shannon et al. |
| 5,645,084 A | 7/1997 | McKay |
| 5,645,597 A | 7/1997 | Krapiva |
| 5,649,926 A | 7/1997 | Howland |
| 5,658,286 A | 8/1997 | Sava |
| 5,658,343 A | 8/1997 | Hauselmann et al. |
| 5,662,683 A | 9/1997 | Kay |

| | | | | | |
|---|---|---|---|---|---|
| 5,669,935 A | 9/1997 | Rosenman et al. | 5,976,192 A | 11/1999 | McIntyre et al. |
| 5,674,294 A | 10/1997 | Bainville et al. | 5,980,504 A | 11/1999 | Sharkey et al. |
| 5,674,295 A | 10/1997 | Ray et al. | 5,989,256 A | 11/1999 | Kuslich et al. |
| 5,674,296 A | 10/1997 | Bryan et al. | 5,993,448 A | 11/1999 | Remmler |
| 5,676,698 A | 10/1997 | Janzen et al. | 6,001,056 A | 12/1999 | Jassawalla et al. |
| 5,676,701 A | 10/1997 | Yuan et al. | 6,001,130 A | 12/1999 | Bryan et al. |
| 5,681,310 A | 10/1997 | Yuan et al. | 6,007,570 A | 12/1999 | Sharkey et al. |
| 5,681,351 A | 10/1997 | Jamiolkowski et al. | 6,007,575 A | 12/1999 | Samuels |
| 5,683,465 A | 11/1997 | Shinn et al. | 6,017,346 A | 1/2000 | Grotz |
| 5,690,674 A | 11/1997 | Diaz | 6,019,792 A | 2/2000 | Cauthen |
| 5,695,525 A | 12/1997 | Mulhauser et al. | 6,019,793 A | 2/2000 | Perren et al. |
| 5,702,450 A | 12/1997 | Bisserie | 6,024,096 A | 2/2000 | Buckberg |
| 5,702,451 A | 12/1997 | Biedermann et al. | 6,027,527 A | 2/2000 | Asano et al. |
| 5,702,454 A | 12/1997 | Baumgartner | 6,066,175 A | 5/2000 | Henderson et al. |
| 5,702,462 A | 12/1997 | Oberlander | 6,073,051 A | 6/2000 | Sharkey et al. |
| 5,704,936 A | 1/1998 | Mazel | 6,093,205 A | 7/2000 | McLeod et al. |
| 5,705,780 A | 1/1998 | Bao | 6,093,207 A | 7/2000 | Pisharodi |
| 5,716,408 A | 2/1998 | Eldridge et al. | 6,096,044 A | 8/2000 | Boyd et al. |
| 5,716,409 A | 2/1998 | Debbas | 6,099,791 A | 8/2000 | Shannon et al. |
| 5,716,413 A | 2/1998 | Walter et al. | 6,102,930 A | 8/2000 | Simmons, Jr. |
| 5,716,416 A | 2/1998 | Lin | 6,105,581 A | 8/2000 | Eggers et al. |
| 5,725,577 A | 3/1998 | Saxon | 6,110,210 A | 8/2000 | Norton et al. |
| 5,725,582 A | 3/1998 | Bevan et al. | 6,113,639 A | 9/2000 | Ray et al. |
| 5,728,097 A | 3/1998 | Mathews | 6,120,503 A | 9/2000 | Michelson |
| 5,728,150 A | 3/1998 | McDonald et al. | 6,120,539 A | 9/2000 | Eldridge et al. |
| 5,730,744 A | 3/1998 | Justin et al. | 6,124,523 A | 9/2000 | Banas et al. |
| 5,733,337 A | 3/1998 | Carr, Jr. et al. | 6,126,682 A | 10/2000 | Sharkey et al. |
| 5,743,917 A | 4/1998 | Saxon | 6,132,465 A | 10/2000 | Ray et al. |
| 5,746,755 A | 5/1998 | Wood et al. | 6,140,452 A | 10/2000 | Felt et al. |
| 5,746,765 A | 5/1998 | Kleshinski et al. | 6,146,380 A | 11/2000 | Racz et al. |
| 5,755,797 A | 5/1998 | Baumgartner | 6,146,420 A | 11/2000 | McKay |
| 5,766,246 A | 6/1998 | Mulhauser et al. | 6,153,292 A | 11/2000 | Bell et al. |
| 5,769,864 A | 6/1998 | Kugel | 6,156,067 A | 12/2000 | Bryan et al. |
| 5,769,893 A | 6/1998 | Shah | 6,174,311 B1 | 1/2001 | Branch et al. |
| 5,772,661 A | 6/1998 | Michelson | 6,174,323 B1 | 1/2001 | Biggs et al. |
| 5,776,183 A | 7/1998 | Kanesaka et al. | 6,179,836 B1 | 1/2001 | Eggers et al. |
| 5,782,831 A | 7/1998 | Sherman et al. | 6,180,848 B1 | 1/2001 | Flament et al. |
| 5,782,844 A | 7/1998 | Yoon et al. | 6,183,518 B1 | 2/2001 | Ross et al. |
| 5,785,705 A | 7/1998 | Baker | 6,187,048 B1 | 2/2001 | Milner et al. |
| 5,800,549 A | 9/1998 | Bao et al. | 6,190,353 B1 | 2/2001 | Makower et al. |
| 5,800,550 A | 9/1998 | Sertich | 6,190,414 B1 | 2/2001 | Young et al. |
| 5,810,851 A | 9/1998 | Yoon | 6,203,735 B1 | 3/2001 | Edwin et al. |
| 5,823,994 A | 10/1998 | Sharkey et al. | 6,206,921 B1 | 3/2001 | Guagliano et al. |
| 5,824,008 A | 10/1998 | Bolduc et al. | 6,214,039 B1 | 4/2001 | Banas et al. |
| 5,824,082 A | 10/1998 | Brown | 6,224,630 B1 | 5/2001 | Bao et al. |
| 5,824,093 A | 10/1998 | Ray et al. | 6,224,631 B1 | 5/2001 | Kohrs et al. |
| 5,824,094 A | 10/1998 | Serhan et al. | 6,231,597 B1 | 5/2001 | Deem et al. |
| 5,827,298 A | 10/1998 | Hart et al. | 6,235,059 B1 | 5/2001 | Benezech et al. |
| 5,836,315 A | 11/1998 | Benderev et al. | 6,240,926 B1 | 6/2001 | Chin Gan et al. |
| 5,843,082 A | 12/1998 | Yuan et al. | 6,241,722 B1 | 6/2001 | Dobak et al. |
| 5,843,084 A | 12/1998 | Hart et al. | 6,245,099 B1 | 6/2001 | Edwin et al. |
| 5,843,173 A | 12/1998 | Shannon et al. | 6,245,107 B1 | 6/2001 | Ferree |
| 5,846,261 A | 12/1998 | Kotula et al. | 6,248,106 B1 | 6/2001 | Ferree |
| 5,860,425 A | 1/1999 | Benderev et al. | 6,258,086 B1 | 7/2001 | Ashley et al. |
| 5,860,977 A | 1/1999 | Zucherman et al. | 6,264,659 B1 | 7/2001 | Ross et al. |
| 5,865,845 A | 2/1999 | Thalgott | 6,264,695 B1 | 7/2001 | Stoy |
| 5,865,846 A | 2/1999 | Bryan et al. | 6,267,834 B1 | 7/2001 | Shannon et al. |
| 5,888,220 A | 3/1999 | Felt et al. | 6,273,912 B1 | 8/2001 | Scholz et al. |
| 5,888,226 A | 3/1999 | Rogozinski | 6,280,475 B1 | 8/2001 | Bao et al. |
| 5,893,889 A | 4/1999 | Harrington | 6,299,613 B1 | 10/2001 | Ogilvie et al. |
| 5,895,426 A | 4/1999 | Scarborough et al. | 6,312,462 B1 | 11/2001 | McDermott et al. |
| 5,911,701 A | 6/1999 | Miller et al. | RE37,479 E | 12/2001 | Kuslich |
| 5,916,225 A | 6/1999 | Kugel | 6,325,805 B1 | 12/2001 | Ogilvie et al. |
| 5,919,235 A | 7/1999 | Husson et al. | 6,340,369 B1 | 1/2002 | Ferree |
| 5,922,026 A | 7/1999 | Chin | 6,344,058 B1 | 2/2002 | Ferree et al. |
| 5,922,028 A | 7/1999 | Plouhar et al. | 6,352,557 B1 | 3/2002 | Ferree et al. |
| 5,928,279 A | 7/1999 | Shannon et al. | 6,355,063 B1 | 3/2002 | Calcote |
| 5,928,284 A | 7/1999 | Mehdizadeh | 6,364,908 B1 | 4/2002 | Ysebaert |
| 5,935,147 A | 8/1999 | Kensey et al. | 6,371,990 B1 * | 4/2002 | Ferree ........................ 623/17.16 |
| 5,947,968 A | 9/1999 | Rogozinski | 6,383,214 B1 | 5/2002 | Banas et al. |
| 5,954,716 A | 9/1999 | Sharkey et al. | 6,387,130 B1 | 5/2002 | Stone et al. |
| 5,954,767 A | 9/1999 | Pajotin et al. | 6,395,033 B1 | 5/2002 | Pepper |
| 5,957,939 A | 9/1999 | Heaven et al. | 6,398,803 B1 | 6/2002 | Layne et al. |
| 5,961,545 A | 10/1999 | Lentz et al. | 6,402,680 B2 | 6/2002 | Mortier et al. |
| 5,972,000 A | 10/1999 | Beyar et al. | 6,402,750 B1 | 6/2002 | Atkinson et al. |
| 5,972,007 A | 10/1999 | Sheffield et al. | 6,406,420 B1 | 6/2002 | McCarthy et al. |
| 5,972,022 A | 10/1999 | Huxel | 6,416,537 B1 | 7/2002 | Martakos et al. |
| 5,976,174 A | 11/1999 | Ruiz | 6,419,702 B1 | 7/2002 | Ferree |
| 5,976,186 A | 11/1999 | Bao et al. | 6,419,704 B1 | 7/2002 | Ferree |

| | | |
|---|---|---|
| 6,425,900 B1 | 7/2002 | Knodel et al. |
| 6,425,919 B1 | 7/2002 | Lambrecht et al. |
| 6,425,924 B1 | 7/2002 | Rousseau |
| 6,428,575 B2 | 8/2002 | Koo et al. |
| 6,428,576 B1 | 8/2002 | Haldimann |
| 6,436,143 B1 | 8/2002 | Ross et al. |
| 6,443,988 B2 | 9/2002 | Felt et al. |
| 6,454,804 B1 | 9/2002 | Ferree |
| 6,458,131 B1 | 10/2002 | Ray |
| 6,482,235 B1 | 11/2002 | Lambrecht et al. |
| 6,491,690 B1 | 12/2002 | Goble et al. |
| 6,503,269 B2 | 1/2003 | Neild et al. |
| 6,508,828 B1 | 1/2003 | Akerfeldt et al. |
| 6,508,839 B1 | 1/2003 | Lambrecht et al. |
| 6,514,194 B2 | 2/2003 | Schweich et al. |
| 6,520,967 B1 | 2/2003 | Cauthen |
| 6,530,932 B1 | 3/2003 | Swayze et al. |
| 6,530,933 B1 | 3/2003 | Yeung et al. |
| 6,537,198 B1 | 3/2003 | Vidlund et al. |
| 6,551,320 B2 | 4/2003 | Lieberman |
| 6,551,356 B2 | 4/2003 | Rousseau |
| 6,558,387 B2 | 5/2003 | Errico et al. |
| 6,576,017 B2 | 6/2003 | Foley et al. |
| 6,579,291 B1 | 6/2003 | Keith et al. |
| 6,582,433 B2 | 6/2003 | Yun |
| 6,589,160 B2 | 7/2003 | Schweich et al. |
| 6,592,625 B2 | 7/2003 | Cauthen |
| 6,599,311 B1 | 7/2003 | Biggs et al. |
| 6,607,530 B1 | 8/2003 | Carl et al. |
| 6,610,094 B2 | 8/2003 | Husson |
| 6,613,074 B1 | 9/2003 | Mitelberg et al. |
| 6,616,669 B2 | 9/2003 | Ogilvie et al. |
| 6,616,684 B1 | 9/2003 | Vidlund et al. |
| 6,620,196 B1 | 9/2003 | Trieu |
| 6,626,909 B2 | 9/2003 | Chin |
| 6,626,916 B1 | 9/2003 | Yeung et al. |
| 6,645,211 B2 | 11/2003 | Magana |
| 6,645,247 B2 | 11/2003 | Ferree |
| 6,648,903 B1 | 11/2003 | Pierson |
| 6,648,915 B2 | 11/2003 | Sazy |
| 6,648,918 B2 | 11/2003 | Ferree |
| 6,648,919 B2 | 11/2003 | Ferree |
| 6,648,920 B2 | 11/2003 | Ferree |
| 6,652,585 B2 | 11/2003 | Lange |
| 6,685,695 B2 | 2/2004 | Ferree |
| 6,689,125 B1 | 2/2004 | Keith et al. |
| 6,689,140 B2 | 2/2004 | Cohen |
| 6,712,853 B2 | 3/2004 | Kuslich |
| 6,719,797 B1 | 4/2004 | Ferree |
| 6,723,038 B1 | 4/2004 | Schroeder et al. |
| 6,726,696 B1 | 4/2004 | Houser et al. |
| 6,730,127 B2 | 5/2004 | Michelson |
| 6,733,496 B2 | 5/2004 | Sharkey et al. |
| 6,736,815 B2 | 5/2004 | Ginn |
| 6,749,605 B2 | 6/2004 | Ashley et al. |
| 6,755,777 B2 | 6/2004 | Schweich et al. |
| 6,783,546 B2 | 8/2004 | Zuckerman et al. |
| 6,793,618 B2 | 9/2004 | Schweich et al. |
| 6,793,677 B2 | 9/2004 | Ferree |
| 6,805,695 B2 | 10/2004 | Keith et al. |
| 6,821,276 B2 | 11/2004 | Lambrecht et al. |
| 6,821,277 B2 | 11/2004 | Teitelbaum |
| 6,855,166 B2 | 2/2005 | Kohrs |
| 6,878,167 B2 | 4/2005 | Ferree |
| 6,883,520 B2 | 4/2005 | Lambrecht et al. |
| 6,893,466 B2 | 5/2005 | Trieu |
| 6,932,841 B2 | 8/2005 | Skylar et al. |
| 6,936,072 B2 | 8/2005 | Lambrecht et al. |
| 6,964,674 B1 | 11/2005 | Matsuura et al. |
| 6,966,910 B2 | 11/2005 | Ritland |
| 6,966,916 B2 | 11/2005 | Kumar |
| 6,969,404 B2 | 11/2005 | Ferree |
| 6,974,479 B2 | 12/2005 | Trieu |
| 6,984,247 B2 | 1/2006 | Cauthen |
| 6,986,771 B2 | 1/2006 | Paul et al. |
| 6,989,031 B2 | 1/2006 | Michelson |
| 6,997,953 B2 | 2/2006 | Chung et al. |
| 6,997,956 B2 | 2/2006 | Cauthen |
| 7,004,970 B2 | 2/2006 | Cauthen |
| 7,008,423 B2 | 3/2006 | Assaker et al. |
| 7,018,379 B2 | 3/2006 | Drewry et al. |
| 7,018,414 B2 | 3/2006 | Brau et al. |
| 7,025,771 B2 | 4/2006 | Kuslich et al. |
| 7,033,393 B2 | 4/2006 | Gainer et al. |
| 7,033,395 B2 | 4/2006 | Cauthen |
| 7,041,138 B2 | 5/2006 | Lange |
| 7,052,497 B2 | 5/2006 | Sherman et al. |
| 7,052,516 B2 | 5/2006 | Cauthen, III et al. |
| 7,056,345 B2 | 6/2006 | Kuslich |
| 7,077,862 B2 | 7/2006 | Vidlund et al. |
| 7,094,258 B2 | 8/2006 | Lambrecht et al. |
| 7,115,129 B2 | 10/2006 | Heggeness et al. |
| 7,124,761 B2 | 10/2006 | Lambrecht et al. |
| 7,144,397 B2 | 12/2006 | Lambrecht et al. |
| 7,150,750 B2 | 12/2006 | Damarati |
| 7,163,561 B2 | 1/2007 | Michelson |
| 7,172,627 B2 | 2/2007 | Fiere et al. |
| 7,182,782 B2 | 2/2007 | Kirschman |
| 7,189,199 B2 | 3/2007 | McCarthy et al. |
| 7,189,235 B2 | 3/2007 | Cauthen |
| 7,198,047 B2 | 4/2007 | Lambrecht et al. |
| 7,201,775 B2 | 4/2007 | Gorensek et al. |
| 7,201,776 B2 | 4/2007 | Ferree et al. |
| 7,214,245 B1 | 5/2007 | Marcolongo et al. |
| 7,220,281 B2 | 5/2007 | Lambrecht et al. |
| 7,223,289 B2 | 5/2007 | Trieu et al. |
| 7,232,463 B2 | 6/2007 | Falahee |
| 7,237,497 B2 | 7/2007 | Johnston |
| 7,258,700 B2 | 8/2007 | Lambrecht et al. |
| 7,273,497 B2 | 9/2007 | Ferree et al. |
| 7,285,121 B2 | 10/2007 | Braun et al. |
| 7,297,146 B2 | 11/2007 | Braun et al. |
| 7,318,840 B2 | 1/2008 | McKay |
| 7,326,249 B2 | 2/2008 | Lange |
| 7,331,956 B2 | 2/2008 | Hovda et al. |
| 7,335,213 B1 | 2/2008 | Hyde et al. |
| RE40,156 E | 3/2008 | Sharps et al. |
| 7,344,539 B2 | 3/2008 | Serhan et al. |
| 7,351,262 B2 | 4/2008 | Bindseil et al. |
| 7,354,452 B2 | 4/2008 | Foley |
| 7,354,453 B2 | 4/2008 | McAfee |
| 7,357,798 B2 | 4/2008 | Sharps et al. |
| 7,361,193 B2 | 4/2008 | Frey et al. |
| 7,396,365 B2 | 7/2008 | Michelson |
| 7,435,260 B2 | 10/2008 | Ferree |
| 7,445,634 B2 | 11/2008 | Trieu |
| 7,465,318 B2 | 12/2008 | Sennett et al. |
| 7,491,179 B2 | 2/2009 | Roy et al. |
| 7,491,236 B2 | 2/2009 | Cragg et al. |
| 7,500,978 B2 | 3/2009 | Gorensek et al. |
| 7,503,936 B2 | 3/2009 | Trieu |
| 7,507,243 B2 | 3/2009 | Lambrecht et al. |
| 7,513,911 B2 | 4/2009 | Lambrecht et al. |
| 7,524,333 B2 | 4/2009 | Lambrecht et al. |
| 7,534,267 B2 | 5/2009 | Eckman |
| 7,534,268 B2 | 5/2009 | Hudgins et al. |
| 7,553,329 B2 | 6/2009 | Lambrecht et al. |
| 7,553,330 B2 | 6/2009 | Lambrecht et al. |
| 7,563,282 B2 | 7/2009 | Lambrecht et al. |
| 7,575,577 B2 | 8/2009 | Boyd et al. |
| 7,578,835 B2 | 8/2009 | Wang et al. |
| 7,579,322 B2 | 8/2009 | Akella et al. |
| 7,601,157 B2 | 10/2009 | Boyd et al. |
| 7,601,172 B2 | 10/2009 | Segal et al. |
| 7,611,536 B2 | 11/2009 | Michelson |
| 7,615,076 B2 | 11/2009 | Cauthen et al. |
| 7,618,461 B2 | 11/2009 | Trieu |
| 7,632,313 B2 | 12/2009 | Bhatnagar et al. |
| 7,637,951 B2 | 12/2009 | Michelson |
| 7,658,765 B2 | 2/2010 | Lambrecht et al. |
| 7,666,205 B2 | 2/2010 | Weikel et al. |
| 7,670,379 B2 | 3/2010 | Cauthen |
| 7,670,380 B2 | 3/2010 | Cauthen, III |
| 7,682,392 B2 | 3/2010 | Serhan et al. |
| 7,682,393 B2 | 3/2010 | Trieu et al. |
| 7,695,425 B2 | 4/2010 | Schweich et al. |
| 7,708,733 B2 | 5/2010 | Sanders et al. |
| 7,713,301 B2 | 5/2010 | Bao et al. |

| Patent/Publication | Date | Inventor |
|---|---|---|
| 7,717,961 B2 | 5/2010 | Lambrecht et al. |
| 7,722,523 B2 | 5/2010 | Mortier et al. |
| 7,727,241 B2 | 6/2010 | Gorensek et al. |
| 7,740,659 B2 | 6/2010 | Zarda et al. |
| 7,740,660 B2 | 6/2010 | Collins et al. |
| 7,749,230 B2 | 7/2010 | Yuan et al. |
| 7,749,273 B2 | 7/2010 | Cauthen et al. |
| 7,749,275 B2 | 7/2010 | Lambrecht et al. |
| 7,753,941 B2 | 7/2010 | Keith et al. |
| 7,763,051 B2 | 7/2010 | Labrom et al. |
| 7,763,077 B2 | 7/2010 | Friedman et al. |
| 7,766,812 B2 | 8/2010 | Schroeder et al. |
| 7,766,965 B2 | 8/2010 | Bao et al. |
| 7,776,096 B2 | 8/2010 | Cauthen |
| 7,799,060 B2 | 9/2010 | Lange et al. |
| 7,803,188 B2 | 9/2010 | Justis et al. |
| 7,828,850 B2 | 11/2010 | Cauthen, III et al. |
| 7,833,251 B1 | 11/2010 | Ahlgren et al. |
| 7,837,733 B2 | 11/2010 | Collins et al. |
| 7,857,855 B2 | 12/2010 | Ferree |
| 7,857,857 B2 | 12/2010 | Kim |
| 7,867,278 B2 | 1/2011 | Lambrecht et al. |
| 7,879,097 B2 | 2/2011 | Lambrecht et al. |
| 7,905,885 B2 | 3/2011 | Johnson et al. |
| 7,931,679 B2 | 4/2011 | Heggeness et al. |
| 7,931,689 B2 | 4/2011 | Hochschuler et al. |
| 7,935,149 B2 | 5/2011 | Michelson |
| 7,942,928 B2 | 5/2011 | Webler et al. |
| 7,946,236 B2 | 5/2011 | Butcher |
| 7,959,676 B2 | 6/2011 | Thramann et al. |
| 7,959,679 B2 | 6/2011 | Lambrecht |
| 7,959,683 B2 | 6/2011 | Semler et al. |
| 7,967,864 B2 | 6/2011 | Schaller et al. |
| 7,972,337 B2 | 7/2011 | Boyajian et al. |
| 7,972,363 B2 | 7/2011 | Moskowitz et al. |
| 7,993,402 B2 | 8/2011 | Sidler |
| 7,998,213 B2 | 8/2011 | Lambrecht et al. |
| 8,012,211 B2 | 9/2011 | Kuslich |
| 8,021,425 B2 | 9/2011 | Lambrecht et al. |
| 8,025,698 B2 | 9/2011 | Lambrecht et al. |
| 8,105,384 B2 | 1/2012 | Lambrecht et al. |
| 8,114,082 B2 | 2/2012 | Boyajian et al. |
| 8,231,678 B2 | 7/2012 | Lambrecht |
| 8,257,437 B2 | 9/2012 | Lambrecht et al. |
| 2001/0004710 A1 | 6/2001 | Felt et al. |
| 2001/0031963 A1 | 10/2001 | Sharkey et al. |
| 2002/0007218 A1 | 1/2002 | Cauthen |
| 2002/0026244 A1 | 2/2002 | Trieu |
| 2002/0045942 A1 | 4/2002 | Ham |
| 2002/0049498 A1 | 4/2002 | Yuksel et al. |
| 2002/0111688 A1 | 8/2002 | Cauthen |
| 2002/0120270 A1 | 8/2002 | Trieu et al. |
| 2002/0120337 A1 | 8/2002 | Cauthen |
| 2002/0123807 A1 | 9/2002 | Cauthen, III |
| 2002/0133155 A1 | 9/2002 | Ferree |
| 2002/0143329 A1 | 10/2002 | Serhan et al. |
| 2002/0147496 A1 | 10/2002 | Belef et al. |
| 2002/0151980 A1 | 10/2002 | Cauthen |
| 2002/0198599 A1 | 12/2002 | Haldimann |
| 2003/0004574 A1 | 1/2003 | Ferree |
| 2003/0040796 A1 | 2/2003 | Ferree |
| 2003/0045937 A1 | 3/2003 | Ginn |
| 2003/0050702 A1 | 3/2003 | Berger |
| 2003/0074075 A1 | 4/2003 | Thomas, Jr. et al. |
| 2003/0074076 A1 | 4/2003 | Ferree et al. |
| 2003/0078579 A1 | 4/2003 | Ferree |
| 2003/0130738 A1 | 7/2003 | Hovda et al. |
| 2003/0149438 A1 | 8/2003 | Nichols et al. |
| 2003/0158604 A1 | 8/2003 | Cauthen et al. |
| 2003/0195514 A1 | 10/2003 | Trieu et al. |
| 2004/0010317 A1 | 1/2004 | Lambrecht et al. |
| 2004/0024465 A1 | 2/2004 | Lambrecht et al. |
| 2004/0034353 A1 | 2/2004 | Michelson |
| 2004/0044412 A1 | 3/2004 | Lambrecht et al. |
| 2004/0097927 A1 | 5/2004 | Yeung et al. |
| 2004/0097980 A1 | 5/2004 | Ferree |
| 2004/0116922 A1 | 6/2004 | Hovda et al. |
| 2004/0138673 A1 | 7/2004 | Lambrecht et al. |
| 2004/0249464 A1 | 12/2004 | Bindseil et al. |
| 2004/0260238 A1 | 12/2004 | Call |
| 2004/0260300 A1 | 12/2004 | Gorensek et al. |
| 2004/0260305 A1 | 12/2004 | Gorensek et al. |
| 2004/0260397 A1 | 12/2004 | Lambrecht et al. |
| 2005/0004578 A1 | 1/2005 | Lambrecht et al. |
| 2005/0010205 A1 | 1/2005 | Hovda et al. |
| 2005/0015148 A1 | 1/2005 | Jansen et al. |
| 2005/0027362 A1 | 2/2005 | Williams et al. |
| 2005/0033440 A1 | 2/2005 | Lambrecht et al. |
| 2005/0033441 A1 | 2/2005 | Lambrecht et al. |
| 2005/0038519 A1 | 2/2005 | Lambrecht et al. |
| 2005/0060038 A1 | 3/2005 | Lambrecht et al. |
| 2005/0143825 A1 | 6/2005 | Enayati |
| 2005/0206039 A1 | 9/2005 | Lambrecht et al. |
| 2005/0240269 A1 | 10/2005 | Lambrecht et al. |
| 2005/0278023 A1 | 12/2005 | Zwirkoski |
| 2006/0030857 A1 | 2/2006 | de Villiers et al. |
| 2006/0030884 A1 | 2/2006 | Yeung et al. |
| 2006/0052874 A1 | 3/2006 | Johnson et al. |
| 2006/0085081 A1 | 4/2006 | Shadduck et al. |
| 2006/0089717 A1 | 4/2006 | Krishna et al. |
| 2006/0100304 A1 | 5/2006 | Vresilovic et al. |
| 2006/0106461 A1 | 5/2006 | Embry et al. |
| 2006/0129156 A1 | 6/2006 | Cauthen et al. |
| 2006/0161162 A1 | 7/2006 | Lambrecht et al. |
| 2006/0184246 A1 | 8/2006 | Zwirkoski |
| 2006/0200246 A1 | 9/2006 | Lambrecht et al. |
| 2006/0217747 A1 | 9/2006 | Ferree |
| 2006/0217811 A1 | 9/2006 | Lambrecht et al. |
| 2006/0253121 A1 | 11/2006 | Gorensek et al. |
| 2006/0265077 A1 | 11/2006 | Zwirkoski |
| 2007/0027471 A1 | 2/2007 | Ferree |
| 2007/0061012 A1 | 3/2007 | Cauthen, III |
| 2007/0067039 A1 | 3/2007 | Lambrecht et al. |
| 2007/0093822 A1 | 4/2007 | Dutoit et al. |
| 2007/0093912 A1 | 4/2007 | Borden |
| 2007/0118133 A1 | 5/2007 | Lambrecht et al. |
| 2007/0118226 A1 | 5/2007 | Lambrecht et al. |
| 2007/0135920 A1 | 6/2007 | Ferree |
| 2007/0142839 A1 | 6/2007 | Ferree |
| 2007/0156152 A1 | 7/2007 | Ferree |
| 2007/0156244 A1 | 7/2007 | Cauthen |
| 2007/0162132 A1 | 7/2007 | Messerli |
| 2007/0179623 A1 | 8/2007 | Trieu et al. |
| 2007/0185497 A1 | 8/2007 | Cauthen et al. |
| 2007/0198021 A1 | 8/2007 | Wales |
| 2007/0233146 A1 | 10/2007 | Henniges et al. |
| 2007/0239278 A1 | 10/2007 | Heinz |
| 2007/0260249 A1 | 11/2007 | Boyajian et al. |
| 2007/0276494 A1 | 11/2007 | Ferree |
| 2008/0009792 A1 | 1/2008 | Henniges et al. |
| 2008/0015693 A1 | 1/2008 | Le Couedic |
| 2008/0039586 A1 | 2/2008 | Hasenwinkel et al. |
| 2008/0051800 A1 | 2/2008 | Diaz et al. |
| 2008/0082172 A1 | 4/2008 | Jackson |
| 2008/0140126 A1 | 6/2008 | Ferree |
| 2008/0172058 A1 | 7/2008 | Trieu et al. |
| 2008/0195119 A1 | 8/2008 | Ferree |
| 2008/0215154 A1 | 9/2008 | Lambrecht et al. |
| 2008/0221686 A1 | 9/2008 | Ferree |
| 2008/0243256 A1 | 10/2008 | Ferree |
| 2008/0269898 A1 | 10/2008 | Carls et al. |
| 2009/0012540 A1 | 1/2009 | Ferguson et al. |
| 2009/0024165 A1 | 1/2009 | Ferree |
| 2009/0118833 A1 | 5/2009 | Hudgins et al. |
| 2009/0143862 A1 | 6/2009 | Trieu |
| 2009/0157087 A1 | 6/2009 | Wei et al. |
| 2009/0187249 A1 | 7/2009 | Osman |
| 2009/0204216 A1 | 8/2009 | Biedermann et al. |
| 2009/0204220 A1 | 8/2009 | Trieu |
| 2009/0222093 A1 | 9/2009 | Liu et al. |
| 2009/0234457 A1 | 9/2009 | Lotz et al. |
| 2009/0270989 A1 | 10/2009 | Conner et al. |
| 2009/0270990 A1 | 10/2009 | Louis et al. |
| 2009/0275913 A1 | 11/2009 | Trieu |
| 2009/0281517 A1 | 11/2009 | Lambrecht et al. |
| 2009/0292322 A1 | 11/2009 | Lambrecht |
| 2010/0004664 A1 | 1/2010 | Boyajian et al. |
| 2010/0030333 A1 | 2/2010 | Michelson |

| | | | |
|---|---|---|---|
| 2010/0057143 A1 | 3/2010 | Lambrecht et al. |
| 2010/0087926 A1 | 4/2010 | Butler et al. |
| 2010/0094425 A1 | 4/2010 | Bentley et al. |
| 2010/0114317 A1 | 5/2010 | Lambrecht et al. |
| 2010/0121455 A1 | 5/2010 | Lambrecht et al. |
| 2010/0145454 A1 | 6/2010 | Hoffman |
| 2010/0145463 A1 | 6/2010 | Michelson |
| 2010/0152784 A1 | 6/2010 | Lowry et al. |
| 2010/0152790 A1 | 6/2010 | Hestad |
| 2010/0161056 A1 | 6/2010 | Voellmicke et al. |
| 2010/0161060 A1 | 6/2010 | Schaller et al. |
| 2010/0185285 A1 | 7/2010 | Perkins |
| 2010/0185286 A1 | 7/2010 | Allard et al. |
| 2010/0191335 A1 | 7/2010 | Root et al. |
| 2010/0204797 A1 | 8/2010 | Lambrecht et al. |
| 2010/0211108 A1 | 8/2010 | Lemole |
| 2010/0298837 A1 | 11/2010 | Gorensek |
| 2011/0022061 A1 | 1/2011 | Orphanos et al. |
| 2011/0106264 A1 | 5/2011 | Lambrecht et al. |
| 2011/0118844 A1 | 5/2011 | Lambrecht |
| 2011/0125271 A1 | 5/2011 | Lambrecht |
| 2011/0196492 A1 | 8/2011 | Lambrecht et al. |
| 2011/0264227 A1 | 10/2011 | Boyajian et al. |

FOREIGN PATENT DOCUMENTS

| | | |
|---|---|---|
| EP | 0298235 | 1/1989 |
| EP | 0682910 | 3/1995 |
| EP | 0700671 | 3/1996 |
| EP | 0876808 | 11/1998 |
| EP | 0722700 | 12/1998 |
| EP | 1091776 | 5/2004 |
| EP | 1214026 | 4/2005 |
| EP | 1180978 | 5/2005 |
| FR | 2639823 A1 | 6/1990 |
| JP | S63-95043 | 4/1988 |
| JP | S64-887 | 1/1989 |
| JP | H05-29694 | 7/1993 |
| JP | 1995-148172 | 6/1995 |
| RU | 2020901 | 10/1994 |
| RU | 93031998 A | 11/1995 |
| RU | 2055544 | 3/1996 |
| RU | 2078551 | 5/1997 |
| RU | 96121354 A | 1/1999 |
| WO | WO 92/10982 | 9/1992 |
| WO | WO 93/22990 | 11/1993 |
| WO | WO 95/26689 | 10/1995 |
| WO | WO 95/31946 | 11/1995 |
| WO | WO 95/34331 | 12/1995 |
| WO | WO96/01164 | 1/1996 |
| WO | WO 96/01598 | 1/1996 |
| WO | WO97/26847 | 7/1997 |
| WO | WO97/30638 | 8/1997 |
| WO | WO98/17190 | 4/1998 |
| WO | WO 98/20939 | 5/1998 |
| WO | WO98/34552 | 8/1998 |
| WO | WO98/38918 | 9/1998 |
| WO | WO99/00074 | 1/1999 |
| WO | WO 99/02108 | 1/1999 |
| WO | WO99/02214 | 1/1999 |
| WO | WO99/03422 | 1/1999 |
| WO | WO99/30651 | 6/1999 |
| WO | WO99/47058 | 9/1999 |
| WO | WO 99/61084 | 9/1999 |
| WO | WO99/62439 | 12/1999 |
| WO | WO 00/14708 | 3/2000 |
| WO | WO 00/18328 | 4/2000 |
| WO | WO00/42953 | 7/2000 |
| WO | WO00/44288 | 8/2000 |
| WO | WO 00/45741 | 8/2000 |
| WO | WO 00/49978 | 8/2000 |
| WO | WO00/62832 | 10/2000 |
| WO | WO 00/71043 | 11/2000 |
| WO | WO 01/10316 | 2/2001 |
| WO | WO 01/12080 | 2/2001 |
| WO | WO 01/12107 | 2/2001 |
| WO | WO01/21246 | 3/2001 |
| WO | WO 01/28464 | 4/2001 |
| WO | WO01/28468 | 4/2001 |
| WO | WO 01/39696 | 6/2001 |
| WO | WO 01/45579 | 6/2001 |
| WO | WO 01/52914 | 7/2001 |
| WO | WO 01/78616 | 10/2001 |
| WO | WO01/45577 | 6/2002 |
| WO | WO 02/051622 | 7/2002 |
| WO | WO02/058599 | 8/2002 |
| WO | WO02/067824 | 9/2002 |
| WO | WO 03/039328 | 5/2003 |
| WO | WO 03/088876 | 10/2003 |
| WO | WO 2004/080355 | 9/2004 |
| WO | WO 2005/027800 | 3/2005 |

OTHER PUBLICATIONS

Ahlgren, B.D. et al., "Anular Incision Technique on the Strength and Multidirectional Flexibility of the Healing Intervertebral Disc," Spine, 19 (8) : 948-954 (1994).

Bagga C.S., Williams P., Highma P.A., Bao B.Q., "Development of Fatigue Test Model for a Spinal Nucleus Prosthesis with Preliminary Results for a Hydrogel Spinal Prosthetic Nucleus," Proceedings of the 1997 Bioengineering Conference, 441-442: BED—vol. 35, Sunriver, Oregon, Jun. 11-15, 1997.

Balderston, R.A., et al., "The Treatment of Lumbar Disc Herniation: Simple Fragment Excision Versus Disc Space Curettage," J. of Spinal Disorders, 4 (1) : 22-25 (1991).

Bao Q.B., Bagga C.S., "The Dynamic Mechanical Analysis of Hydrogel Elastomers," Thermochimica Acta, 226:107-113 (1993).

Bao Q.B., McCullen G.M., Higham P.A., Dumbleton J.H., Yuan H.A., "The Artificial Disc: Theory, Design and Materials," Biomaterials, vol. 17, No. 12:1157-1167 (1996).

Bao Q.B., Yuan H.A., "Artificial Disc Technology," Neurosurg Focus 9(4), 2000.

Barr, J.S., "Ruptured Intervertebral Disc and Sciatic Pain," J. of Bone and Joint Surgery, 29, (2) : 429-437 (1947).

Brinckmann, P., et al., "Change of Disc Height, Radial Disc Bulge, and Intradiscal Pressure From Discectomy an in Vitro Investigation on Human Lumbar Discs," Spine, 16 (6) : 641-646 (1991).

Goel, V.K., et al., "Mechanical Properties of Lumbar Spinal Motion Segments as Affected by Partial Disc Removal," Spine, 11 (10) : 1008-1012 (1986).

Hanley, E.N., Jr., et al., "The Development of Low-Back Pain After Excision of a Lumbar Disc," J. of Bone and Joint Surgery, 71A (5) : 719-721 (1989).

Hedman T.P., Kostuik J.P., Fernie G.R., Hellier W.G., "Design of an Intervertebral Disc Prosthesis," Spine 16 (Suppl. 6):S256-S260 (1991).

Heggeness, M.H., et al., "Discography of Lumbar Discs After Surgical Treatment for Disc Herniation," Spine, 22 (14) : 1606-1609 (1997).

Husson J.L., Baumgartner W., Le Huec J.C., "Nucléoplastie Inter-Somatique Par Voie Postérieure Per-Dissectomie: Concept et Étude Expérimentale," Restabilisation Inter-Somatique Due Rachis Lombaire:311-320 (1996).

Husson J.L., Scharer N., Le Nihouannen J.C., Freudiger S., Baumgartner W., Polard J.L., "Nucleoplasty During Discectomy Concept and Experimental Study," Rachis vol. 9, No. 3:145-152 (1997).

Kayama, S. et al., "Incision of the Anulus Fibrosus Induces Nerve Root Morphologic, Vascular, and Functional Changes," Spine, 21 (22) : 2539-2543 (1996).

Khelimsky et al. "Plastic Surgery of Damaged Intervertebral Discs with Fast-Solidifying Glue Composition (Experimental Research)." Collected articles Experimental Traumatic Surgery and Orthopaedics Moscow, 1990, pp. 88-90.

Langrana N.A., Parsons J.R., Lee C.K., Vuono-Hawkins M., Yang S.W., Alexander H., "Materials and Design Concepts for an Intervertebral Disc Spacer. I. Fiber-Reinforced Composite Design," Journal of Applied Biomaterials, vol. 4:125-132 (1994).

Lemaire J.P., Skalli W., Lavaste F., Templier A., Mendes, F., Diop A., Sauty V., Laloux E., "Intervertebral Disc Prosthesis," Clinical Orthopaedics and Related Research, No. 337:64-76 (1997).

Martz E.O., Goel V.K., Pope M.H., Park J.B., "Materials and Design of Spinal Implants—A Review," Journal of Biomedical Materials Research, vol. 38, Issue 3:267-288 (1997).

Postacchini, F., "Spine Update results of Surgery Compared With Conservative Management for Lumbar Disc Herniations," Spine, 21 (11) : 1383-1387 (1996).

Ray C.D., Schonmayr R., Kavanagh S.A., Assell R., "Prosthetic Disc Nucleus Implants," Riv. Neuroradiol 1999:12 (Suppl. 1):157-162.

Rogers, L.A., "Experience with Limited versus Extensive Disc Removal in Patients Undergoing Microsurgical Operations for Ruptured Lumbar Discs," Neurosurgery, 22 (1) : 82-85 (1988).

Sakalkale D.P., Bhagia S.A., Slipman C.W., "A Historical Review and Current Perspective on the Intervertebral Disc Prosthesis," Pain Physician, vol. 6, No. 2:1-4 (2003).

Schonmayr R., Busch C., Lotz C., Lotz-Metz G., "Prosthetic Disc Nucleus Implants: The Wiesbaden Feasibility Study, 2 Years follow-up in Ten patients," Riv. Neuroradiol 1999:12 (Suppl. 1):163-170.

Sheljakin S. Ju. "Percutaneous Diskectomy Skin-through Discectomy in Complex Treatment of Patients with Disc Lumbosacral Polyraduculitis." Abstract of a thesis, St. Petersburg, 1996.

Shul'man Kh.M. "Pathogenetic Therapy of Compression Type Osteochondritis of Spinal Lumbar Region." Collected articles Reconstruction-and-Restoration Treatment in Traumatic Surgery, Orthopaedics, Surgery and Neurosurgery, Kazan', 1976, pp. 17-21.

Shul'man Kh.M. "Surgical Treatment of Compression Type Osteochondritis of Spinal Lumbar Region with Intervertebral Disc Implantation." Kazan', 1980, pp. 174-185.

Shul'man Kh.M., Danilov V.I. "Biochemical Experimental Basis of Intervertebral Disc Prosthesis Implantation Method by Fast-solidifying Polyurethane CKYu-PFL in Case of Disc Degeneration or Traumatic Damage." Collected articles Reconstruction-and-Restoration Treatment in Traumatic Surgery, Orthopaedics, Surgery and Neurosurgery. Kazan', 1976, pp. 22-27.

Tibrewal, S.B., et al., "Lumbar Intervertebral Disc Heights in Normal Subjects and Patients with Disc Herniation," Spine, 10 (5) : 452-454 (1985).

Tullberg, T., et al., "Radiographic Changes After Lumbar Discectomy," Spine, 18 (7) : 843-850 (1993).

Usmanov M.M. "Intervertebral Disc Changes at Local Damage of its Elements and Implantation of Various Materials." Abstract of a thesis Moscow, 1991.

USSR Author's Certificate No. 1477390 "Method for Treatment of Osteochondritis." Published May 17, 1989.

USSR Author's Certificate No. 1827204 "Method for Treatment of Spinal Osteochondritis." Published May 15, 1993.

Yasargil, M.G., Microsurgical Operation of Herniated Lumbar Disc, Adv. Neurosurg 1977; 4:81.

Zelentsov E.V. "Plastic Surgery with Collagen of Intervertebral Discs for Surgical Treatment of Lumbosacral Polyradiculitis." Abstract of a thesis, Leningrad, 1990.

Zelentsov E.V. et al. "Application of Collagen for Experimental Plastic Surgery of Intervertebral Discs." Collected articles Integrated Treating of Pain Syndromes of Neurogenic Origin, Leningrad 1984 pp. 86-90.

* cited by examiner

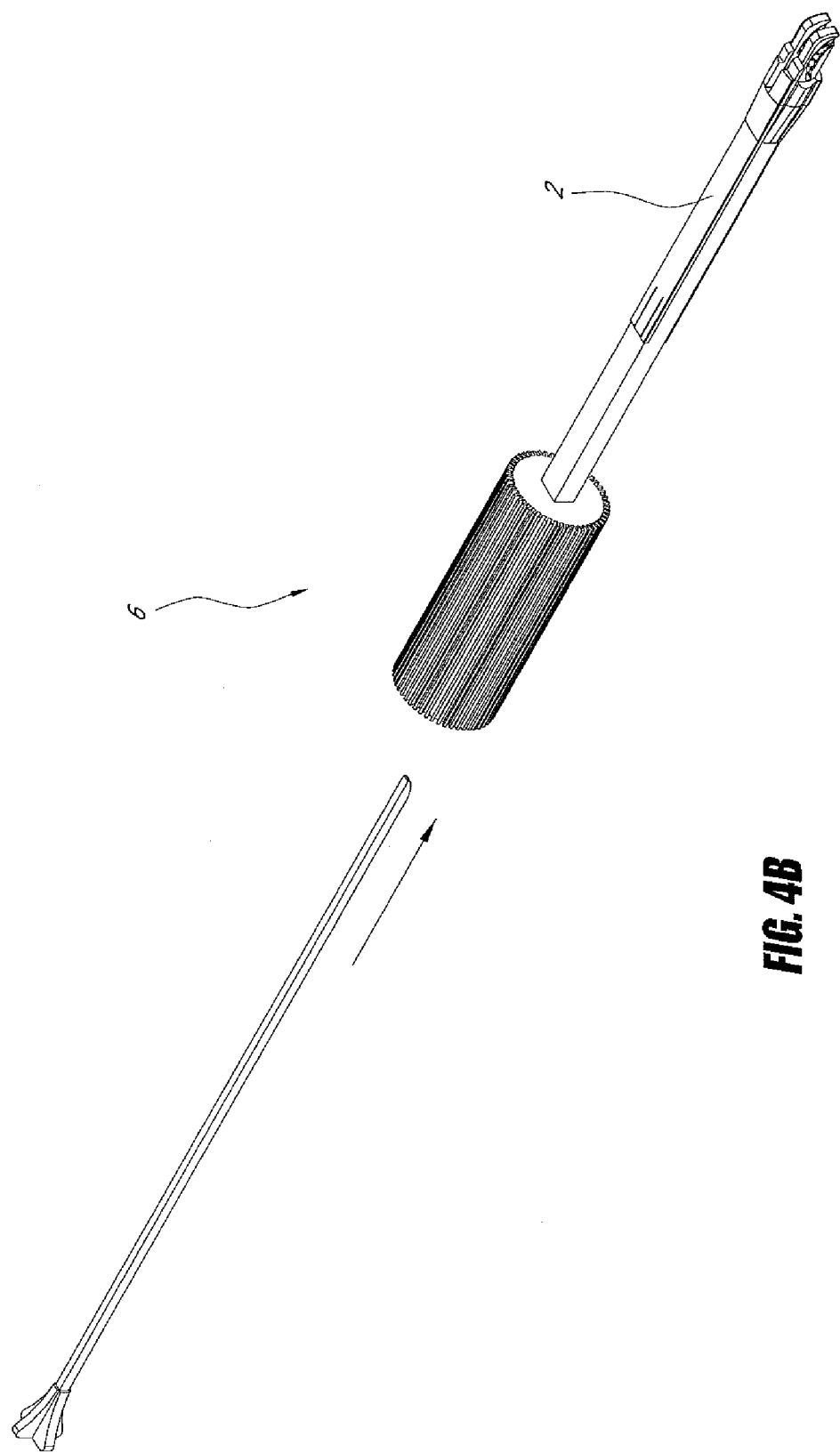

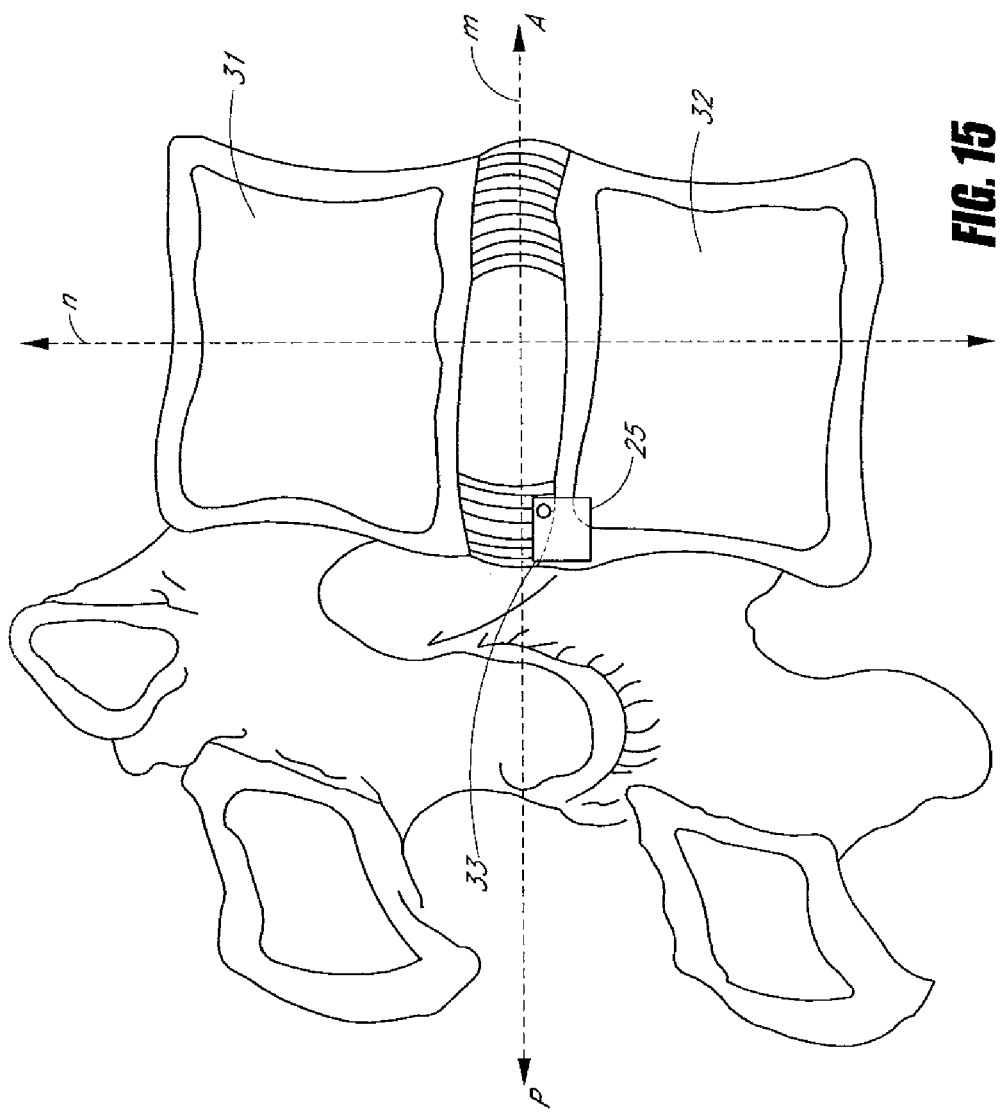

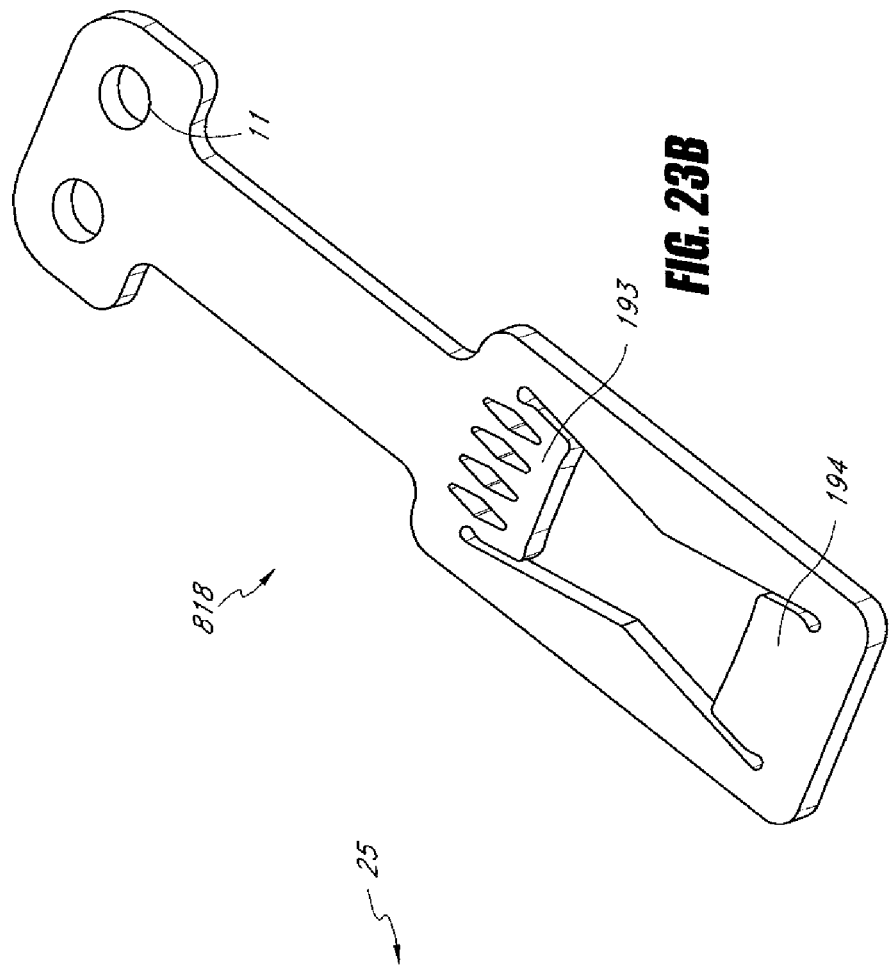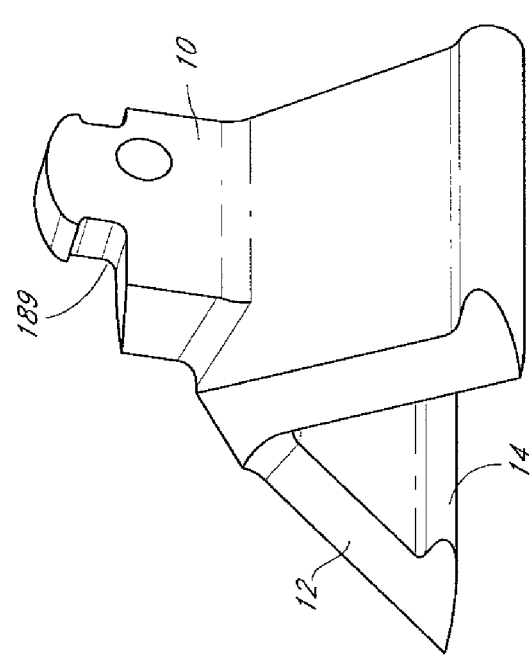

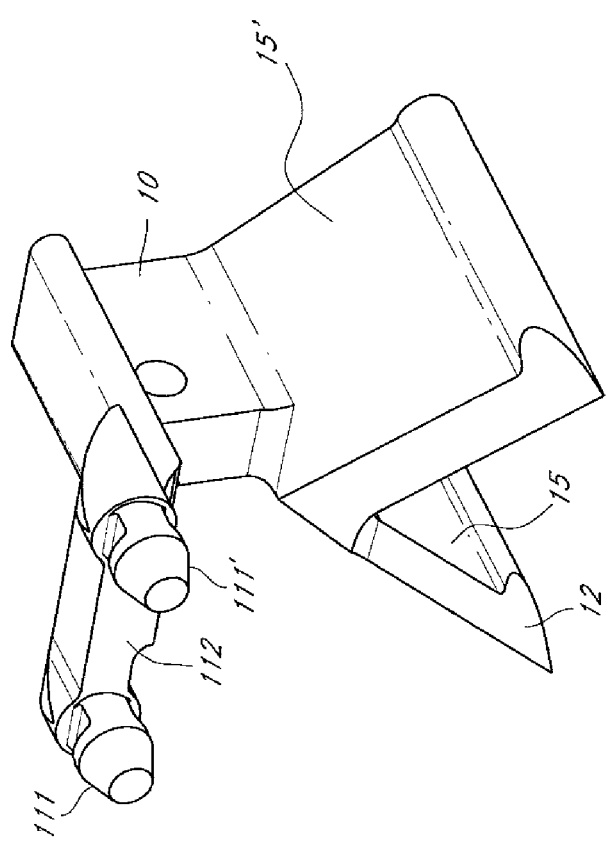

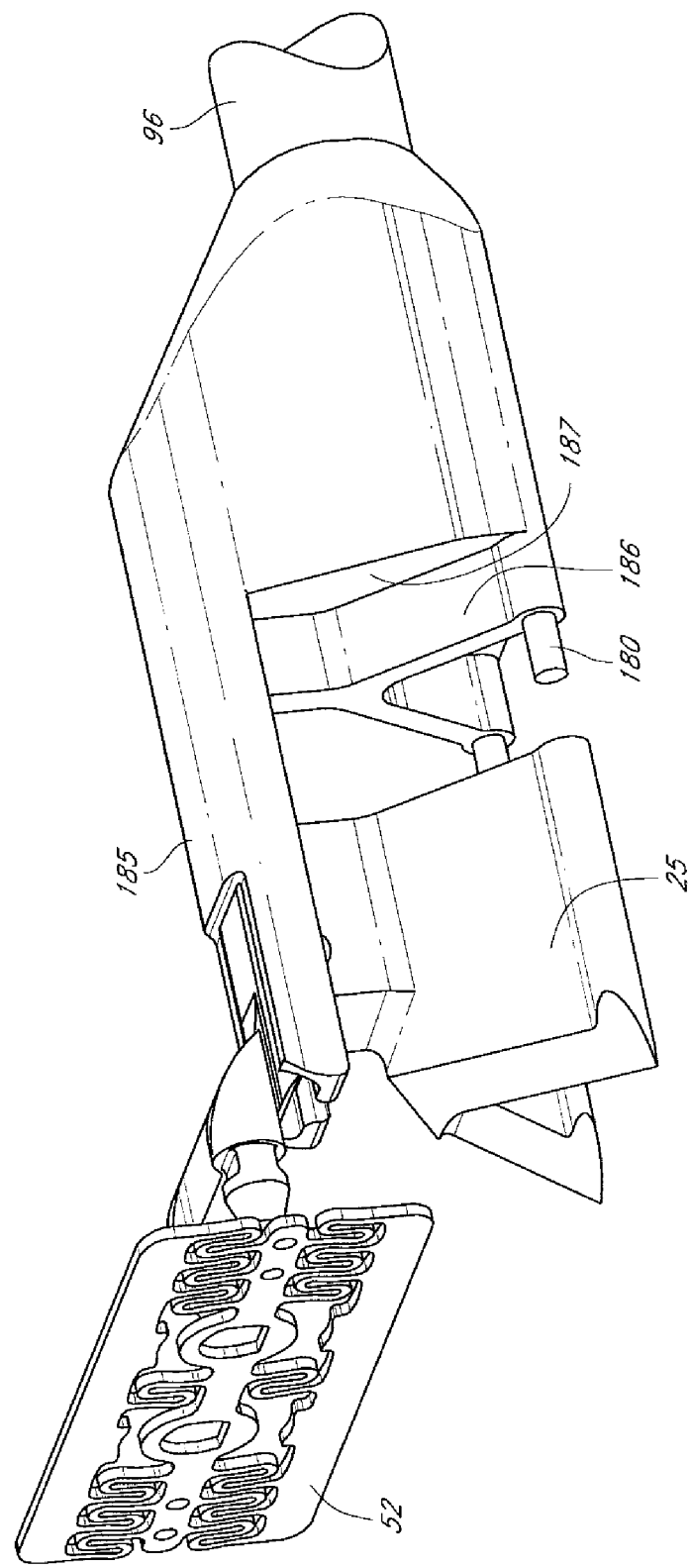

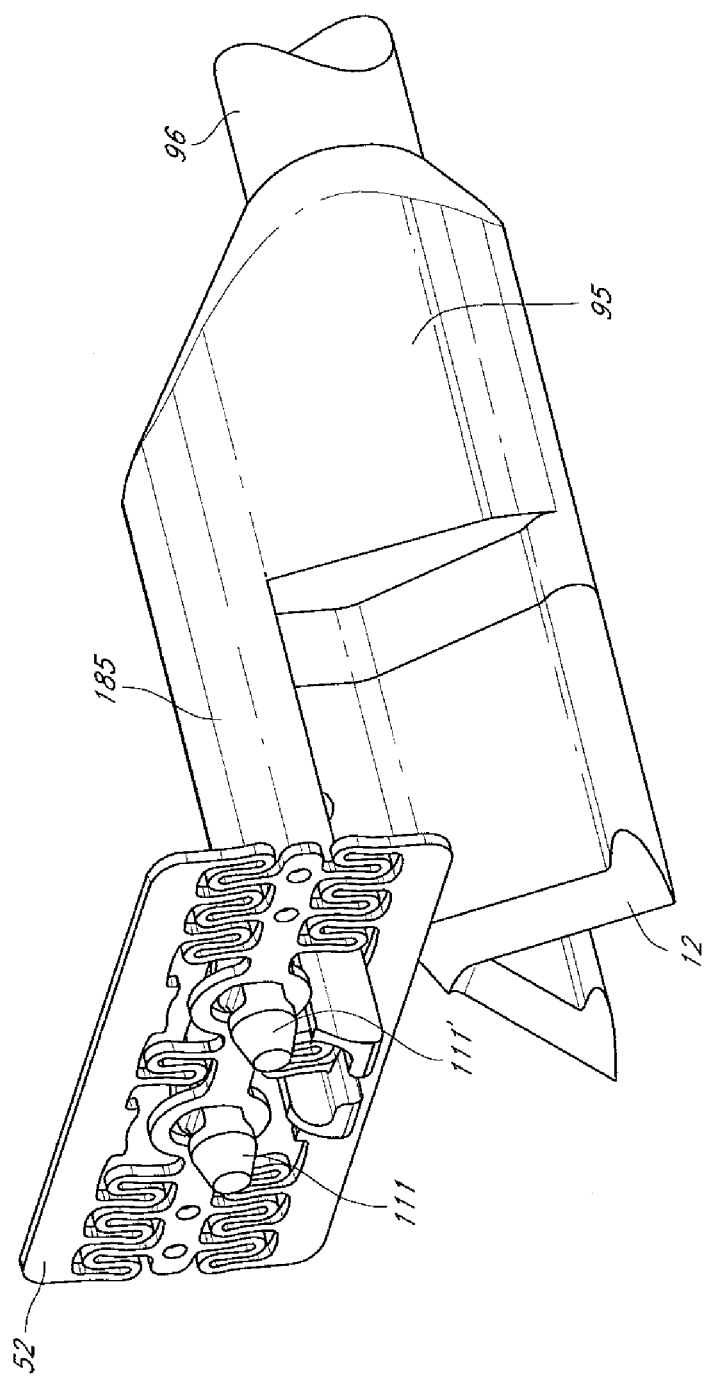

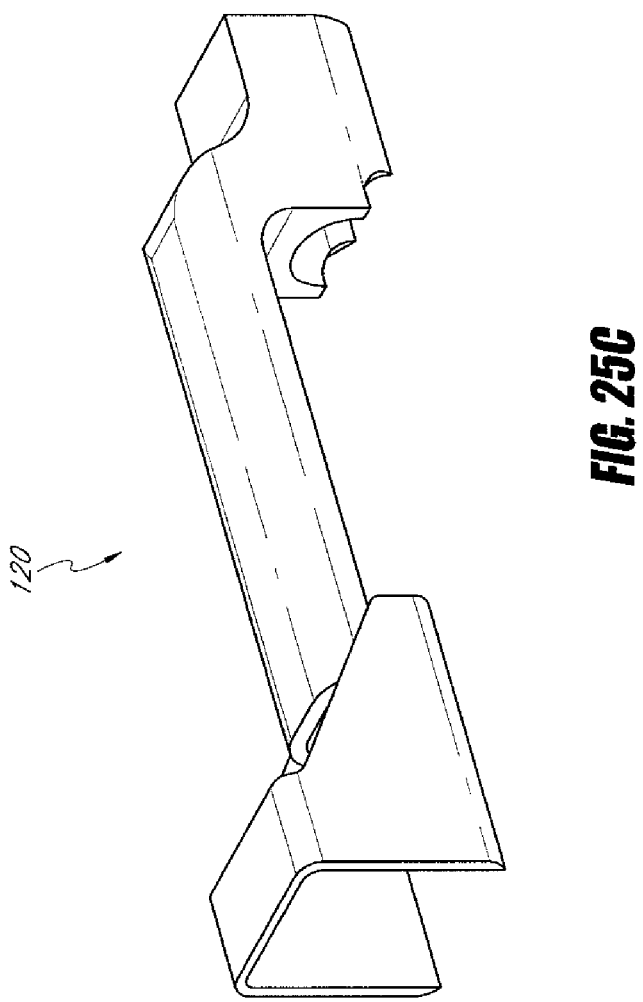

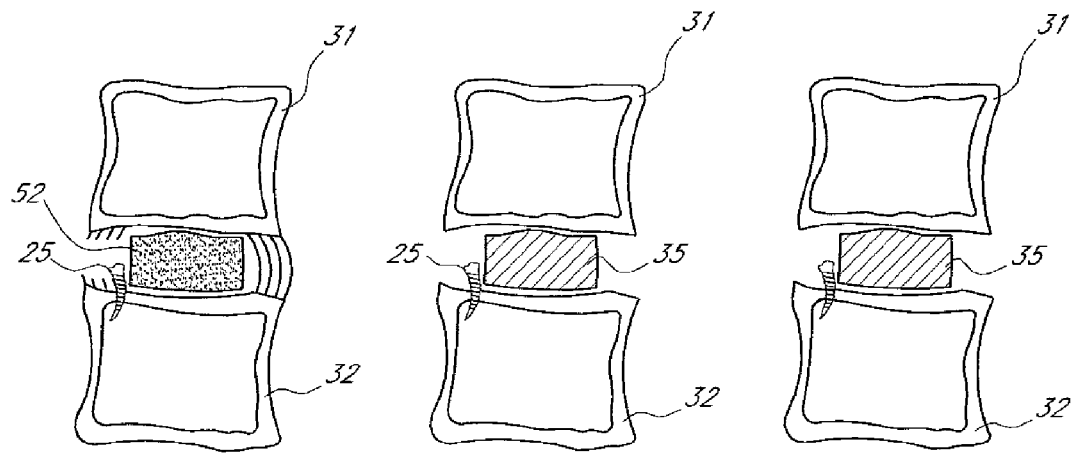
FIG. 29A  FIG. 29B  FIG. 29C
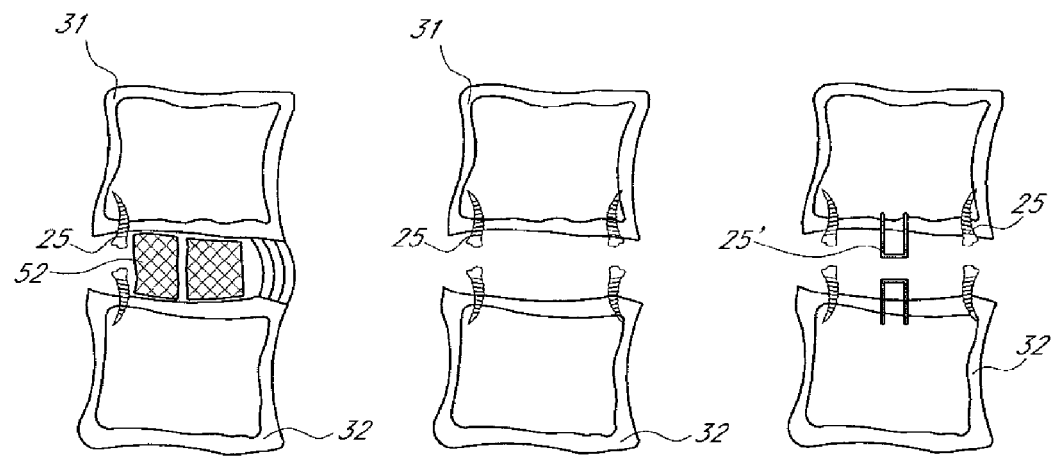
FIG. 29D  FIG. 29E  FIG. 29F

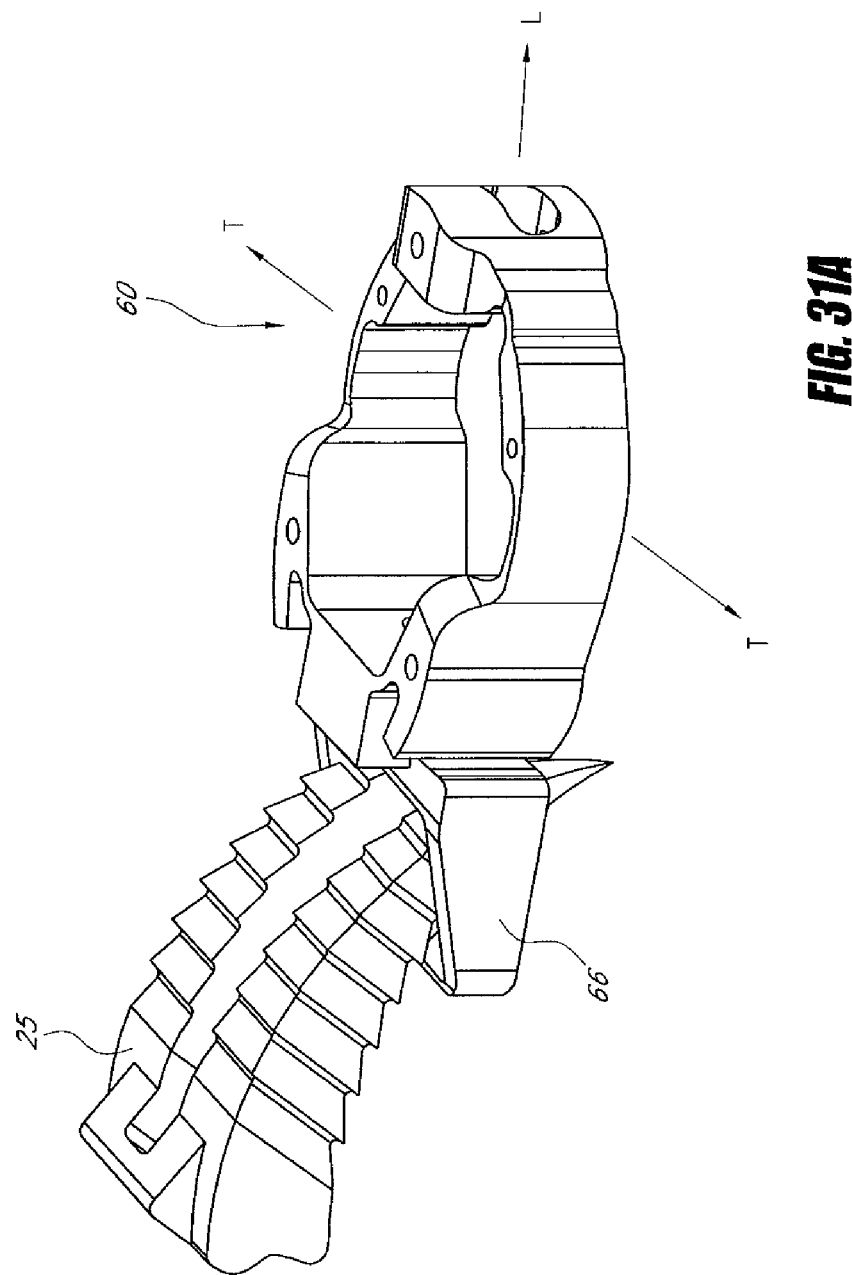

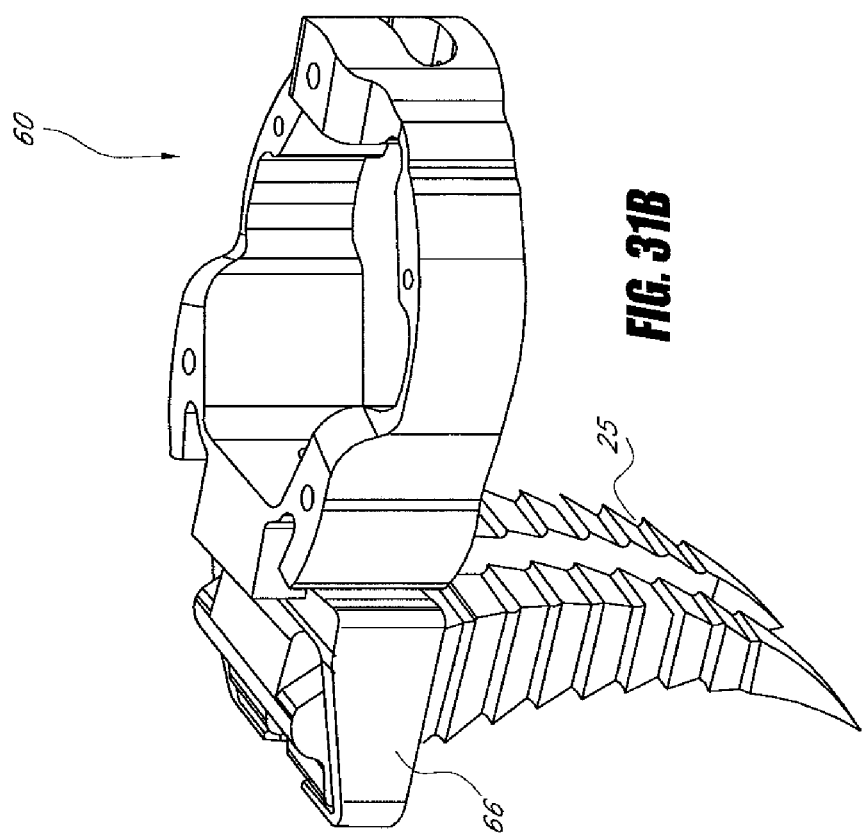

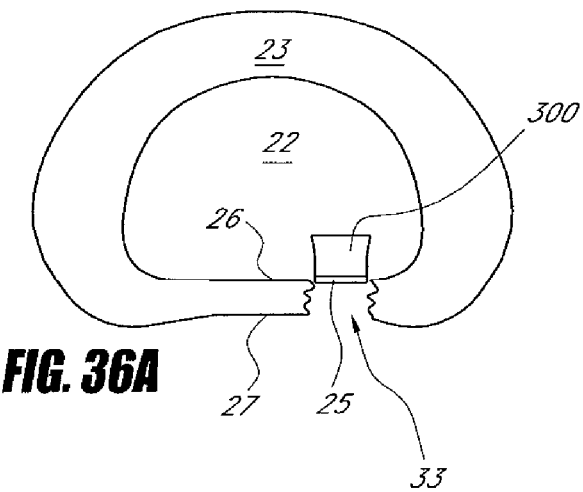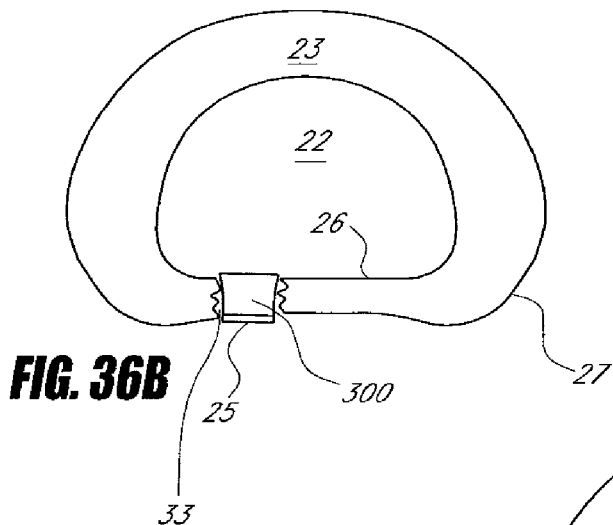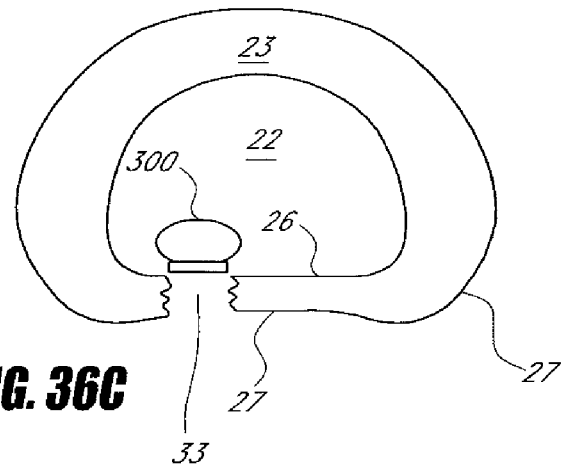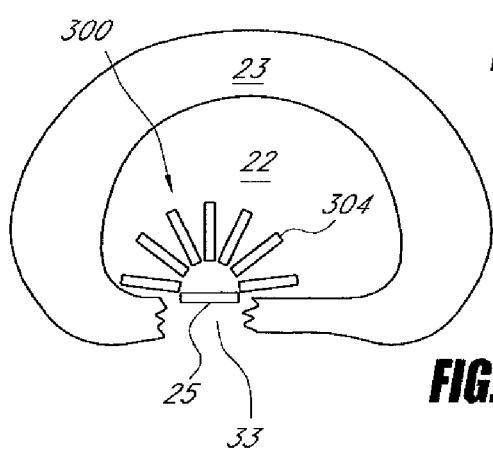
FIG. 36A
FIG. 36B
FIG. 36C
FIG. 37

FIG. 39C
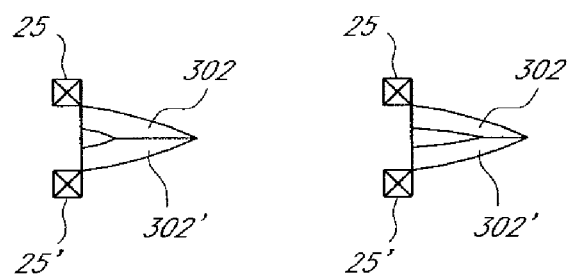
FIG. 40A     FIG. 40B
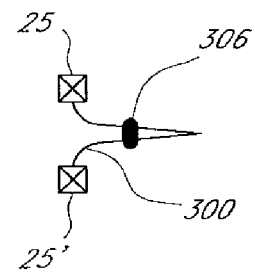
FIG. 41

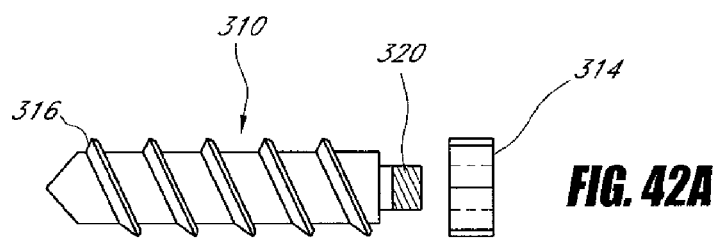
FIG. 42A
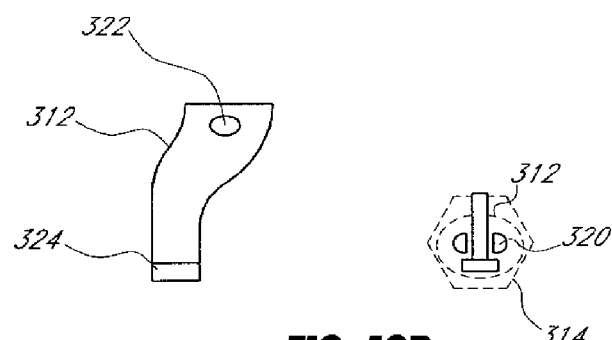
FIG. 42B
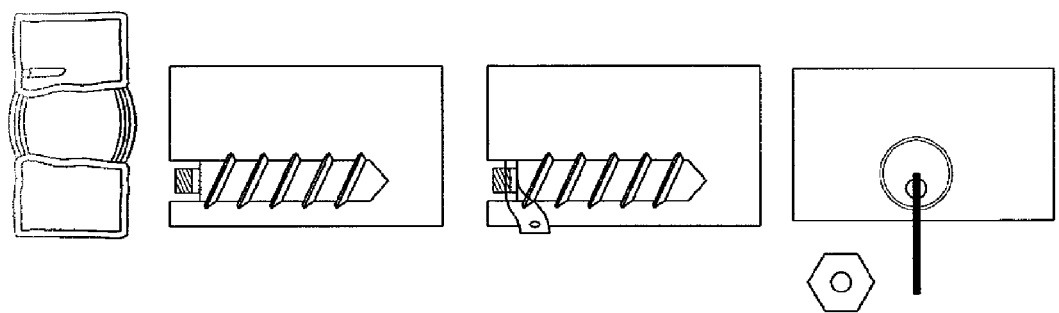
FIG. 43A  FIG. 43B  FIG. 43C  FIG. 43D

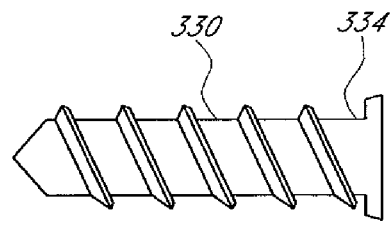
FIG. 44A
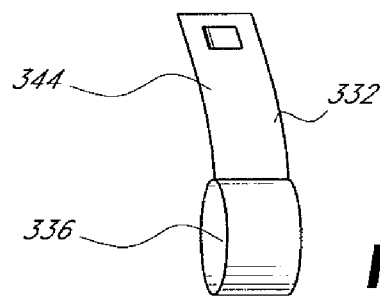
FIG. 44B
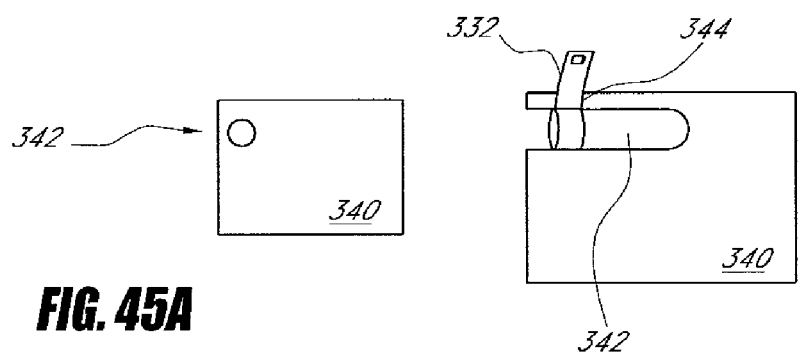
FIG. 45A  FIG. 45B
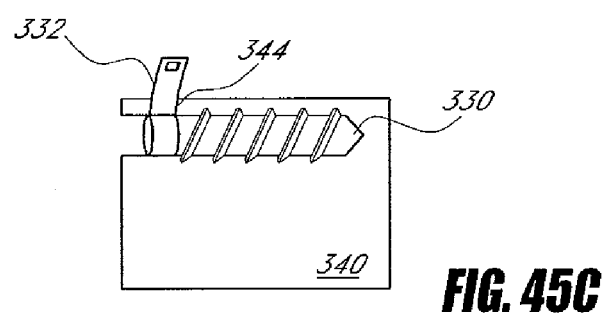
FIG. 45C

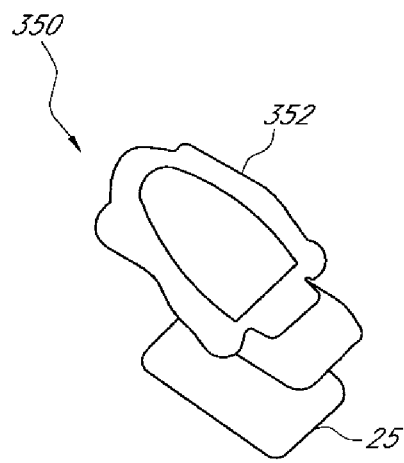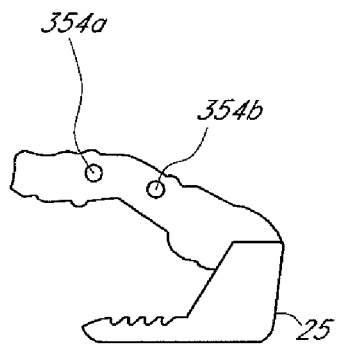
FIG. 46A  FIG. 46B
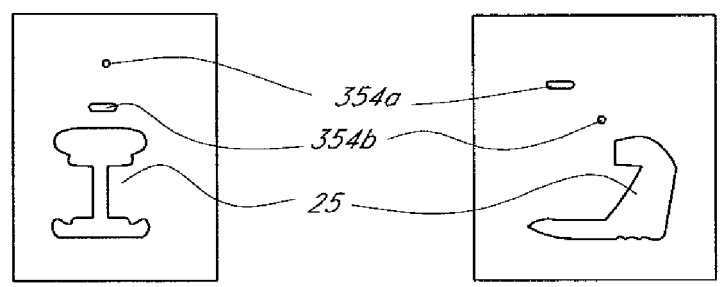
FIG. 47A  FIG. 47B

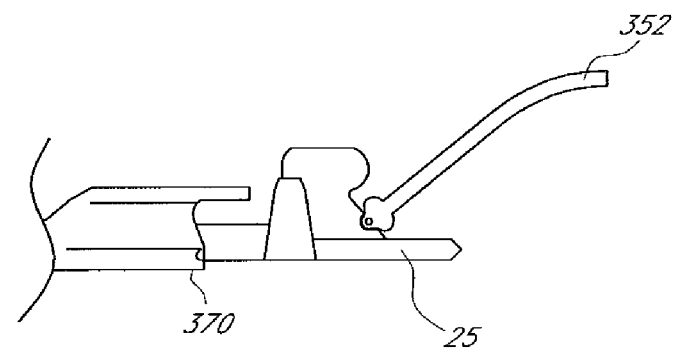
FIG. 48
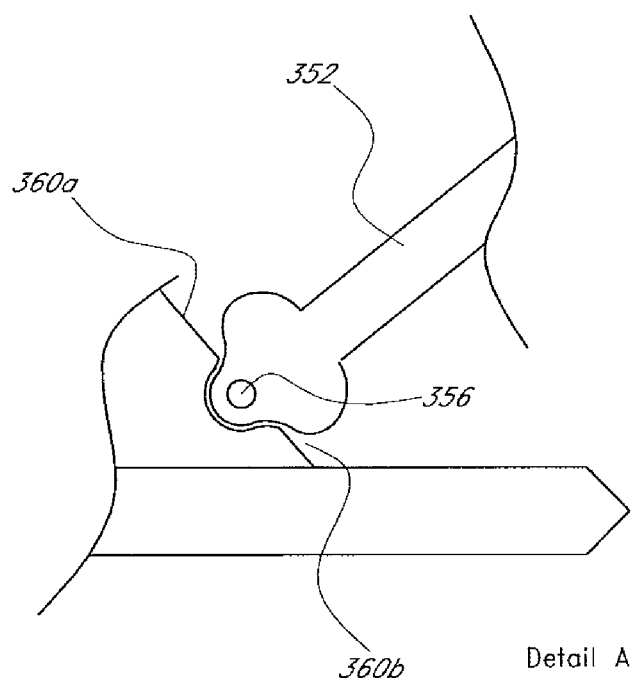
Detail A

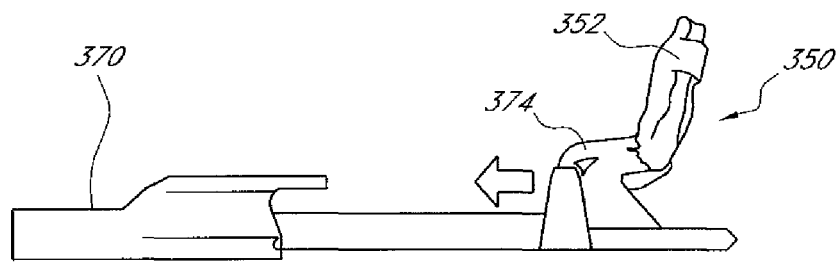
FIG. 50C
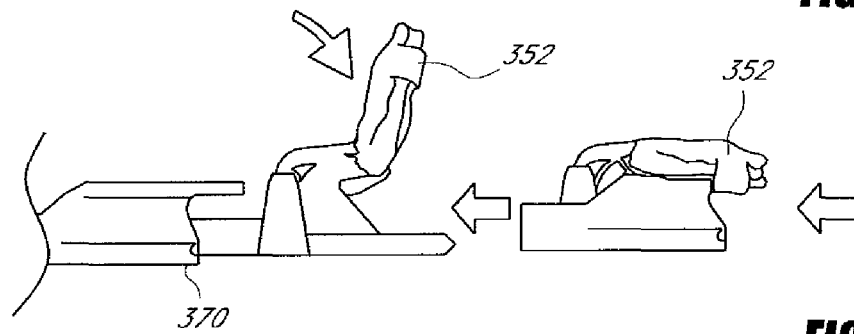
FIG. 50D   FIG. 50E
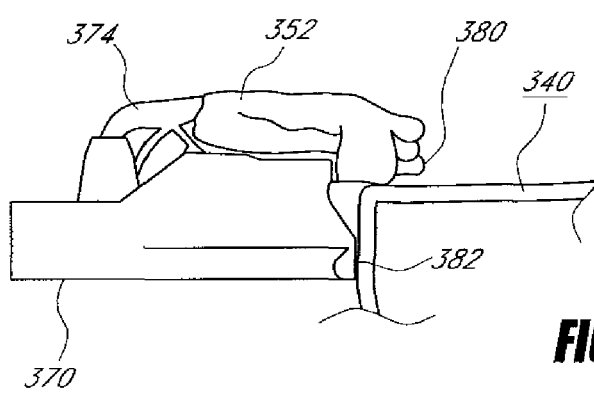
FIG. 51

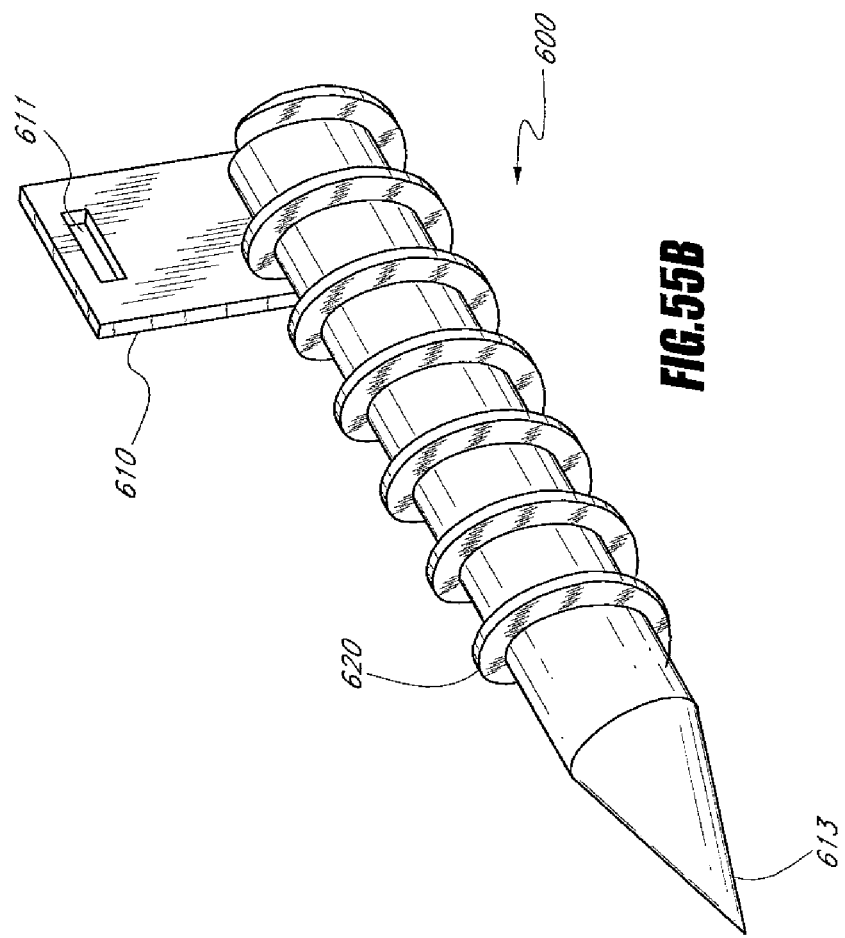

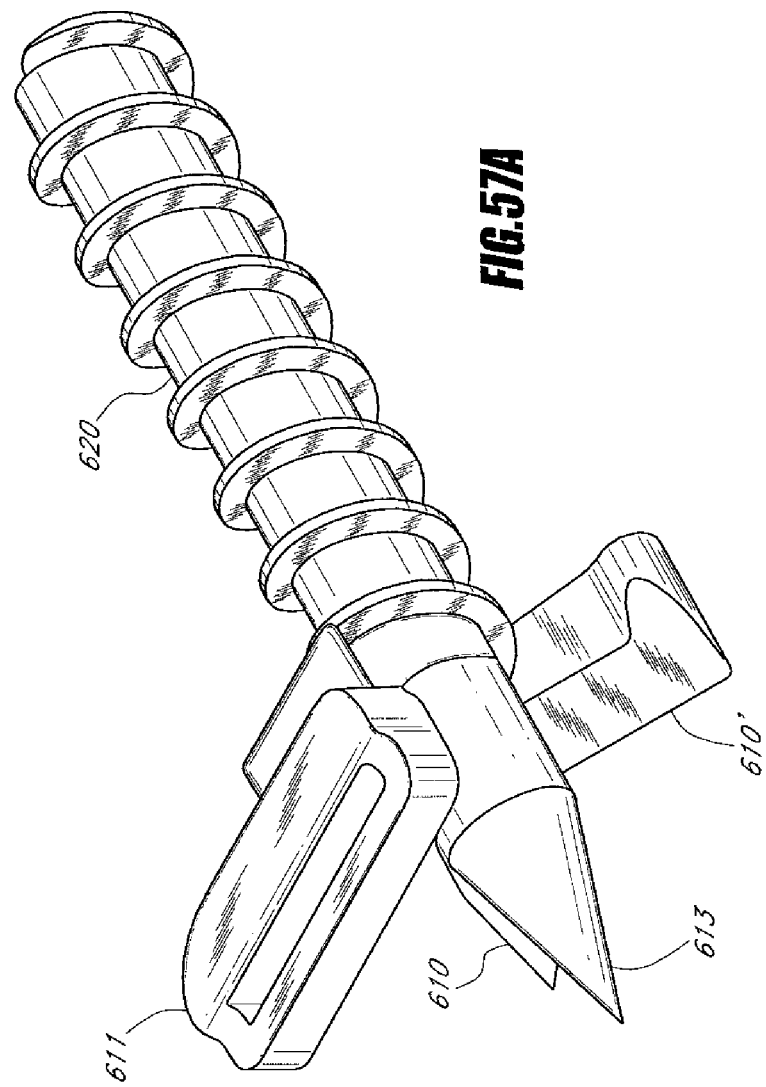

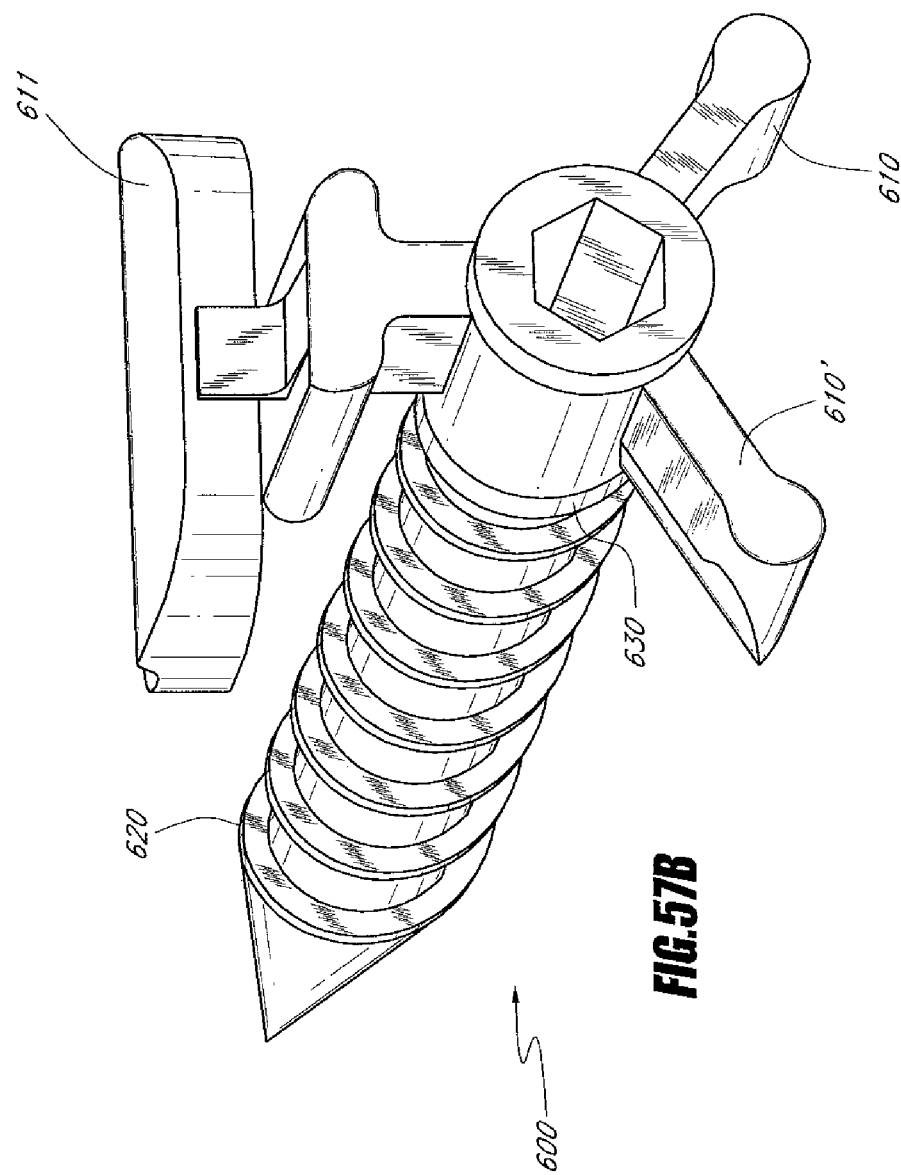

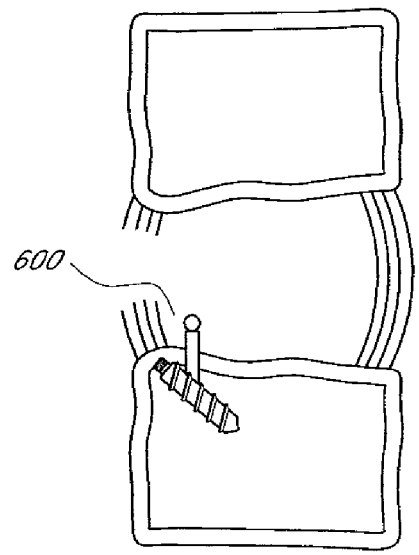
FIG. 58A
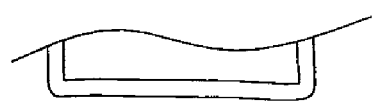
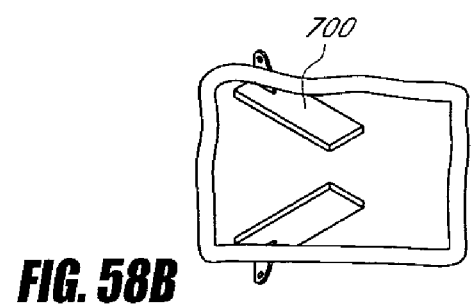
FIG. 58B

METHOD FOR VERTEBRAL ENDPLATE RECONSTRUCTION

CROSS-REFERENCE TO RELATED APPLICATIONS

This application is a continuation of U.S. patent application Ser. No. 12/524,334, filed Jul. 23, 2009, which is a National Phase Application of International Application Number PCT/US2008/075496, filed Sep. 5, 2008, published as International Publication Number WO 2009/033100 on Mar. 12, 2009, which claims the benefit of U.S. Provisional Application Nos. 60/967,782, filed Sep. 7, 2007; 61/066,334, filed Feb. 20, 2008; 61/066,700, filed Feb. 22, 2008; and 61/126,548, filed May 5, 2008. This application hereby expressly incorporates by reference each of the above-identified applications in their entirety.

BACKGROUND

1. Field of the Invention

The invention relates generally to tissue anchors, delivery methods, and associated treatments. Anchors according to one or more embodiments can provide superior pull-out resistance, stability and may, in some embodiments, increase contact with tissue involving a reduced amount of penetration. Delivery methods include linear, lateral, and off-angle implantation or driving of anchors along, against or within tissue surfaces.

2. Description of the Related Art

Anchors described herein can be used throughout the human body and have general applicability to fastener art. Such anchors can be used to join or anchor like or disparate materials or tissues together, maintain alignment of materials, reinforce a fracture within a material, and provide an attachment site along or within a materials surface. Generally the art includes both staples and screws. For example, U.S. Pat. No. 7,131,973 to Hoffman discloses an anchor and delivery system for treating urinary incontinence. The distal portion of the delivery tool is curved and hooked such that pulling on the instruments handle effects a retrograde delivery of the anchor. U.S. Pat. No. 5,366,479 to McGarry et al. discloses a staple and delivery system. The staple is flat but contains a pair of inwardly curving prongs. U.S. Pat. No. 5,391,170 to McGuire et al. discloses an angled screw driver for inserting bone screws in ligament tunnels as part of a ligament reconstruction procedure. U.S. Pat. No. 5,217,462 to Asnis et al. discloses a screw and driver combination having threaded shank and sleeve that cooperate to hold and release the screw. U.S. Pat. No. 5,002,550 to Li discloses a suture anchor with barbs and an installation tool that includes a curved needle for attaching a suture.

SUMMARY

As described above, tissue anchors exist in the prior art. However, there remains a need for anchors and anchoring systems that effectively reconstruct or augment vertebral endplate surfaces. There also exists a need to effectively close defects between opposing endplates.

In one embodiment, a method of reconstructing or augmenting a vertebral endplate is provided. In one embodiment, the method comprises: providing at least a first anchor and a second anchors, wherein each anchor comprises an upper neck and a lower bone engagement portion and wherein the neck has an attachment site for coupling to an augmentation material. The method further comprises identifying a vertebral endplate surface adjacent damaged or removed tissue (or tissue that is otherwise weak or in need of support) and driving the first and second anchors into and along the vertebral endplate adjacent the damaged tissue, wherein the lower bone engagement portion engages the vertebral endplate. The method further comprises coupling the attachment site of the first anchor to a first augmentation material and coupling the attachment site of the second anchor to a second augmentation material. The method also comprises positioning at least a portion of the first and second augmentation material or the neck above the endplate surface, and connecting the first anchor to the second anchor and/or connecting the first augmentation material to the second augmentation material, thereby reconstructing or augmenting the vertebral endplate.

In one embodiment, the augmentation material comprises a bone graft, an expandable frame and/or cement, or combinations thereof. In one embodiment, the augmentation material comprises a barrier, mesh, scaffold, band or suture, or combinations thereof. In one embodiment, the first augmentation material and the second augmentation material are a single unit or opposing portions of a continuous construct. In other embodiments, they are separate pieces. In one embodiment, the lower bone engagement portion comprises a shaft, prong, plate or keel, or combinations thereof. In one embodiment, the anchors are driven into and along the vertebral endplate at an angle of about 0 to about 90 degrees, preferably about 0-20 degrees. The step of interconnecting the augmentation material comprises, in one embodiment, forming a band around the entire periphery of the endplate.

In another embodiment of the invention, a method of reconstructing or augmenting a vertebral endplate using a laterally deliverable curvilinear anchor is provided. In one embodiment, the method comprises providing an expandable frame comprising a distal connection site for connecting to the anchor and delivering a bone graft between two adjacent vertebral bodies. The method further comprises advancing the frame proximal to the graft and expanding the frame to retain the graft. The method further comprises advancing the curvilinear anchor between the vertebral bodies proximate to the frame along a first axis and coupling the frame to the anchor. The method further comprises driving the curvilinear anchor into an endplate of one of the vertebral bodies in an arc such that the head of the anchor is roughly perpendicular to the first axis and at least partially extends above the endplate, thereby reconstructing or augmenting the endplate. In several embodiments, an interbody spacer or other device is used instead of or in addition to the bone graft. In one embodiment, the anchor is delivered from a posterior approach across the vertebral endplate and driven into an anterior portion of the vertebral endplate.

In yet another embodiment of the invention, a method of attaching an anchor to a vertebral body endplate is provided. In one embodiment, the method comprises (a) providing an anchor comprising an upper attachment site connected to lower keel member; (b) wherein the keel comprises a leading edge connected to a lower screw coupling member; (c) driving a portion of the screw coupling member into an outer surface of the vertebral body; (d) driving a portion of the leading edge of the keel member into the vertebral body; (e) driving a portion of the upper attachment site across the vertebral endplate; wherein steps (c), (d) and (e) are performed simultaneously. The method further comprises driving a screw into an outer surface of the vertebral body; and coupling the screw with the screw coupling member. The implant may comprise anulus and/or nucleus augmentation material, or combinations thereof.

In one embodiment, a method of attaching an anchor to a vertebral body endplate further comprises forming a pilot hole in an outer surface of a vertebral body, aligning the screw coupling member with the hole, and driving the anchor into the vertebral body. In one embodiment, the method comprises attaching an implant to the upper attachment site of the anchor.

In one embodiment, a method of closing a defect between opposing vertebral endplates is provided. In several embodiments, a duckbill-type device is used. In one embodiment, the method comprises attaching a first gate member to a superior endplate and attaching a second gate member to an inferior endplate. Both gates have a proximal and distal end. The proximal end of the first gate is coupled to the superior endplate. The distal end of the first gate extends medially into an intervertebral disc space. The proximal end of the second gate is coupled to the inferior endplate. The distal end of the second gate extends medially into the intervertebral disc space. The method further comprises contacting the distal ends of the first and second gates to close a defect between opposing endplates.

In one embodiment, the first and second gates have a length greater than the distance spanning the opposing endplates at maximum distraction. In one embodiment, the first and second gates comprise flexible plates having a curved bias about a portion of the distance between their proximal an distal ends. In another embodiment, the first and second gates are at least partially concave. In one embodiment, the gates are multi faceted. In another embodiment, the distal ends of the gates form an angle between about 0 to about 180 degrees.

In one embodiment of the invention, a bone anchor for insertion into a first surface of a bone and along an adjacent second surface of said bone is provided. In one embodiment, the anchor comprises a neck having a length defined by a sharpened leading edge and a trailing end. The neck comprises an attachment site along at least a portion of its length. The neck also comprises a bottom portion terminating in two or more keels. A single keel may also be used in some embodiments. The keels are configured for pull-out resistance and stability by presenting a larger surface area below or embedded within said second surface of the bone relative to said neck. The keels form an angle from about 10 to about 180 degrees relative to each other. The keels comprises sharpened leading edges. The attachment site is offset relative to both the anchor's angle of insertion and said neck to present said attachment site along the second surface of said bone while said keels are inserted into said first surface. The sharpened leading edges of said keels are adapted to be driven into the first surface of the bone while simultaneously advancing the attachment site across said second surface. The attachment site is configured for coupling to a tissue or a prosthetic implant for repairing said bone or adjacent tissue. The anchor further comprises an arm extension rotatably or flexibly coupled to the neck along its length and terminates in at least one barb, hook, or angled projection, or combinations thereof. The bone anchor may be configured for use in the vertebral disc.

Although one anchor is provided in some embodiments, two, three, four, five, ten or more anchors are used in alternative embodiments. The anchor delivery tools and instruments described below may be used to deliver any of the anchors described herein.

BRIEF DESCRIPTION OF THE DRAWINGS

FIGS. 4A-E show a sequence involving loading an anchor into a delivery instrument and forcing it out of the lateral opening at the distal end of the delivery instrument according to one embodiment.

FIG. 15 shows a sagittal view of the implanted anchor in the previous figures.

FIG. 22A shows a perspective view of another embodiment of an anchor according to one or more embodiments having a three legged keel portion and designed such that only the attachment portion remains proud on the tissue surface. FIG. 22B shows a delivery tool for driving an anchor with a mated surface and alignment pins.

FIGS. 23A-B show a perspective view of another embodiment of an anchor according to one or more embodiments having a flexible linkage member.

FIGS. 24A-C show a series of perspective views of one embodiment of an anchor and barrier system according to one or more embodiments.

FIGS. 25A-C show a series of perspective views of another embodiment of an anchor and barrier system according to one or more embodiments.

FIGS. 29A-29F illustrate a plurality of lateral views of various embodiments of anchors and attachment positions and locations with respect to patient tissue.

FIG. 31A illustrates an embodiment of an anchor partially engaged with a support member.

FIG. 31B illustrates the embodiment of anchor and support member of FIG. 31A in a fully engaged configuration.

FIGS. 36A-36C illustrate embodiments of an anchor and attached gate member and respective fixation locations with respect to an inner and outer surface of an anulus fibrosus.

FIG. 37 illustrates an embodiment of an anchor and attached gate member having a plurality of interweaved fingers.

FIG. 39C illustrates schematic top views of various configurations of gate members including concave, multifaceted, and rounded.

FIG. 40A illustrates an embodiment of anchors and attached gate members, wherein opposing gate members are substantially mirror images of each other and positioned in substantial alignment.

FIG. 40B illustrates an embodiment of anchors and attached gate members, wherein opposing gate members engage such that one gate member at least partially nests within the opposite gate member.

FIG. 41 illustrates an embodiment of anchors and attached gate members wherein opposed gate members are connected by an embodiment of a connector.

FIGS. 42A and 42B illustrate side and end views respectively of embodiments of first and second anchor structures.

FIGS. 43A-43D illustrate one embodiment of an implantation sequence of the embodiments of first and second anchor structures of FIGS. 42A and 42B.

FIGS. 44A and 44B illustrates a side view of another embodiment of first and second anchor structures.

FIGS. 45A-45C illustrate one embodiment of an implantation sequence of the embodiment of first and second anchor structures of FIG. 44.

FIGS. 46A and 46B illustrate perspective and side views respectively of an embodiment of a support implant.

FIGS. 47A and 47B illustrate an anterior posterior view and lateral view respectively of an embodiment of a support implant provided with a plurality of markers configured to indicate a configuration of the support implant at an implantation location.

FIG. 48 and Detail A are a schematic side view of an embodiment of a support implant including an anchor and a moveable support structure attached thereto.

FIGS. 50A-50E illustrate one embodiment of an implantation sequence utilizing embodiments of the delivery tool of FIG. 49.

FIG. 51 illustrates an embodiment of delivery tool and attached support implant defining a plurality of adjacent locating surfaces configured for support and alignment with patient tissue.

FIGS. 55A and 55B illustrate embodiments of an implantable support anchor in an implanted side view and perspective view respectively.

FIGS. 57A and 57B illustrate perspective views of embodiments of implantable support anchor with a support structure and multiple keel members.

FIGS. 58A and 58B illustrate perspective views of further embodiments of implantable support anchors.

DETAILED DESCRIPTION

Embodiments relate generally to tissue anchors and methods of delivering tissue anchors to the intervertebral disc or other sites within the body. In some embodiments, the tissue anchors provide increased pull-out resistance, improved stability and/or increased contact with tissue involving a reduced amount of penetration. In some embodiments, delivery methods are minimally invasive and include, but are not limited to, linear, lateral, and off-angle implantation or driving of anchors along, against or within tissue surfaces. In several preferred embodiments, bone anchors are provided.

The term "anchor" as used herein shall be given its ordinary meaning and shall also include, but not be limited to, nails, staples, screws, fasteners, sutures, spikes, tacks, keys, pegs, rivets, spikes, bolts, and pins. In several embodiments, the anchor comprises one or more tines or prongs. In one embodiment, the anchor is forked. In some embodiments, the anchor may be straight, curved, or partially curved.

In several embodiments, the anchors disclosed herein are particularly suited for hard tissues such as bone. In other embodiments, soft tissue anchors are provided. One or more embodiments of the anchor can be delivered into a tissue and be secured within said tissue and resist extraction, migration, and/or rotation. Such stability is especially important in environments like the spine, where the anchor is adjacent delicate nerve tissue such as the spinal cord. However, in several embodiments, the anchoring system may be used in other delicate vasculature such as the aorta.

Although several examples of sites appropriate for anchors are described herein for use in the boney tissue of the spine and particularly the vertebral endplates, anchors according to the embodiments described herein have broad applications. For example, the anchors described herein may be used in the radial head, ulnar head, humeral head, tibial plateau, scapula, acromion, talus, malleolus, tendons and ligaments such as the talo-fibular ligament, anterior cruciate ligament, patella tibial tendon, Achilles tendon, rotator cuff, and other tissues such as the meniscus. Further, anchors according to one or more embodiments can be disposed within artificial tissues and/or prosthetics.

Figure 1A:
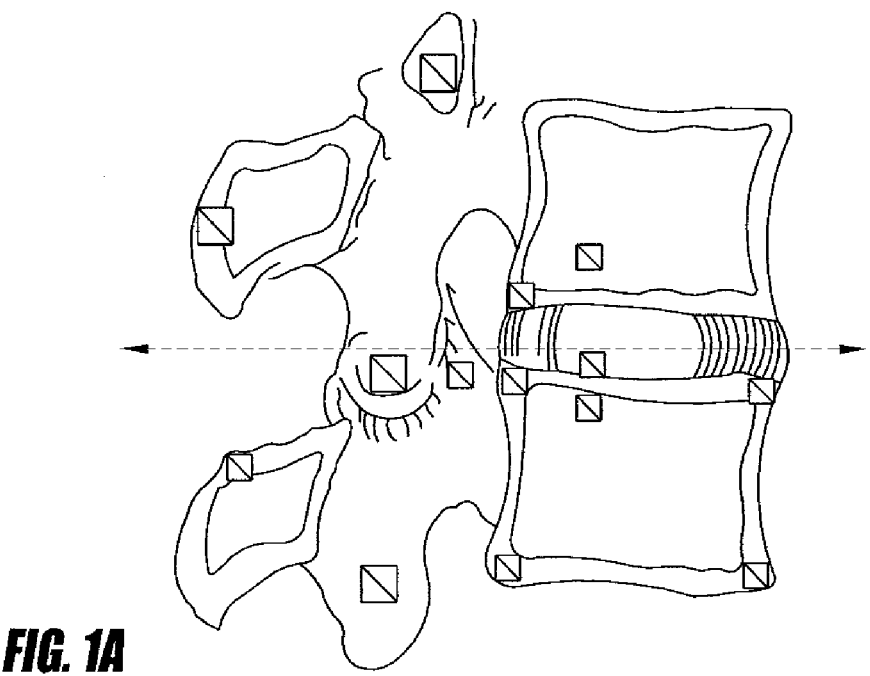
FIGS. 1A-B show an axial and sagittal view respectively of a spine segment and various anchor sites.
Figure 1B:
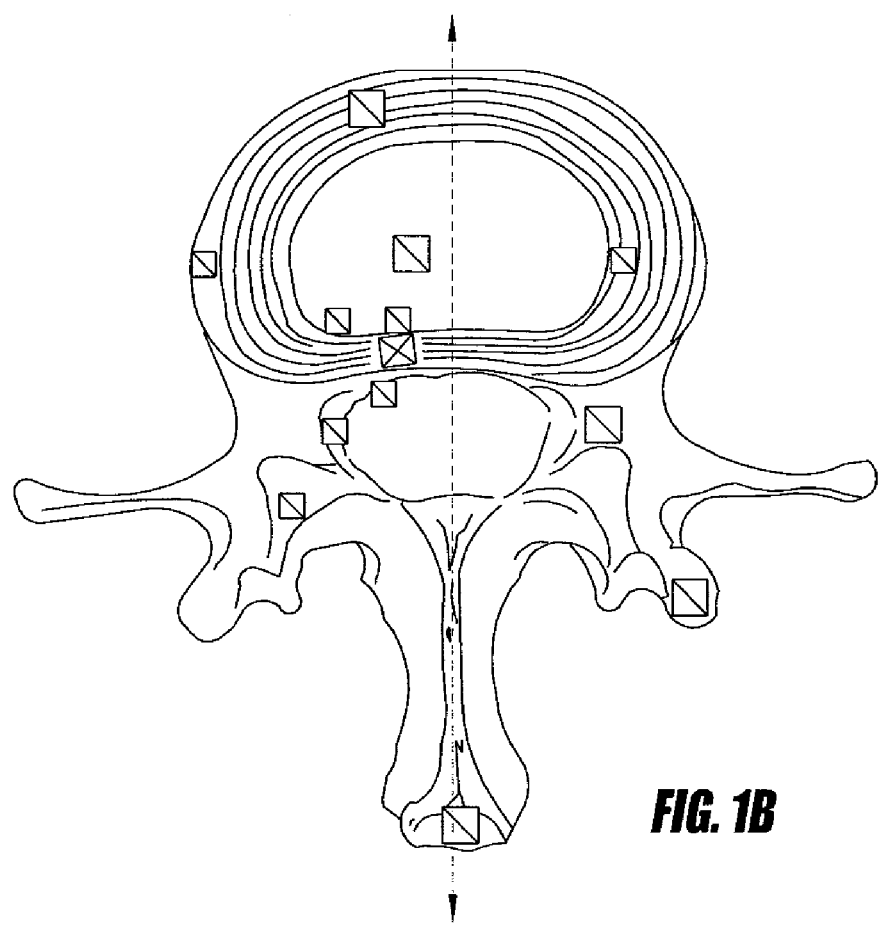

FIG. 1A provides a sagittal view of a spine segment. Also shown are numerous potential anchor sites and are marked as "X." FIG. 1B is an axial view of the same spine segment and shows other possible anchoring sites including along or within a vertebral body, endplate, transverse process, spinous process, facet, and pedicle. In other embodiments, an anchor can be placed along the cortical rim of the endplate or medially within the cancellous bone or relative to or within a pedicle, skull, or sacrum. Other anchoring sites include, but are not limited to: relative to a defect within the disc either in the area of the defect, at the interface of the anulus and nucleus or in the area of the nucleus.

In several embodiments, one or more anchors are used in connection with an anulus or nucleus augmentative device, as described in U.S. Pat. Nos. 6,425,919; 6,482,235; 6,508,839; and 6,821,276, all herein incorporated by reference. In one embodiment, one or more anchors are used to anchor an anulus augmentation device that is placed within or beyond a defect in the anulus to the vertebral endplates.

One or more embodiments comprise anchors or gates disclosed herein are made at least partially of one or more of the following materials: any biocompatible material, material of synthetic or natural origin, and material of a resorbable or non-resorbable nature. The anchor may also be partially or wholly constructed from material including, but not limited to, autograft, allograft or xenograft; tissue materials including soft tissues, connective tissues, demineralized bone matrix and combinations thereof; resorbable materials including polylactide, polyglycolide, tyrosine derived polycarbonate, polyanhydride, polyorthoester, polyphosphazene, calcium phosphate, hydroxyapatite, bioactive glass, collagen, albumin, fibrinogen and combinations thereof; and non-resorbable materials including polyethylene, polyester, polyvinyl alcohol, polyacrylonitrile, polyamide, polytetrafluorethylene, polyparaphenylene terephthalamide, cellulose, and combinations thereof. Further examples of non-resorbable materials include carbon-reinforced polymer composites, shape memory alloys, titanium, titanium alloys, cobalt chrome alloys, stainless steel, and combinations thereof. In some embodiments, the anchor comprises titanium alloys or cobalt chrome.

In several embodiments, the anchor comprises an anchor body and an anchor attachment site. In one embodiment, the anchor attachment site is adapted to accept or connect to a suture, linkage element, threaded screw, and/or provides a surface for ingrowth into an adjacent structure. The anchor attachment site can be integral to the anchor or a separate structure comprised of the same or different material as the anchor body. The anchor attachment site can be coupled to the anchor body. For example, the anchor attachment site can be flexibly, rigidly, or rotationally connected to the anchor body.

The anchor attachment site can comprise one or more of the following structures: head, flange, plate, disc, protrusion, channel, hole, cleat or eye. These structures can be placed at various positions along the anchor. For example, one or more of these structures may be placed at or near the ends of the anchor, in the middle of the anchor, or at any other desired position. In some embodiments, the anchor attachment site comprises mesh, fabric, or membrane material, or a combination thereof. The site may be parallel, perpendicular or angled with respect to the body of the anchor. In one embodiment, the anchor attachment site is located on an end or terminus of the anchor body.

In one embodiment, the anchor comprises one anchor body and one anchor attachment site. In another body, the anchor comprises one or more anchor bodies and one or more anchor attachment sites. In one embodiment, the anchor comprises one body and two attachment sites.

In one embodiment, at least a portion of the anchor or gate comprises a biologically active or therapeutic agent. For example, in some embodiments, at least a portion of the anchor can comprise growth factors such as bone morphogenic proteins, insulin-like growth factor 1, platelet derived growth factor, and fibroblast growth factor. In one embodiment, both the anchor body and anchor attachment portion of the anchor can be adapted to deliver a biologically active or therapeutic agent. In other embodiments, at least a portion of the anchor is coated with a biologically active or therapeutic agent.

Curvilinear Anchor

Anchors (including staples, nails, and other fastening or joining devices) according to one or more embodiments can be partially or wholly arcuate or curvilinear. The radius of curvature (the tightness or gentleness of the curve) can vary among embodiments as can the section of a circle corresponding to the anchor. For example, an anchor having a 90 degree curve would appear as ¼ of a circle. Other ranges of curves between 0-180 degrees are also possible. In some embodiments, for example, the curvature is about 15, 30, 45, 60, 75, 90, 120, 150, or 180 degrees.

An anchor can also be at least partially curved with a linear portion extending upward. In this embodiment the curved portion is adapted for driving into a tissue and the straight portion remains proud, or above the surface. Depending upon how the anchor is driven into the surface, the proud portion of the anchor can be anywhere from 0-180 degrees relative to the surface. The curvature of an embodiment of the anchor can also be variable along the anchor. Such a variable curvature could be employed to increase or decrease pressure on tissues adjacent to the anchor. In one embodiment, the proud portion is about 15, 30, 45, 60, 75, 90, 120, 150, or 180 degrees relative to the surface.

The surface or body of the anchor can be roughened, porous, barbed, lubricated, coated or impregnated with a biologically active or therapeutic agent. The anchor can be in the form of a curved nail or staple with a crown or bridge and having two or more prongs or legs extending therefrom. A slot or gap between the prongs in one or more embodiments of a staple can be aimed at a suture or other structure already implanted in or along a surface and then hammered in place thereby anchoring the suture in place. The tips of the prongs of a staple can be beveled to effect a wedging action. By beveling or angling the inner, outer, front, and/or back of a prong tip, the prong will tend to travel in a particular direction. Moreover, the beveled tips can complement each other, work in opposition, or some combination thereof. In one embodiment the prong tips are beveled on the outside edge, in another embodiment the tips are beveled on the inside edge. In yet another embodiment, the top of one prong is beveled and the bottom of another is beveled. In addition, the cross section of prongs may be variable along the length of the anchor. In one embodiment, the anchor prong's smallest cross section is at or near the tip and at its greatest furthest from the tip, creating a wedge along the curve of the anchor. This may aid in increasing compression on all or part of the bone or other tissue in contact with the anchor.

In another embodiment, an anchor can be resiliently flexible such that after passing through a curved slot or deflecting surface of the delivery device, the anchor (including staples, nails, etc) straightens out to its original shape as it is advanced out of the device and into the tissue. The original shape, predetermined shape, first shape, or unrestrained shape can be, for example, straight, angled, corkscrew, or offset. The prongs or legs of one or more embodiments of the anchor, such as, for example, a staple, can be straight, curved, angled, corkscrew, or offset with respect to each other.

Anchor Delivery Tool

Figure 2:
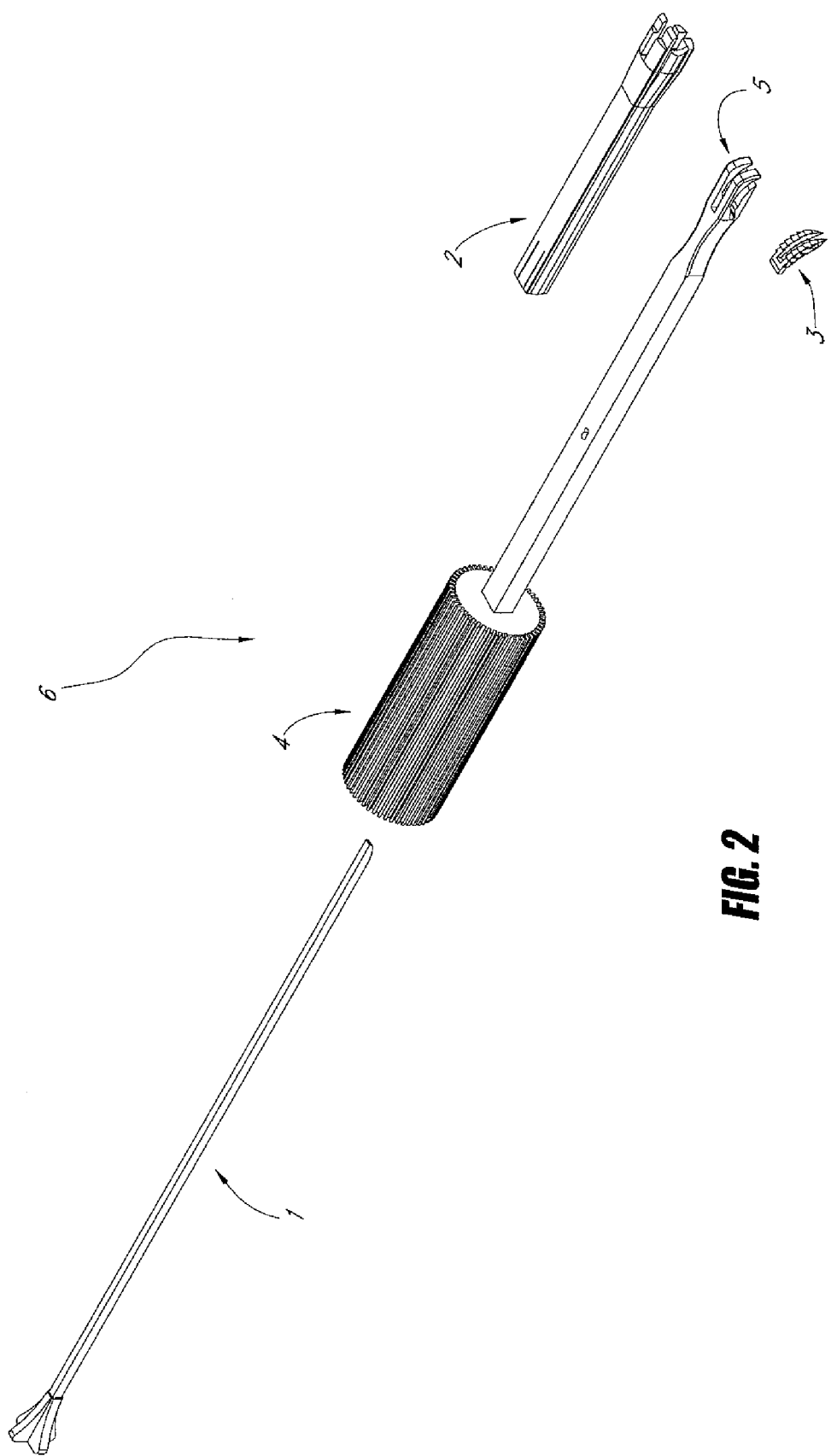
FIG. 2 shows an exploded view of one embodiment of a curvilinear anchor and delivery instrument.

Turning now to FIG. 2, shown is one embodiment of an anchor 3 and delivery instrument 6 according to one or more aspects of the invention. A guide body 4 has a cylindrical grip or hand hold and first proximal and second distal end. The body 4 can be partially or fully hollow and contain a guide way chamber 5 for holding and orienting an anchor or staple 3 terminating in an opening at the distal end of the guide body. The opening can be oriented axially out of the front of the body or laterally and side mounted. The guide way chamber 5 comprises a curved or angled slot or passage and opens perpendicular or off angle (or between 0-180) with respect to the long axis of the guiding body. The radius of curvature along the passage can be constant or variable along the sweep of the curve. A curved nail or staple 3 can be inserted within the chamber 5 via a side loading window. A pusher rod 1 is carried within or by the body 4 and accesses or is in communication with the guide way chamber. The rod 1 has a first proximal end that can be configured with a head or striking surface for hammering and a second distal end for transmitting force to the end of a nail, staple, or anchor 3 within the guide way chamber 5. The distal end or anvil can be curved, beveled, or angled such that the linear force of the rod can be transmitted downward or along an arc as the staple 3 is driven out through the curved slot of the chamber 5. The rod 1 may be rigid or at least partially flexible in construction.

Also shown in FIG. 2 is a depth stop support 2 which can be configured as a snap on sleeve that fits over the body 4. In other embodiments a depth stop may simply be a projection off of the body that limits further travel of the body and/or guide way chamber opening within or adjacent a tissue. The depth stop may also be adjustable to allow for different implantation depths or locations. The depth stop may project in one or more directions from the long axis of the tool. Depth stops and other instrumentation described in U.S. Pat. No. 6,821,276, herein incorporated by reference, may be incorporated in several embodiments.

Figure 3:
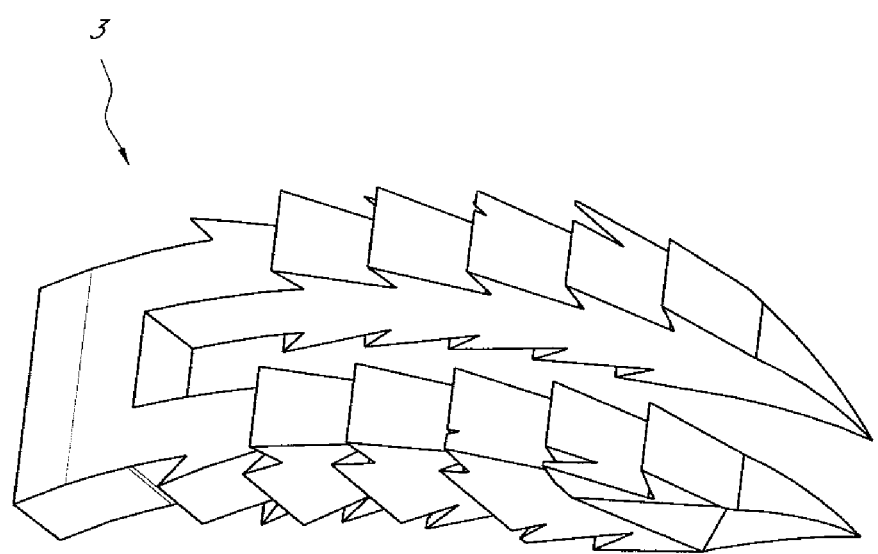
FIG. 3 shows a perspective view of one embodiment of a curved two pronged staple type anchor.
Figure 4A:
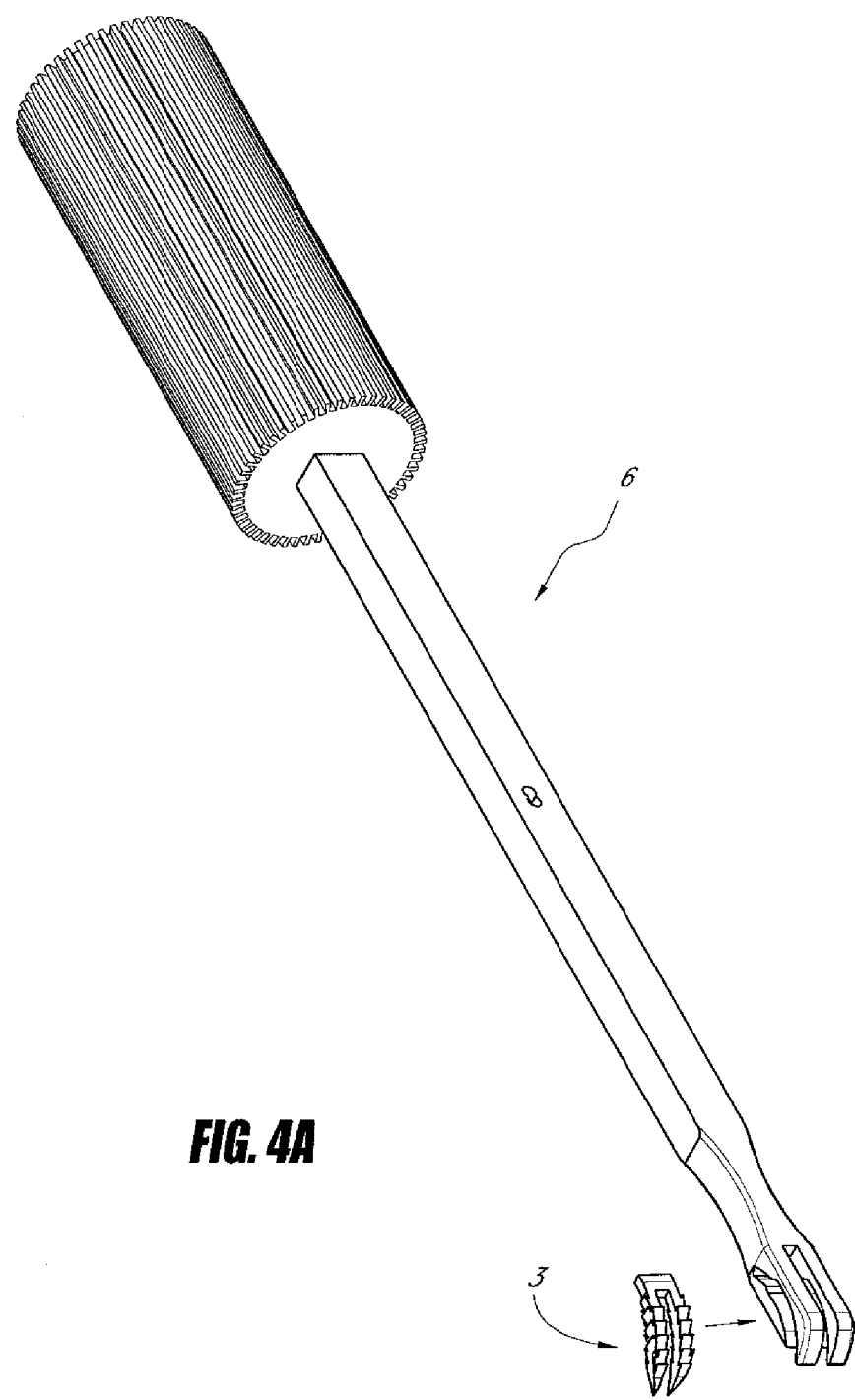
Figure 4C:
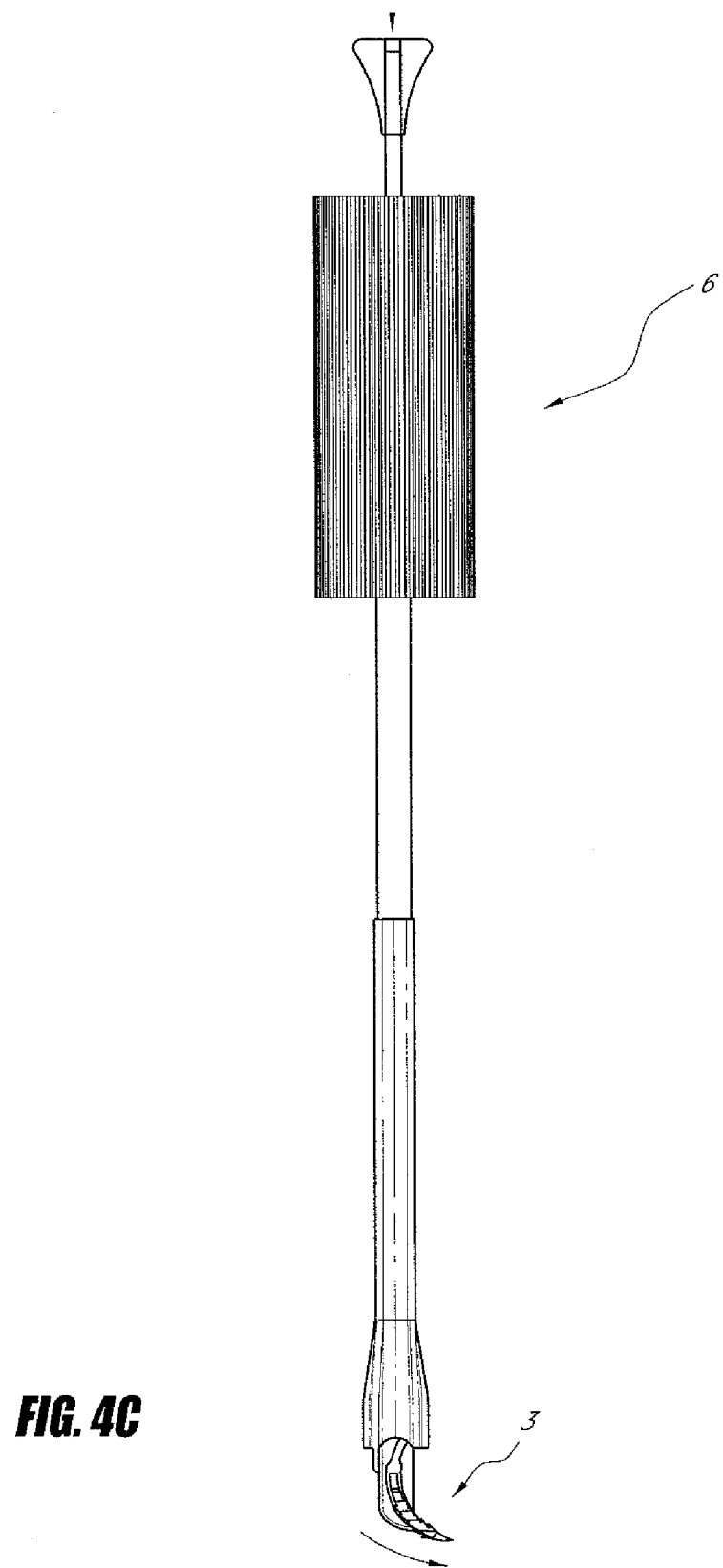
Figure 4D:
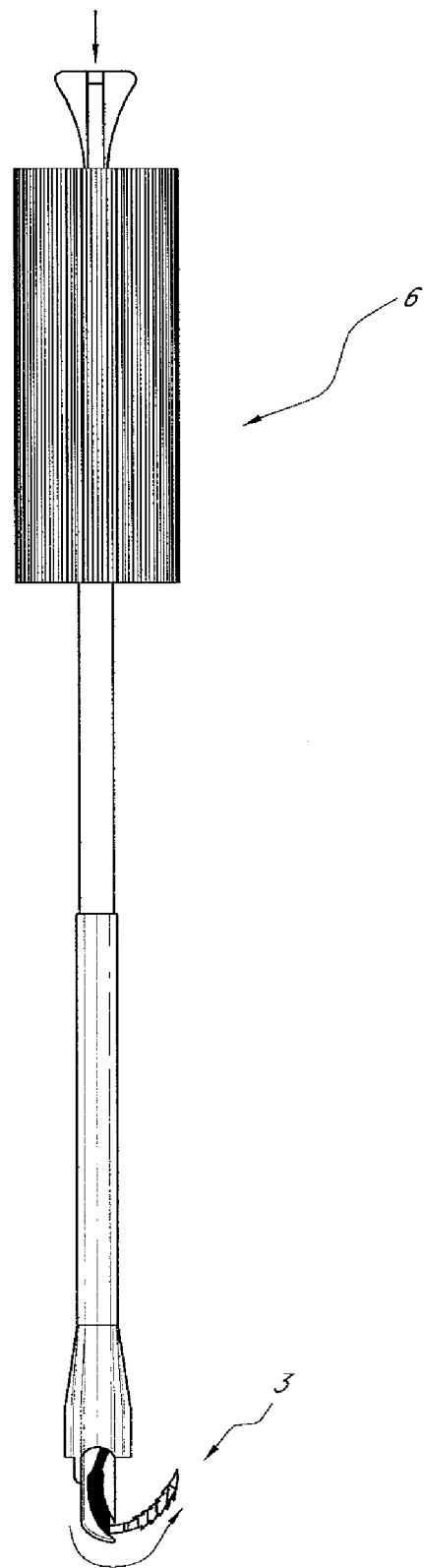
Figure 4E:
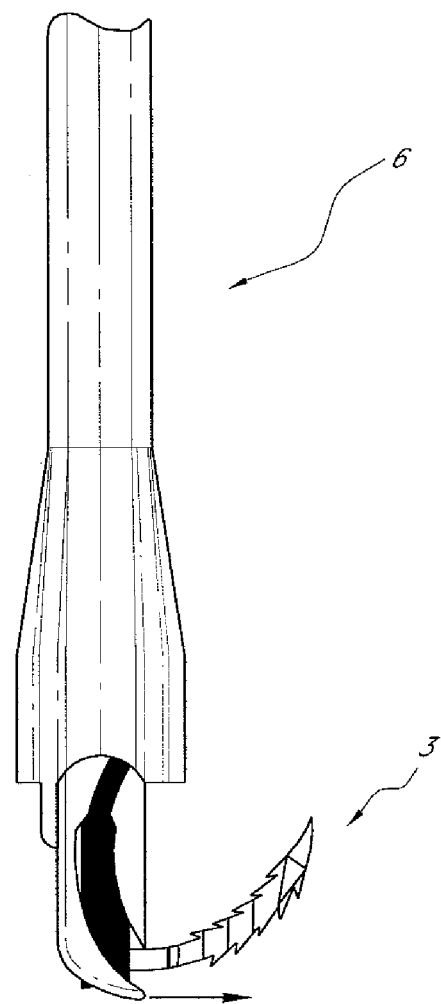

FIG. 3 is an example of an embodiment of a staple or anchor 3 with two prongs or legs that are barbed and beveled on the outside. When the staple is driven into a surface such as a bone the prongs may or may not bend inward or be wedged together. This action will pinch and compress the bone tissue between the prongs while pressing outwardly against the sidewalls of the bone facilitating a stable anchorage.

The series depicted in FIGS. 4A-E shows an embodiment of a delivery device 6 being loaded with an anchor 3 and the push rod applying force to the anchor and partially driving it out of the curved guide way chamber opening or lateral opening. FIG. 4 B also shows the depth stop support sleeve 2 with a vertical slot corresponding to the guiding body distal slot which is aligned with the midline of the anchor and can be used to precisely implant or drive the anchor or staple around a suture or linear structure.

Figure 5:
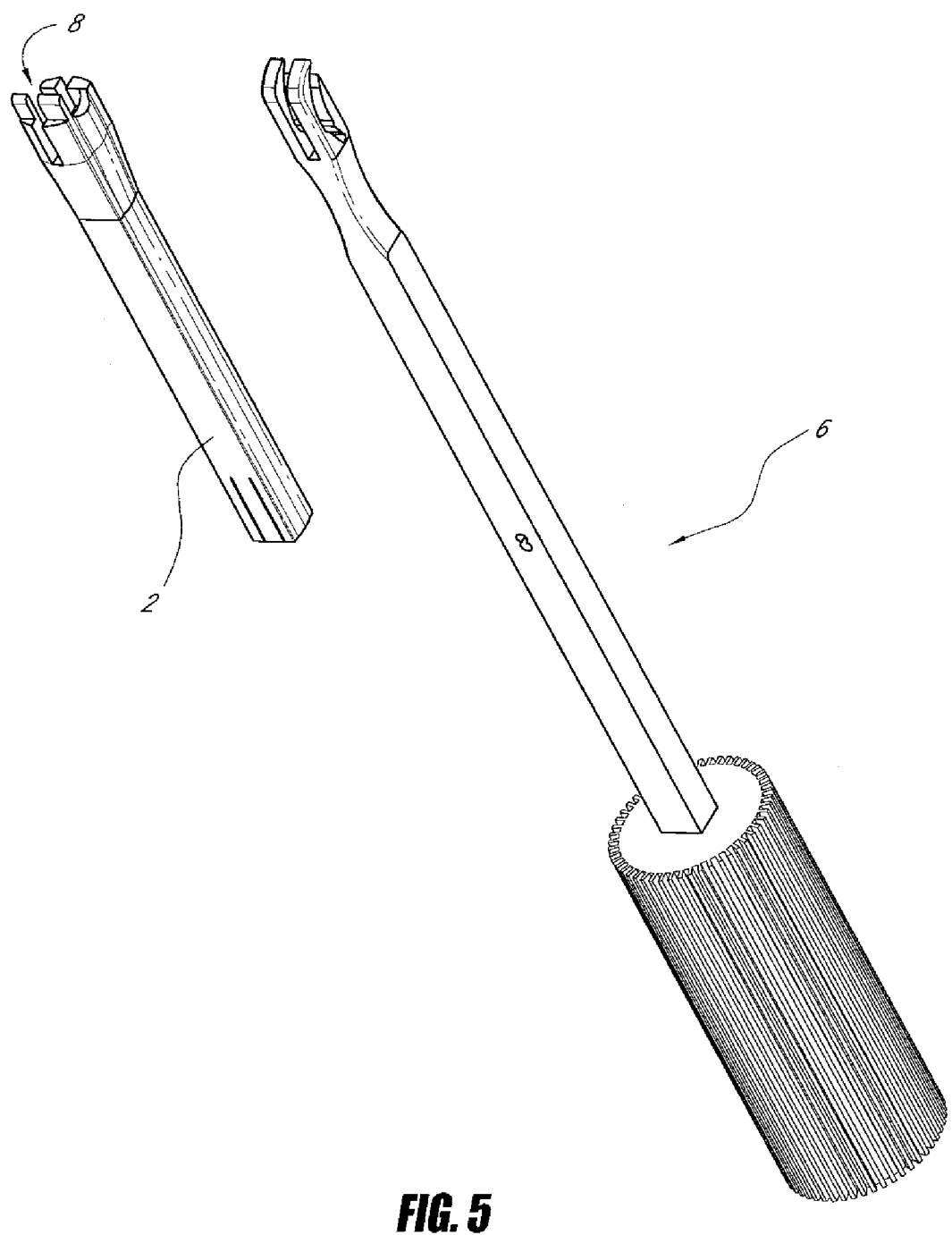
FIG. 5 shows an exploded view of one embodiment of a delivery instrument and detachable sleeve.

In FIG. 5, an embodiment of the depth stop support is shown as an attachable sleeve that fits on or over the distal end of the guiding body. However, many of the features of the sleeve can be machined, welded or attached directly to the body if so desired. In addition to the vertical slot corresponding to the guiding body distal slot and adjustable depth stop, an alignment projection 8 is shown. The alignment projection can form a right angle with the depth stop and have a beveled tip to ease insertion. The alignment tip can be a relatively flat and rectangular projection that in use can be rotated and rocked between to vertebrae or a hole in an anulus to distract the vertebrae. Upon partial or full distraction the tip and at least part of the guiding body can be inserted between the adjacent vertebral bodies. The depth stop can limit the amount of insertion by catching the edge of one or both of the opposing vertebral endplates. Vertebral taxis or the resistance of the anulus and endplates to further distraction can serve to immobilize the guiding body as the anchor is hammered out. Alternatively the body can be wedged along an inferior superior plane to drive the opening of the guide way chamber against the desired anchor site. In another embodiment one or more depth stop surfaces may contain one or more barbs, spikes, nails, fasteners, or means for engaging or immovably coupling the distal end of the body to a boney structure such as a vertebral body. In one embodiment an upper depth stop surface may be configured to engage a superior vertebral body and a lower depth stop surface may be configured to engage an inferior vertebral body.

Although the push rod and hammering method described infra is a preferred method of delivery other methods and devices can be used for this purpose. For example, compressed gas and hydraulics can be utilized for driving. The push rod can be configured as a piston or threaded rod (that can be rotated to expel the implant) for imparting linear force. Also, the threaded rod or piston can be flexible or have joints along its length to accommodate a curved or flexible guiding body.

Delivery instruments and devices according to one or more embodiments can also be used to implant other devices besides anchors and the like. For example, a prosthetic device (including, but not limited to, a barrier, mesh, patch, or collapsible implant) can be attached or coupled to an anchor according to several embodiments of the present invention, such as described in U.S. Pat. Nos. 6,425,919; 6,482,235; and 6,508,839; 6,821,276, all herein incorporated by reference. In several embodiments, the prosthetic device can be loaded within or along the guiding body of the device. The anchor and the prosthetic device may be constructed from identical, similar, or different materials. The anchor and prosthetic device may be coupled or removably or reversibly. Connections between the anchor and the prosthetic device may be temporary (such as restorable or dissolvable sutures) or permanent. Instead of a prosthetic device that is coupled or attached to the anchor, the prosthetic device may also be of unitary construct or integral with the anchor.

In one embodiment, an implant such as collapsible patch is coupled to the anchor and oriented along or within the guiding body such that as the anchor is passed through the guide way chamber slot in a downward direction the patch is extruded outwardly or parallel to the long axis of the body. The patch can be held within the body which can have linear slot adjacent the curved slot of the guide way chamber or alternatively the patch can be mounted around the guide way chamber while coupled to the anchor within the chamber. Also, the depth stop sleeve can also be used to compress and hold the patch in place.

In a further embodiment, one or more anchors can be delivered separately from one or more implants. In one embodiment, the implant is first delivered and positioned and then anchored in place. In another embodiment, the anchor is first established in the implantation site and then the implant is delivered and connected to the anchor.

Figure 6A:
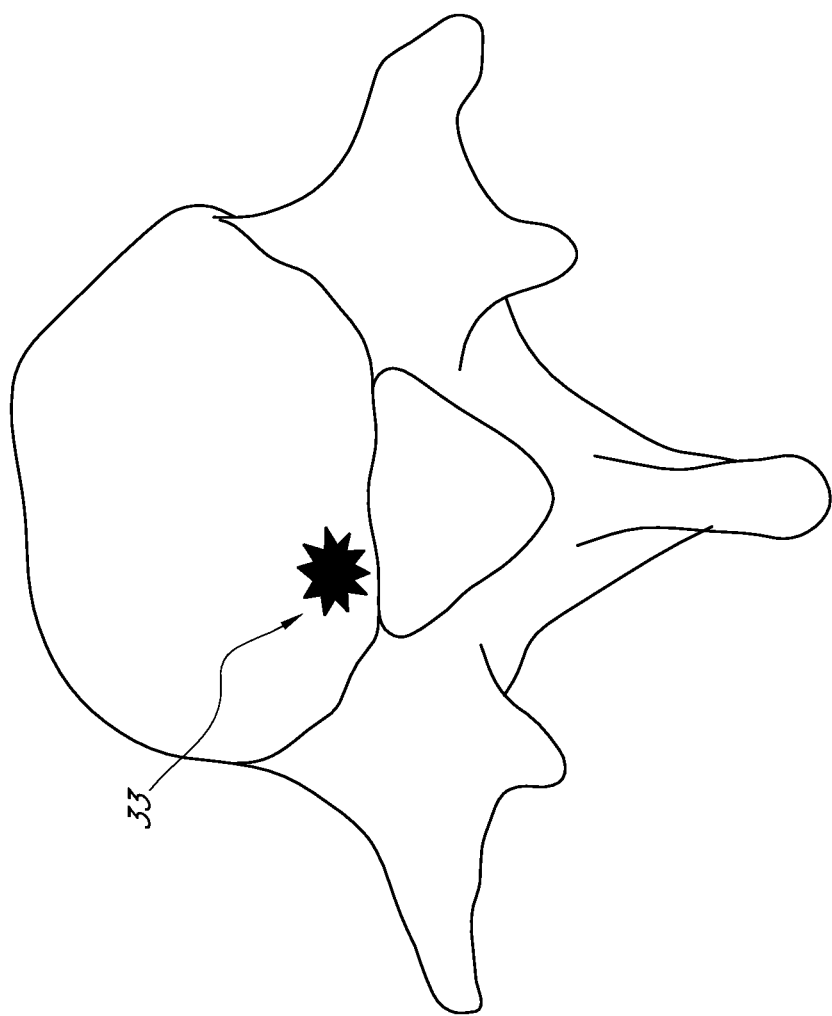
FIGS. 6A-G show a delivery sequence involving a vertebral endplate according to one embodiment.
Figure 6B:
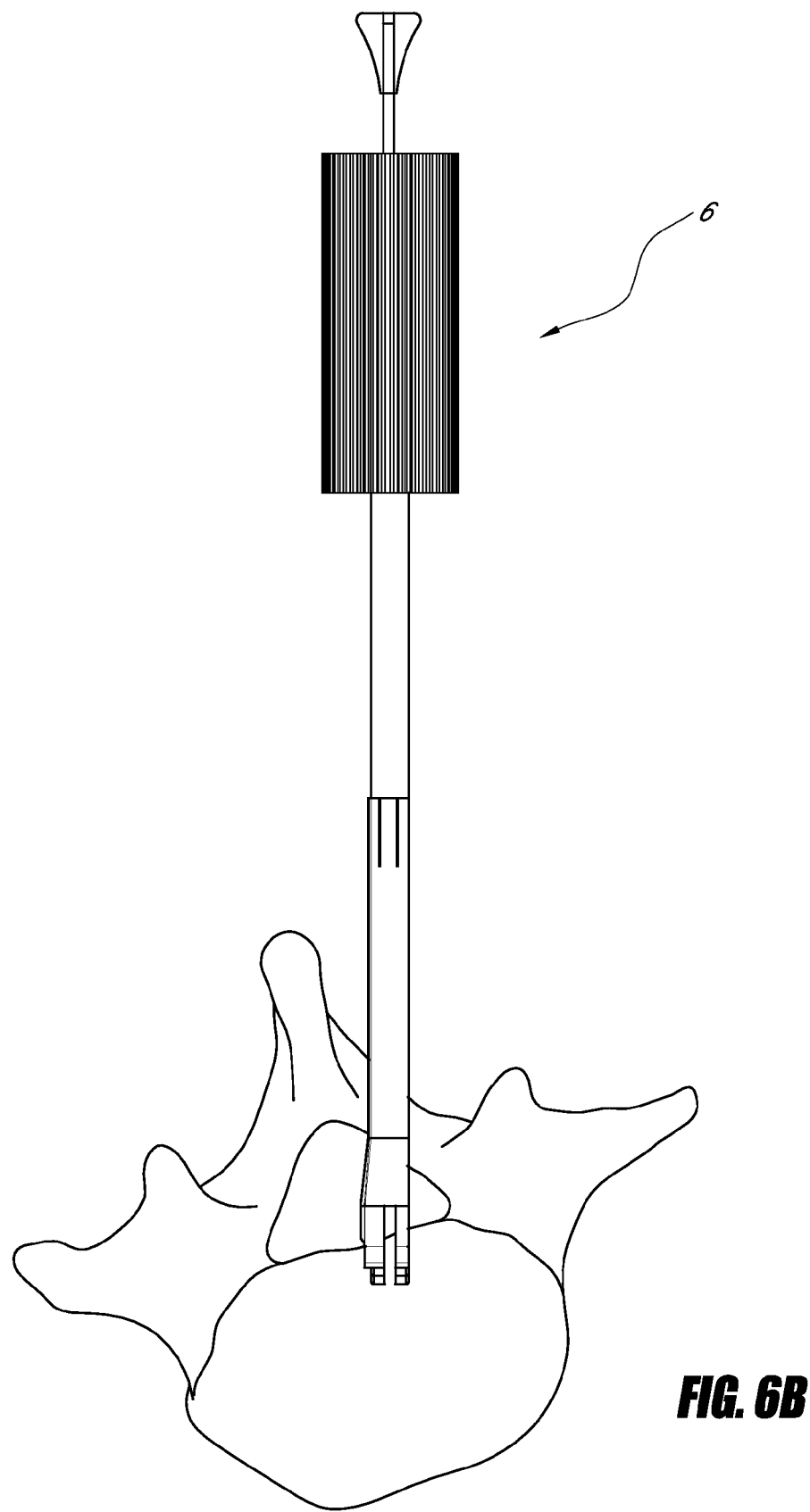
Figure 6C:
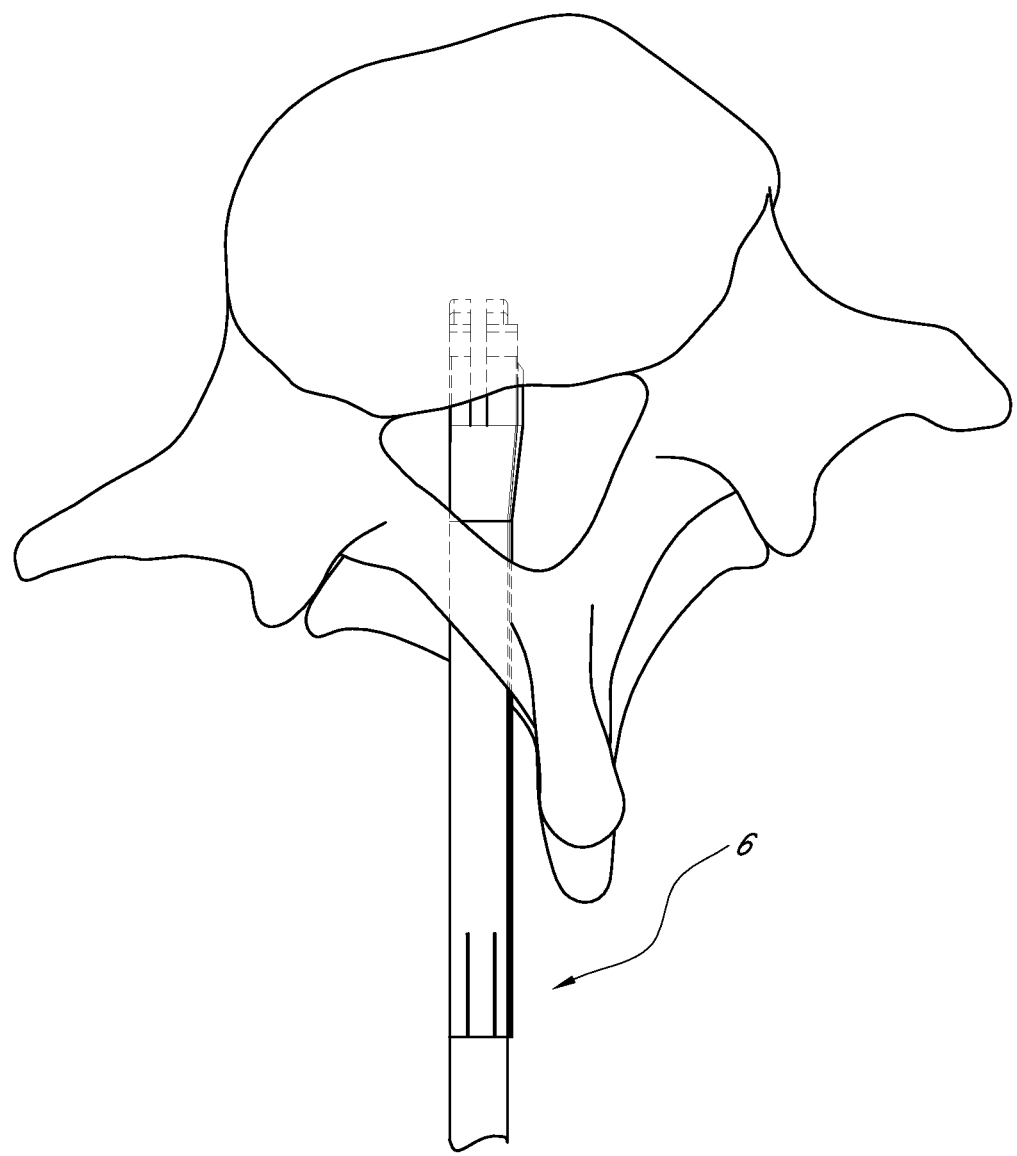
Figure 6D:
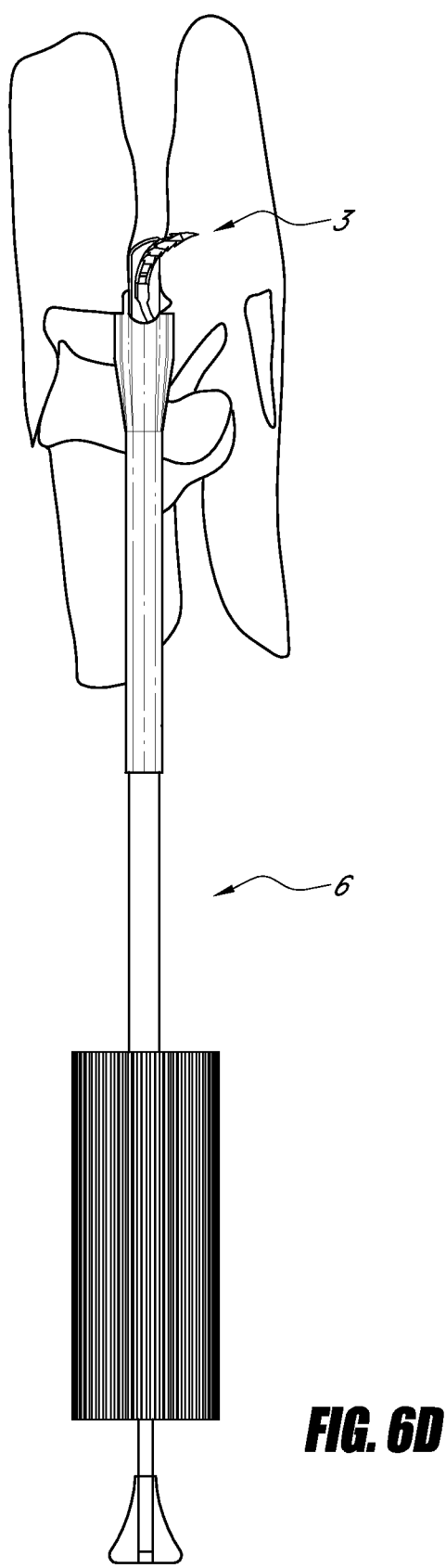
Figure 6E:
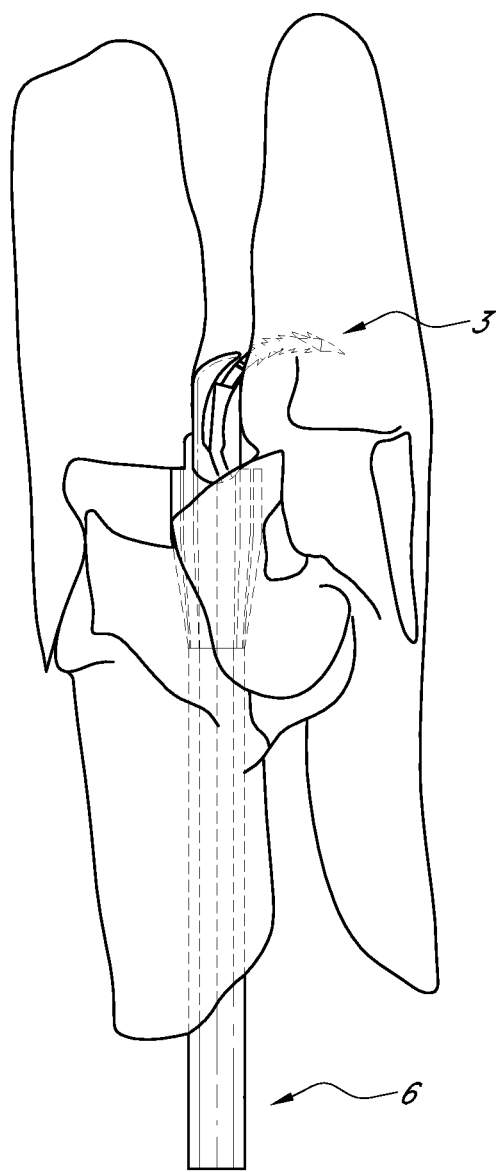
Figure 6F:
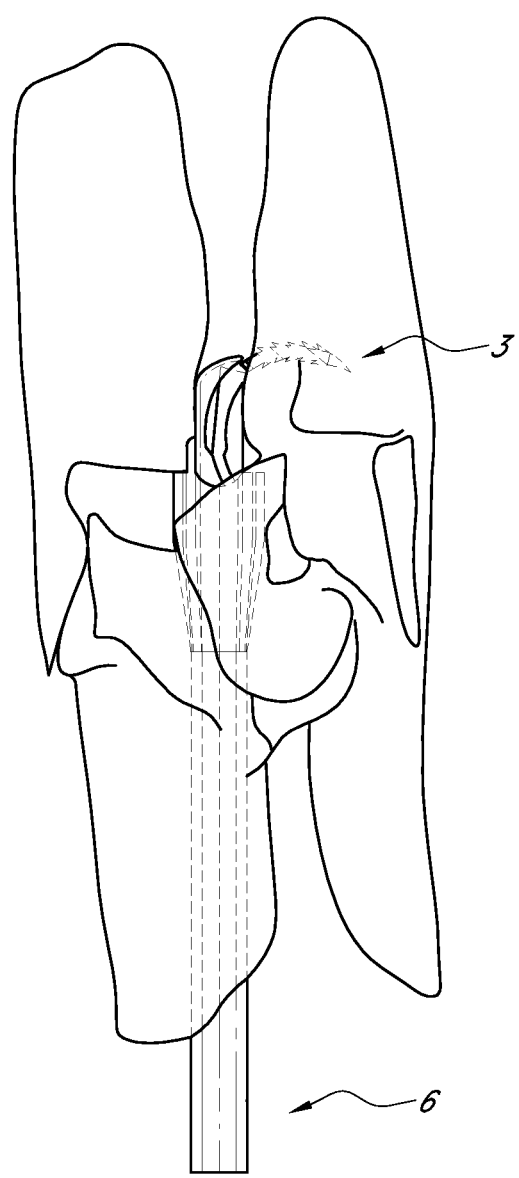
Figure 6G:
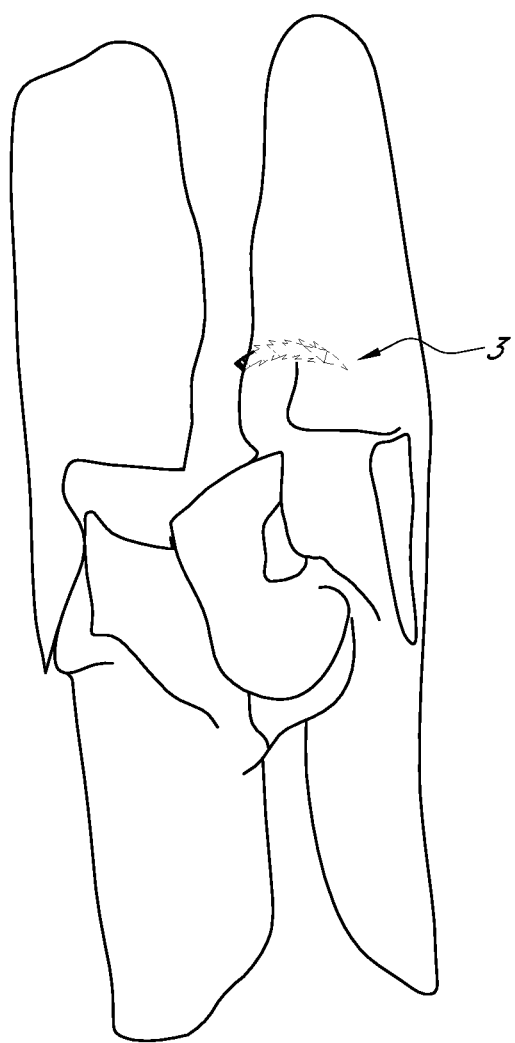

FIGS. 6A-L depicts an implantation sequence according to various embodiments. FIG. 6A is an axial cross section of a vertebral body, shown is a star shaped treatment zone along the vertebral endplate. The sequence shows an anchor being implanted into a posterior portion of a vertebral body along an endplate. The surface of the endplate can be accessed through a hole in the anulus. The hole in the anulus may be a naturally-occurring defect or surgically created. Methods and devices of the various embodiments are not limited to a single location along a vertebral body or surgical approach.

Perpendicularly Driven Anchor

Various embodiments of anchor presented herein are designed to improve upon the weaknesses in conventional bone screws and staples that are limited by surgical access and suture or anchor attachment site placement. For example, in the environment of the spine, the posterior elements of vertebral bodies forming facet joints, spinal canal, neural foramen, and the delicate nerve tissues of the spinal cord create numerous obstacles for surgery and diagnostic and interventional methods. Surgical approaches have been adapted to minimize damage to these structures and involve tight windows usually off angle to the target tissue.

Figure 7:
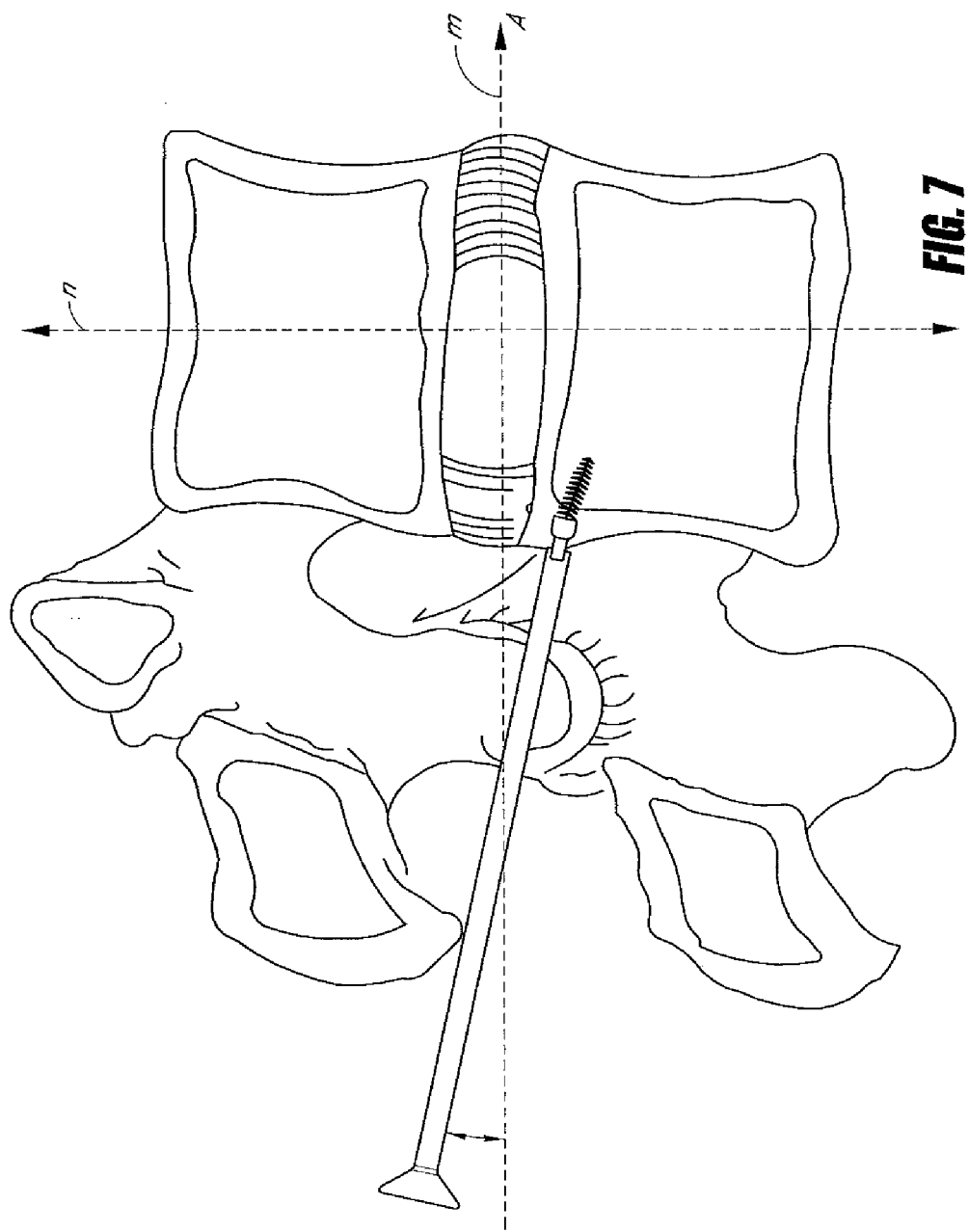
FIG. 7 shows a prior art bone screw and intervertebral anatomy.

An example of such prior art anchor and environment is depicted in FIG. 7, which shows a bone screw driven into a vertebral body from a posterior lateral approach. Here the anchor on the outside of the vertebral body is ineffective for retaining an implant within the disc and remains in dangerous proximity to the spinal cord. Several embodiments are particularly advantageous because the anchor does not present attachment sites originating at a proximal end in the axial orientation from which they are driven. Moreover, several embodiments are advantageous because the anchor is adapted with an expansion mechanism that provides a "mushrooming" effect, and thus the pull-out resistance is not merely limited to the friction and forces generated by the sidewalls of the material or tissue.

Several embodiments accommodate or exploit certain geometries or anatomical structures of the body. For example, in one embodiment, the attachment site of an anchor can be presented distally from the insertion site in a direction perpendicular or offset from the axial orientation of insertion. In one embodiment, the anchor presents a larger surface area below or embedded within a surface, thereby offering improved pull-out resistance without requiring an expansion or "mushrooming" step or mechanism.

In several embodiments, one or more anchors are driven into the surface of a first plane and present a portion on an adjacent plane or surface perpendicular or angled relative the first plane. Thus, the anchor is driven into a first surface and across an adjacent surface in the same instance. In one or more embodiments, at least a portion of the anchor such as the anchor attachment site is adapted to remain above or proud of the upper or second tissue surface or plane. With respect to the first surface (the front facing or lower surface into which the anchor is driven), the anchor can be driven in to a depth such that it is countersunk, left flush, or left partially external to the frontal tissue surface or plane. The anchor can also be delivered at a trajectory or angle relative to the second or top surface such that it is driven into the first surface and downwardly or upwardly across the second surface.

In several embodiments, the anchor is a flat plate-like nail or brad having a specialized keel portion and neck portion. In other embodiments the anchor is flat, plate-like, curved, corrugated, round, or a combination thereof. The neck can be terminated in a head or present an attachment portion along its length. The attachment portion or site can be comprised of a more flexible piece of fabric, wire, linkage, fastener component, hook eye, loop, or plate. The neck can be an extension, ridge, midline, or the apex of the keel portion. The neck can be oriented at the distal or proximal end of the keel or anywhere along its length. The neck can be the same length as, longer than, or shorter than the keel but preferably it is shorter. In one embodiment, the neck is a thin rod or beam. The keel portion can have a cross-section similar to a wedge, "V", "U", "T", and "W", "X", "O" and other shapes.

Anchors according to one or more embodiments have dimensions suitable to the implantation environment. For example, in one embodiment, the anchor has a height of about 0.2 cm to about 5 cm and a width of about 0.2 cm to about 5 cm. Anchors can have a length or depth from 0.2 cm to about 5 cm. In some embodiments, the length, width, height or depth can be less than 0.2 cm or greater than 5 cm. In one embodiment, the anchor has a length of about 1 cm and a width of about 0.5 cm. In yet another embodiment, the anchor has a length of about 0.5 cm and a width of about 0.25 cm. In another embodiment, the anchor is dimensioned as follows: about 0.3 cm wide, 1 cm long and 0.5 cm deep.

The length of the anchor can define a straight or curved line defined by a radius of curvature of about 0-90 degrees (e.g., about 15, 30, 45, 60, or 90 degrees). The keel, legs, extensions, blades, or fins can have a leading edge that is sharpened, left dull, or serrated. Other features of the neck and keel or extensions include, but are not limited to, barbs, tabs, roughened surface geometry, polished surface, coatings seeded carrier or drug eluting coatings or elements, concavities, scalloped ridges, grooves, "feet", ridges, voids, slots, and ingrowth openings are shown in the attached drawings. Secondary edges or ribs can protrude along portions of the keel to provide enhanced engagement with tissue. The neck or keel(s) can be hollow or tubular to accept tissue incorporation, cement, adhesive, therapeutic agents or another implant including a screw or pin. Portions of the keel or neck can further be expanded after implantation and/or portions of the neck or keel can be deflected or deployed as barbs after the anchor is initially implanted.

In addition to the neck and anchor attachment site, the anchor can also include an alignment means, engagement means or guide. Variations of the anchor alignment means can function to orient the anchor to a driver and couple it thereto. The anchor alignment means can comprise alignment components such as a protrusion, recess, or fastener component mated to a portion of a delivery instrument. The anchor engagement means can comprise engagement components or portions such as spikes, teeth, prongs, barbs, friction zones, or a combination thereof. The guide can comprise a protrusion, slot, arrow, tab, or a combination thereof. Thus, in some embodiments, the anchor comprises means to align, means to engage, means to guide, or a combination thereof.

Figure 8:
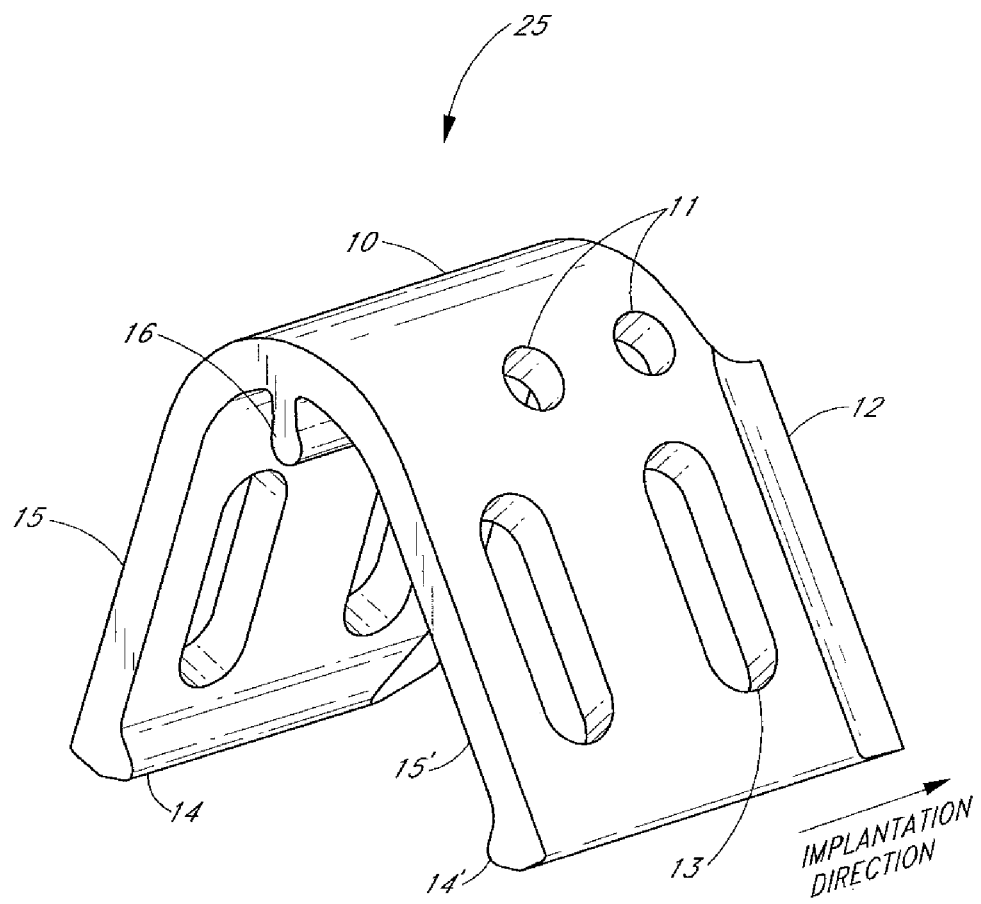
FIG. 8 shows an embodiment of an anchor according to one or more embodiments.

Turning to the drawings, FIG. 8 shows an embodiment of an anchor 25 with a leading edge 12, suture attachment sites 11, ingrowth features or voids 13, first and second plate-like legs or lateral extensions 15, 15' defining the keel, arcuate central ridge or apex 10, centering or alignment projection 16, and feet or ridges 14, 14'. Both the wedge-like shape of the keel portion of the implant i.e., the legs and the ridges or flange like extensions at the end of the legs function to hold the implant within a given tissue and to resist rotation and pull out from a variety of angles. The voids and ingrowth features serve to provide secondary stabilization over time and/or to allow chemical transfer or cellular respiration across the implantation site.

In a "V" shaped anchor or similar embodiment shown, the neck portion is bifurcated into two legs, extensions, blades, fins, or keels that meet at an apex and form an angle between about 10 and about 170 degrees. In one embodiment, the angle is about 30-90 degrees. The apex at the point of bifurcation can define a flat ridge or vertical extension or neck that can contain one or more anchor attachment sites. In a "U" shaped embodiment the neck can be in the form of an arc or eye projecting along the length of the body of the anchor. "V" or "U" shaped anchors can be modified to "L" shaped anchors in some embodiments.

Figure 9:
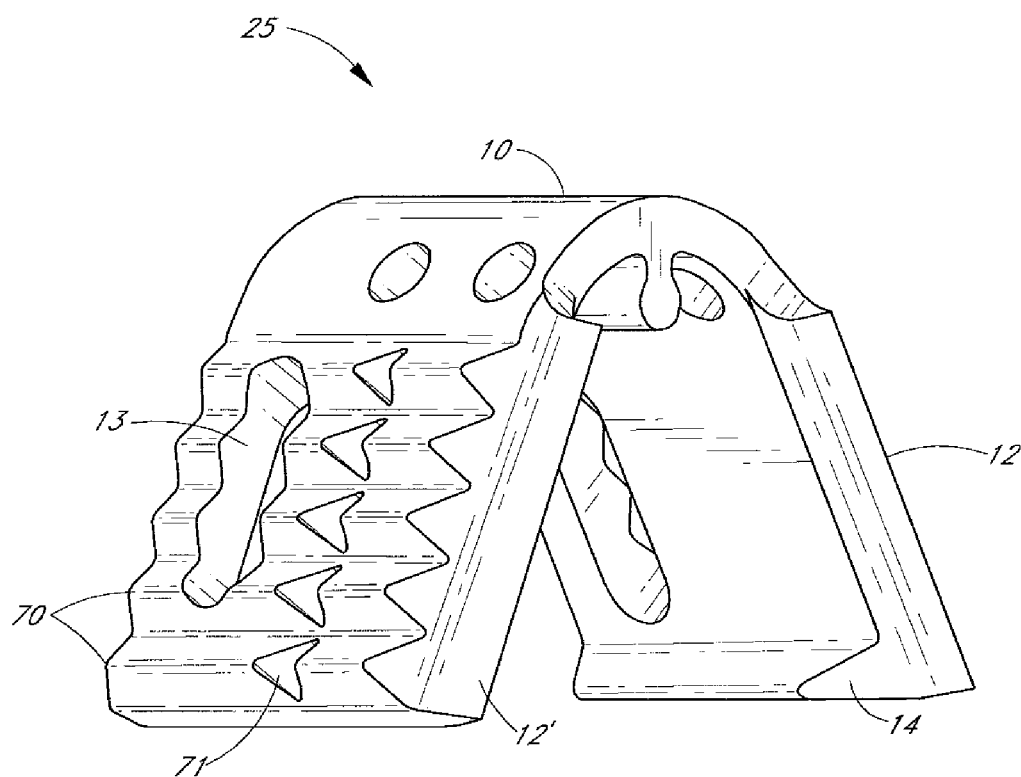
FIG. 9 shows another embodiment of an anchor according to one or more embodiments.

In FIG. 9, an anchor similar to the one depicted in the previous figure is shown. The apex 10, which would correspond to the neck in other embodiments, does not extend and instead presents a smooth curve which can present a less injurious profile to the anatomy in certain applications. Also shown are ridges 70 and scalloped teeth-like surface features 71.

Figure 10:
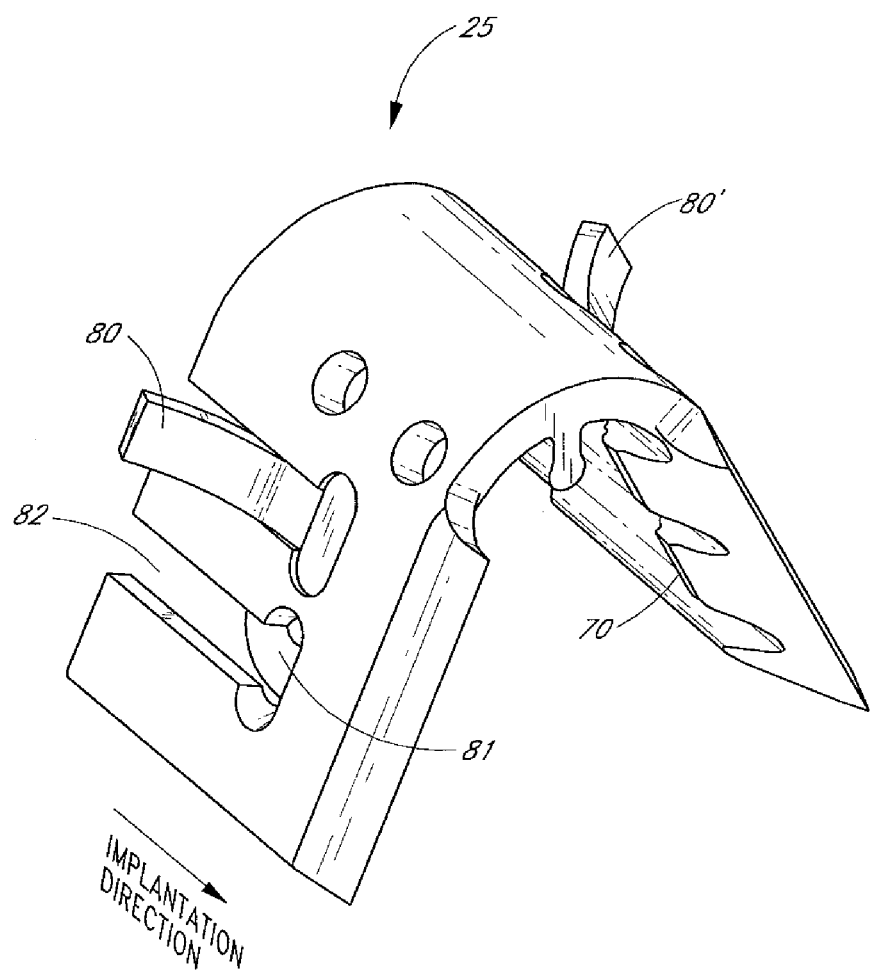
FIG. 10 shows another embodiment of an anchor according to one or more embodiments.

FIG. 10 shows another embodiment of an anchor with deployed barbs 80 and 80' These features can be held compressed within a sleeve on a delivery instrument or simply forced to compress inwardly as the implant is driven in to tissue. One or more slots or recesses 82 are adapted for holding the barbs during implantation to streamline the anchors profile.

One or more barbs can exert continuous outward pressure on the sidewalls of a tissue or expand to form a shelf or flange if the tissue geometry widens, expand or become more pliant. For example, in a vertebral body the implant might be driven into cortical bone and then further into cancellous bone. Upon reaching the cancellous bone, the barbs flexible plate-like structure or engagement means, can expand or extend outwards. In another example the anchor is driven at least partially into the hollow of a boney structure such that the barbs expand and engage the inner wall of the bone. Element 81 can be arranged as an opposing barb or expansion means however one or more barbs 80, 81 can be oriented relative to each other from 0-360 degrees. For example, the barbs or other barb-like components may be orientated relative to each other at the following angles: 15, 30, 45, 60, 90, 120, 150, 180, or 360 degrees.

Figure 11:
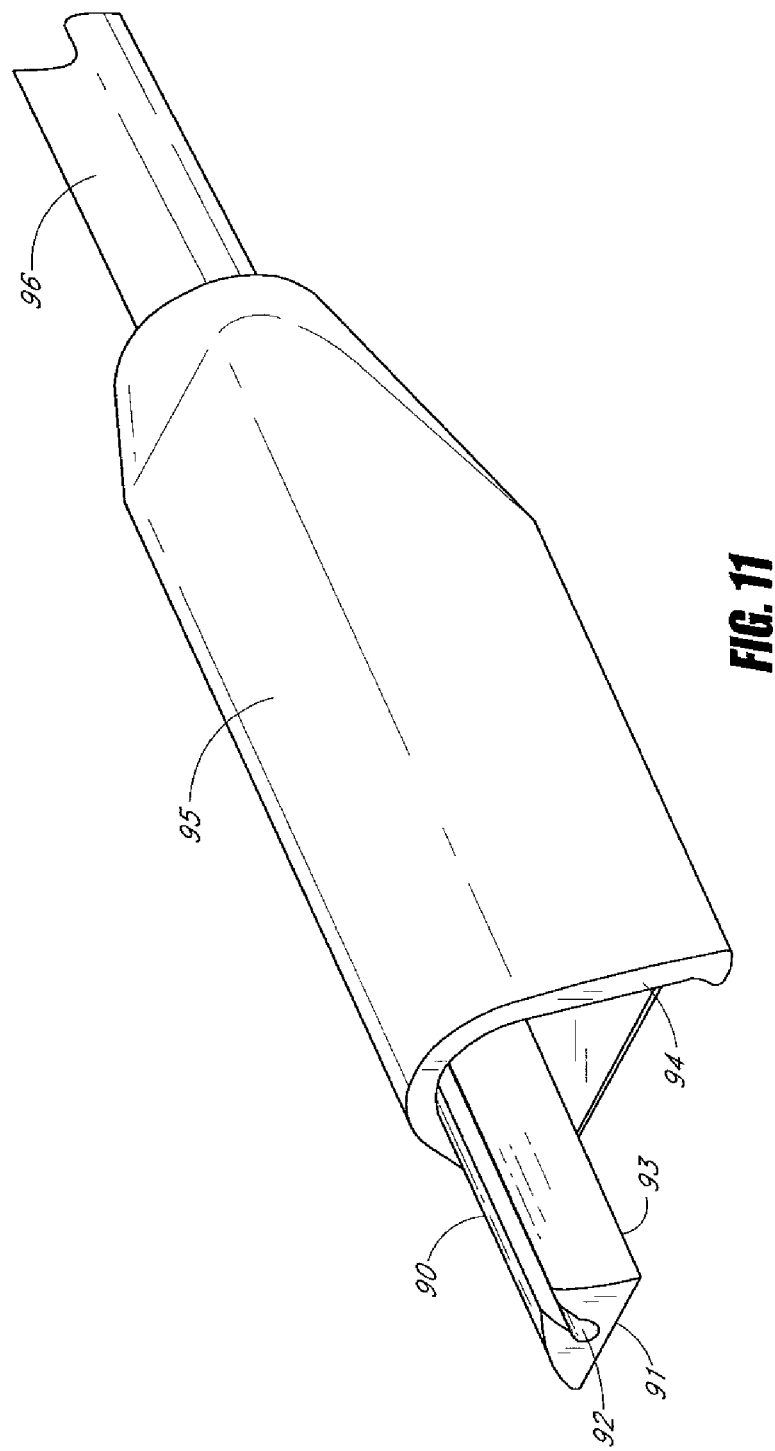
FIG. 11 shows one embodiment a delivery tool.

FIG. 11 shows a delivery tool with a shaft 96 with distal end 95 having an anvil or striking surface 94 defining a leading edge mated to at least a portion of the cross section of the trailing edge of the anchor. The shaft may be connected at its proximal end to a handle or terminate in a striking surface. Because a contour and size of the anvil surface is similar to those of the anchor in some embodiments, both the anchor and at least part of the distal end of the delivery tool can be driven into a bone thereby counter sinking the anchor. Alternatively, anchors according to one or more aspects of the invention can be left flush or partially countersunk. A mounting member 90 may extend beyond the implant when the implant is mounted or loaded on the tool. The mounting member 90 includes a flattened lower surface 93 and a rounded blunt front surface 91 for positioning along a bone surface, such as the top of a vertebral endplate, and a slot or engagement means 92 for accepting and aligning an anchor.

Figure 12:
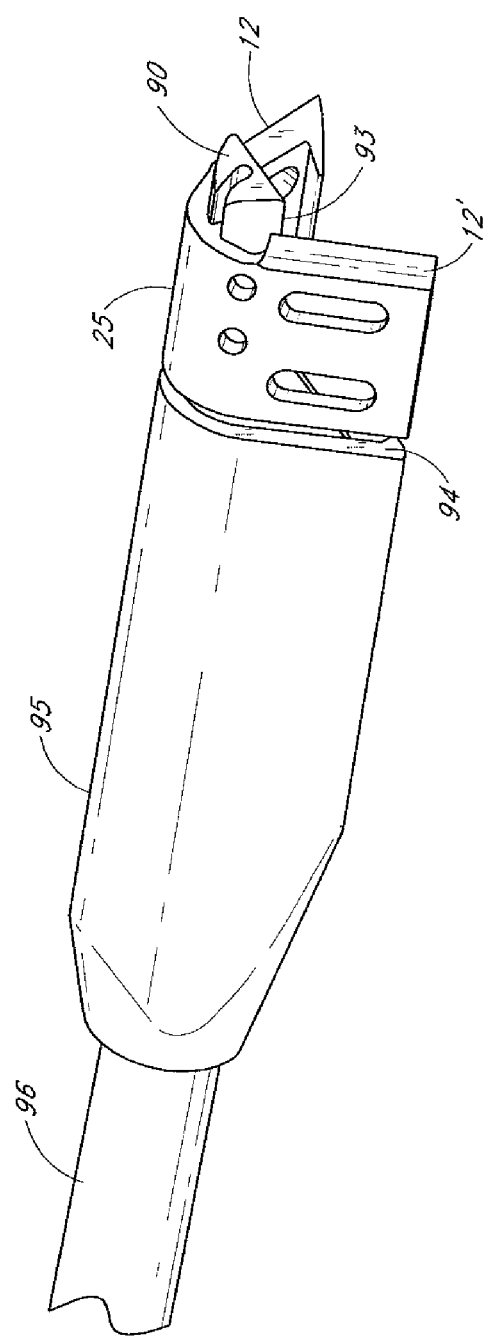
FIG. 12 shows the delivery tool in the previous figure with an anchor mounted

FIG. 12 shows the anchor 25 mounted on the mounting member 90. The extended lower surface 93 and the leading edge of the implant 12 and 12' forms a means to engage bone or other tissue. In one embodiment, the tissue (e.g., bone) engagement means comprises a device having an angled surface that may be used to hook onto, engage, or align the instrument with the edge of a vertebral body or the intersection of two tissue planes. In one embodiment, the engagement means can be used to align the implant with the top of a vertebral endplate and its front outer surface, the anchor is then driven into and across the endplate.

Figure 13:
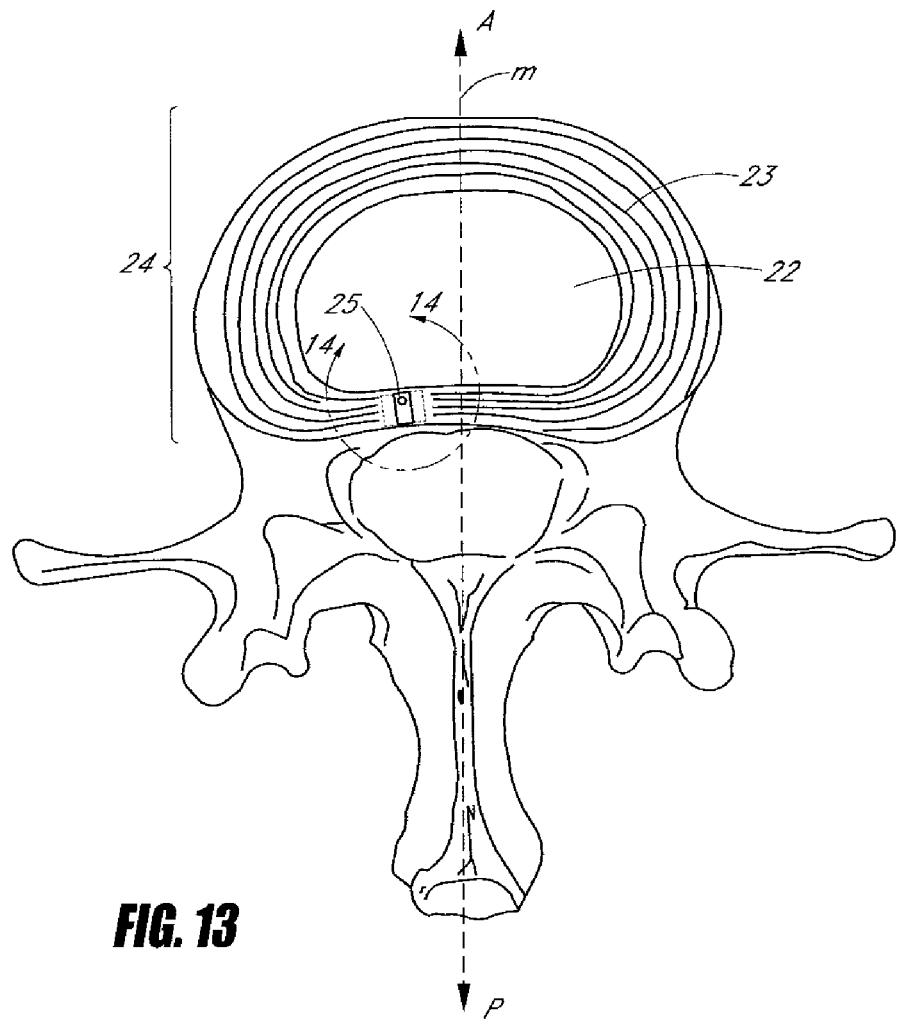
FIG. 13 shows an axial cross sectional view of a vertebral body and implanted anchor.

FIG. 13 shows a cross-section of a vertebral body 24 having an anulus fibrosus 23 bounding nucleus pulposus 22 with an anchor 25 embedded into a posterior aspect of an endplate and within or proximal to an anulotomy or defective region of the anulus fibrosus 23. This implantation site is also in the vicinity of the cortical rim or ring of dense bone of the vertebral endplate. The anchor is shown countersunk into the bone along the P-A axis but partially proud along the inferior-superior axis (the dotted lines indicating the portion of the implant below bone surface or level.

Figure 14A:
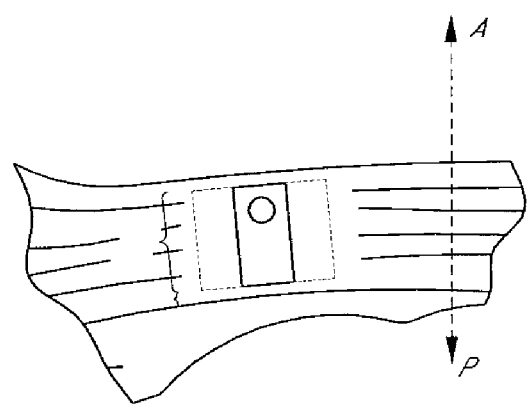
FIGS. 14A-B show an expanded view and a frontal view of the implanted anchor in the previous figure.
Figure 14B:
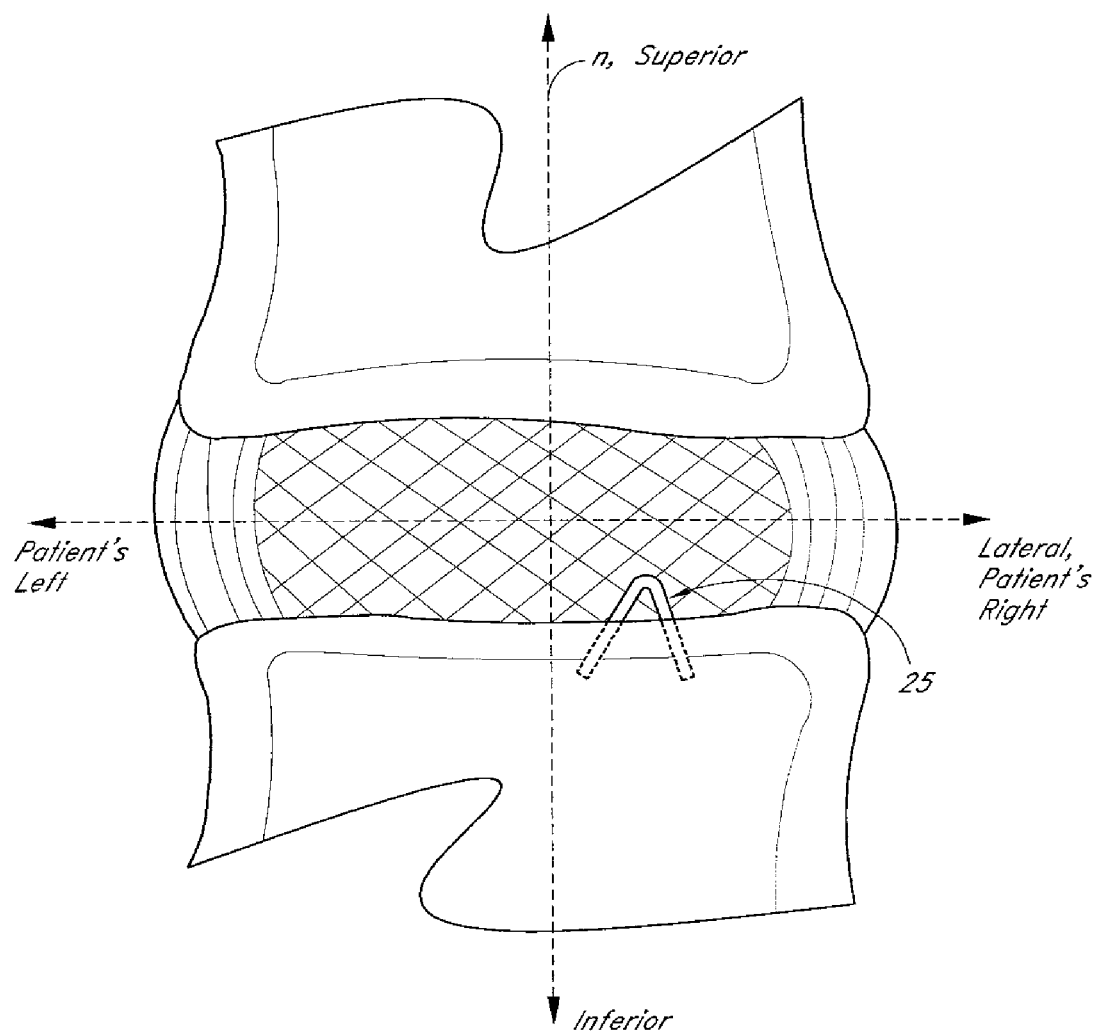

FIG. 14A is an expanded view of FIG. 13 and shows dotted lines to represent the keel portion of the anchor 25 beneath the endplate surface. FIG. 14B is a dorsal view of FIG. 14A showing anchor 25.

In FIG. 15, a sagittal view of an implanted anchor 25 is shown at least partially within the defect 33 and inferior vertebral body 32. Superior vertebral body 31 is also shown. The cross-section of the vertebral bodies depicts the denser and thicker cortical bone at the edge or rim where the anchor is implanted and the less dense cancellous bone within the vertebral body.

Figure 16:
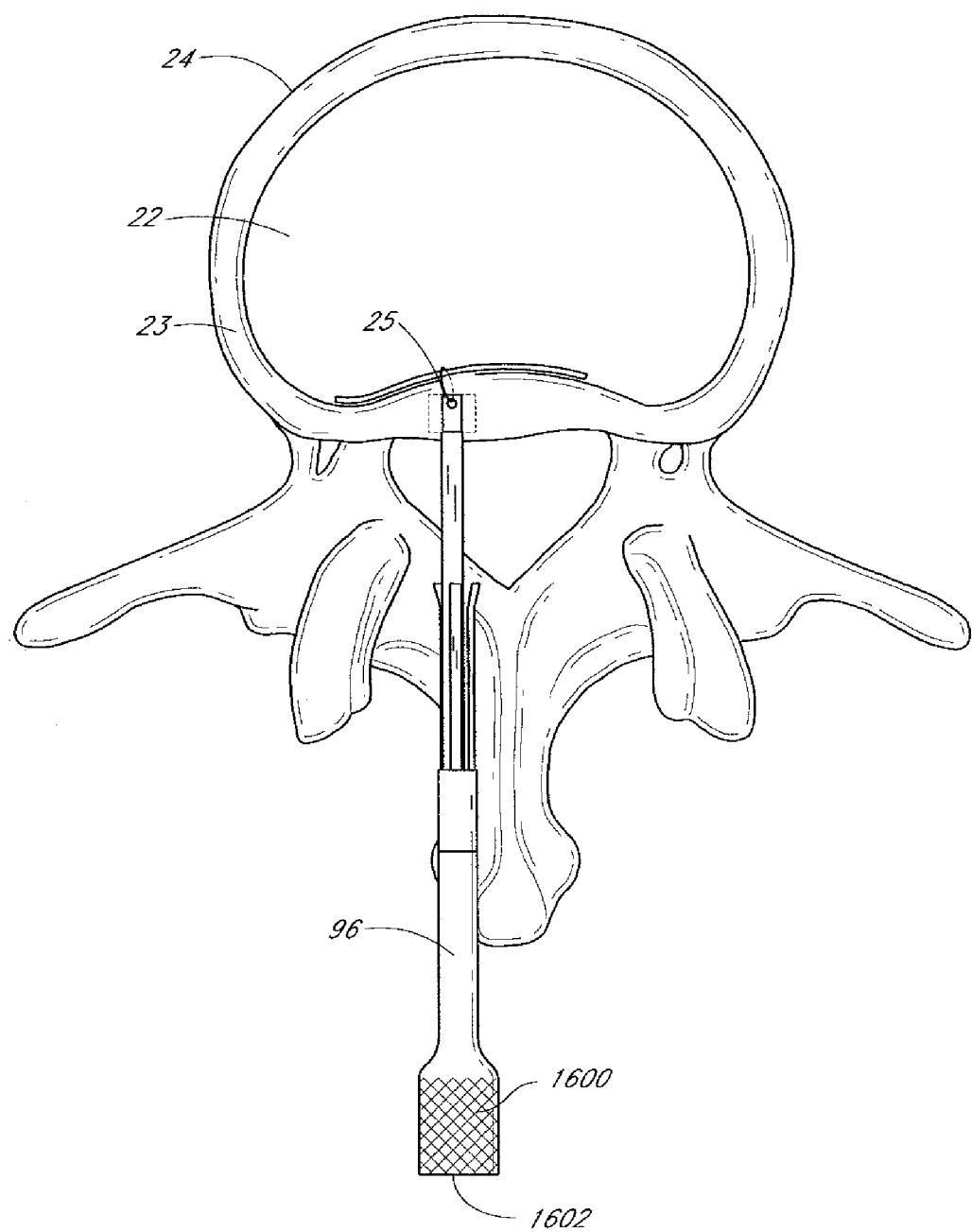
FIG. 16 shows an axial cross sectional view of a vertebral body and a delivery tool inserted along an endplate in the vicinity of an anulus defect or anulotomy.

FIG. 16 depicts a method of delivery for one embodiment of the anchor and associated delivery tool. Shown is a top cross sectional view of a vertebral body 24 and a delivery instrument 96 and an anchor 25. The delivery instrument or driver is used to transmit the force of a hammer or other means to drive the anchor in place. The driver can comprise a slot, holder, magnet, pins, mateable surfaces, fastener or other means at its distal end to engage or couple with the anchor. The anchor can also be attached to the distal end of the driver and then released once the desired delivery depth has been attained. Other features of a driver (not shown in FIG. 16) can include a depth stop, bone engagement means such as a spiked, hooked, or angled protrusion, and/or a retractable sleeve to protect adjacent anatomy as the anchor is positioned. FIG. 16 also shows a flat proximal end 1602 for hammering, if needed and a knurled handle 1600.

Figure 17:
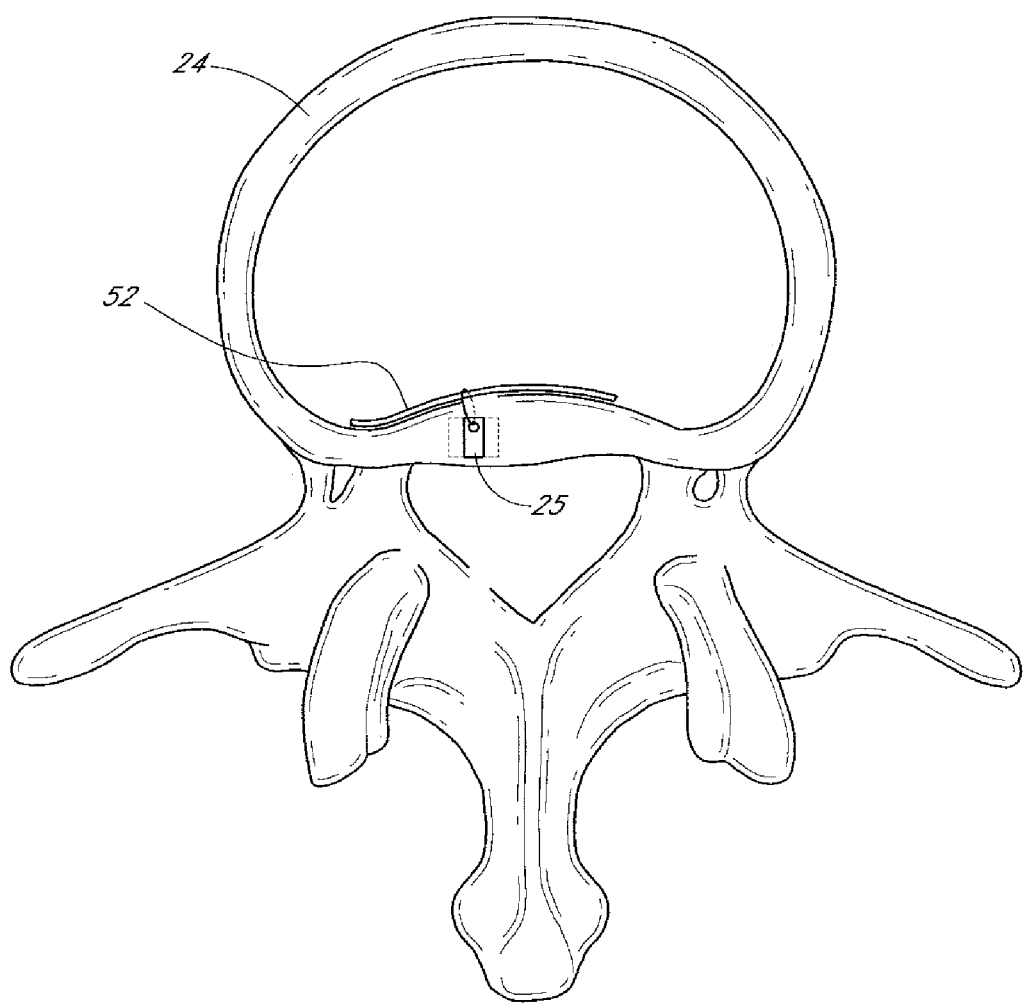
FIG. 17 shows an axial cross sectional view of a vertebral body wherein an anulus reinforcement device has been implanted along and within the anulus and is attached to an anchor embedded within the vertebral body.
Figure 18A:
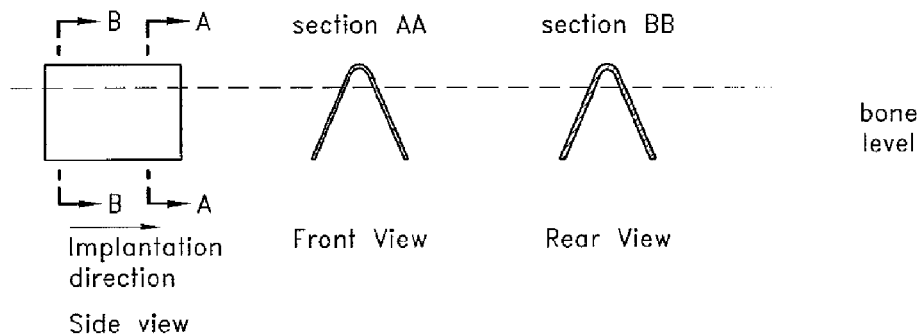
FIGS. 18A-C show various views and features of anchors according to one or more embodiments.
Figure 18B:
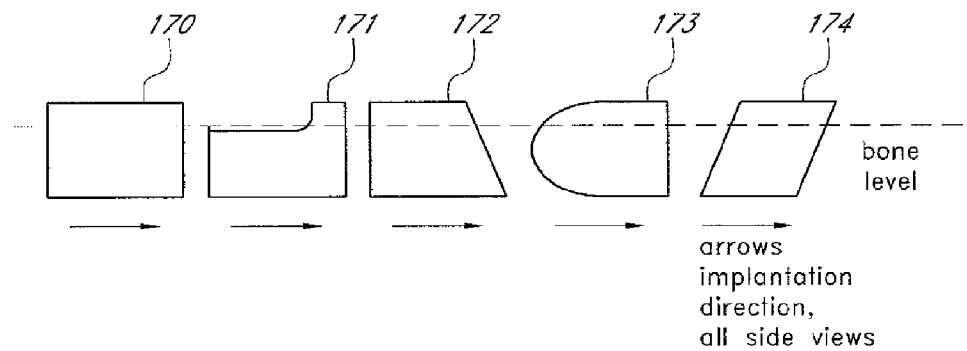
Figure 18C:
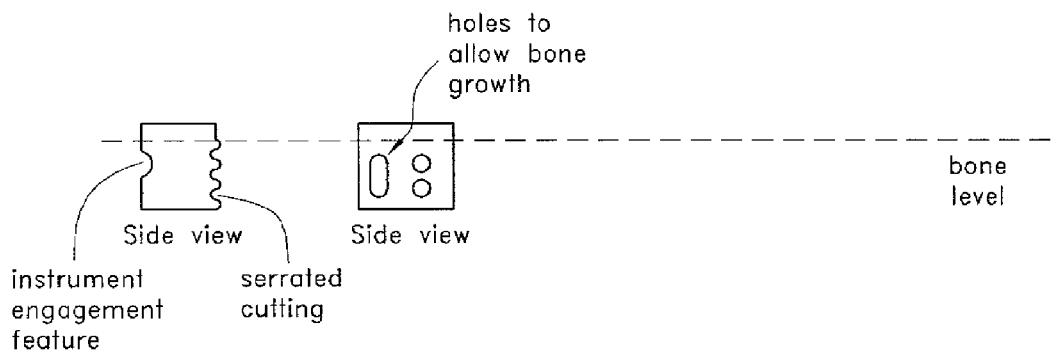

FIG. 17 illustrates a top cross-sectional view of an anulus repair implant 52 lying along the inner surface of the posterior anulus that can be coupled, attached, or sutured to an anchor 25. The connection between the anchor and implant can be permanent or detachable. The implant 52 can be delivered and positioned prior to, at the same time as, or subsequent to the implantation of the anchor 25. FIGS. 18A-18C show various features of anchors.

In FIG. 18A, the surface level of a bone such as a vertebral endplate is shown as a dotted line. A side view is depicted. Here the leading edge of the keel or leg portion of the implant is thinner than the trailing edge. Accordingly, in other embodiments of anchors at least a portion of the leading edge, profile, proximal edge or side of an implant can have a thinner or tapered profile than an opposing end, distal end, or trailing edge or profile. FIG. 18B shows a series of anchor variations from a side view in which the top portion, apex, neck, or implant attachment site 170, 171, 172, 173, 174 is symmetrical, rounded, wedge shaped, oriented at the distal or proximal end of the anchor. FIG. 18C shows another side view along the bone surface level depicting and anchors with features discussed infra such as a serrated leading edge, voids or ingrowth holes, and a recess for engaging a delivery tool.

Figure 19:
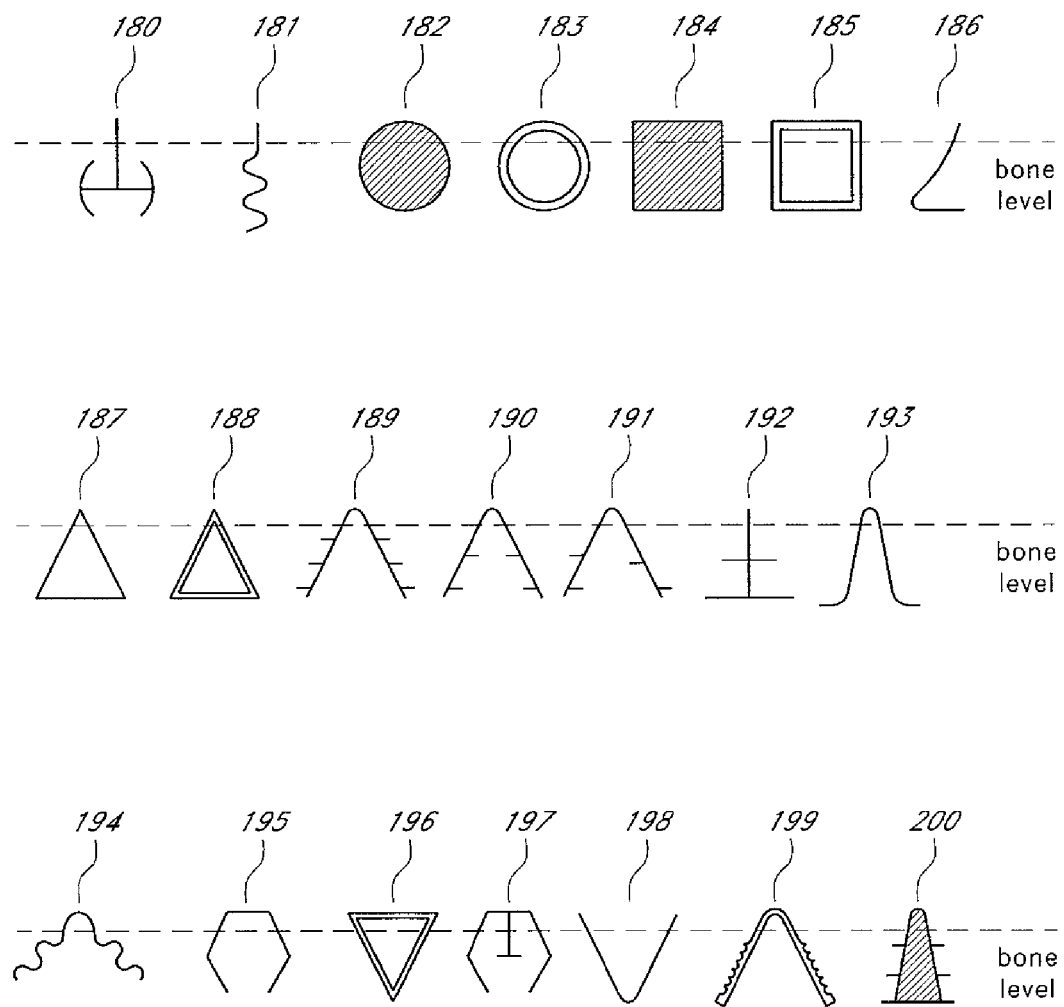
FIG. 19 shows various profiles of the keel portion of one or more anchors.

FIG. 19 shows various embodiments of the anchor cross-sections 180-200 including several keel profiles from a front view resistant to pullout and offering various surface areas. Some are solid shapes as in anchor profiles 182, 184, 187, and 200 and others are hollow and have an open midsection as in anchor profiles 183, 185, 188.

Figure 21:
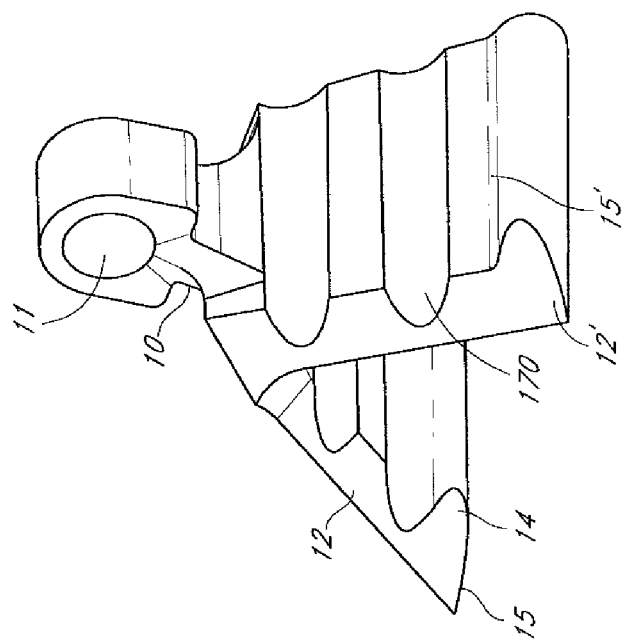
FIG. 21 shows a perspective view of another embodiment of an anchor according to one or more embodiments with an "eye" attachment means.
Figure 20:
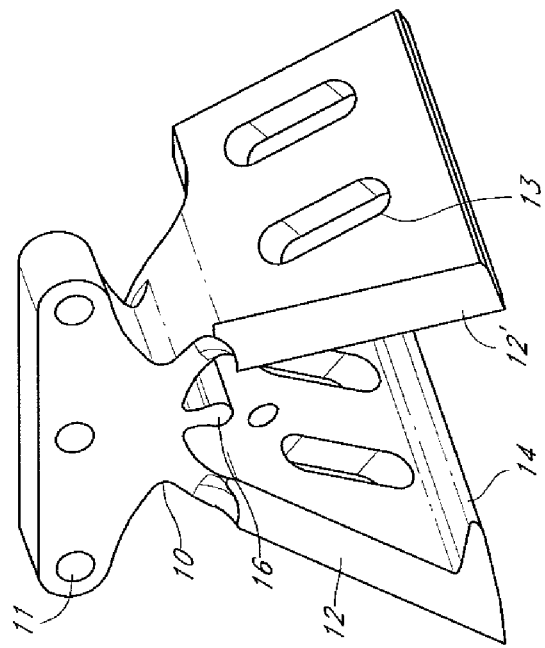
FIG. 20 shows a perspective view of another embodiment of an anchor according to one or more embodiments with a plate-like attachment means suitable for three sutures.

Turning to FIG. 20, a perspective view of an anchor is shown with leading edges 12, 12', alignment means 16, suture or fastener attachment 11 site, neck 10, and voids 13. In this embodiment the apex does not run the entire length or depth of the anchor corresponding to the keel or opposing leg portions 15, 15' of the anchor. Also, the neck is oriented towards the proximal end of the anchor forming a cut-out along the top portion of the anchor. The neck 10 is shown perpendicular to the keel 15 but can be alternatively oriented in a range from 0-180 degrees relative to it. In one embodiment, the neck is oriented at an angle of about 15, 30, 45, 60, 75, 90, 120, 150, or 180 degrees relative to the keel In FIG. 21, a "V" shaped anchor is shown. An "eye" or loop 11 is integral to a neck extension portion 10 that bifurcates into two legs 15, 15'. Because the leading edges 12, 12' and at least a portion of the neck 10 is sharpened, this anchor can be driven more flush to the upper or first surface of a bone such as a vertebral endplate. Here both the neck 10 and the leg portions 15, 15' of the device function as a keel. This embodiment also shows ridges 12 and scalloped recesses 170. Anchors according to other embodiments described herein may also comprise ridges and/or scalloped recesses.

Figure 22B:
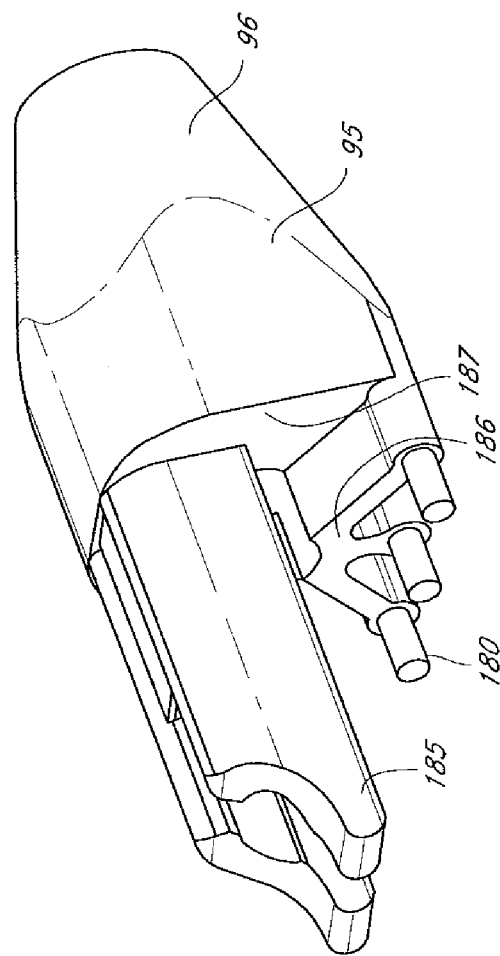
FIGS. 22A-B show embodiments of the anchor and delivery tool.
Figure 22A:
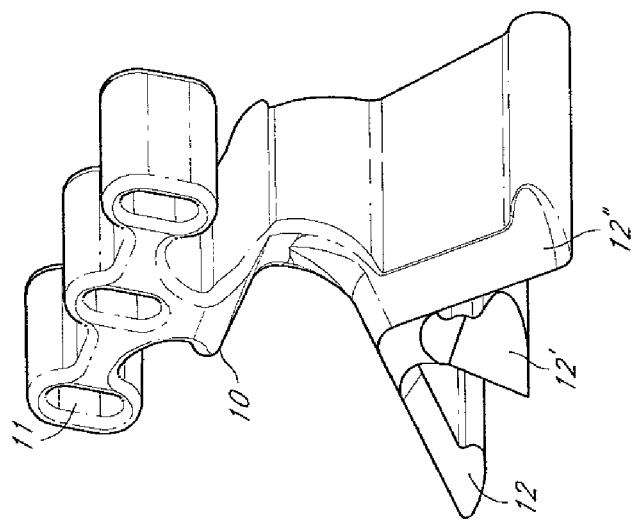

In FIG. 22A, another embodiment of an anchor is shown. Here, three legs 12, 12', and 12" defining the keel are provided. A relatively taller neck 10 is provided beneath a perpendicular suture attachment member 11. The neck 10 is set back distally from the leading edge of the keel portion. FIG. 22B shows the distal tip of a delivery tool. Shown are attachment pins 180, anvil or striking surface 186, depth stop 187, mounting member 185, and shaft 96 with distal end 95.

Turning to FIG. 23A, an anchor 25 is shown with an attachment site 189 for a flexible bridge 818. The bridge 818 is shown in FIG. 23B and is coupled to the neck 10 of the anchor 25 with a first and second flexible tab 193, 194 and has an attachment 11 site at the opposing end.

The series depicted in FIGS. 24A-24C shows an anulus reinforcement system. FIG. 24A shows an anchor similar to the ones depicted previously with a bifurcated keel 15, 15', neck 10, and attachment plate 112 with a first and second coupling member 111, 111' or snap surface. FIG. 24B is an exploded view of a barrier, mesh, or reinforcement plate 52 adjacent an anchor 25 wherein the anchor 25 is partially inserted or mounted within the distal end of a delivery tool. FIG. 24C shows all three elements connected and mounted and ready to be driven into a tissue site.

Figure 25A:
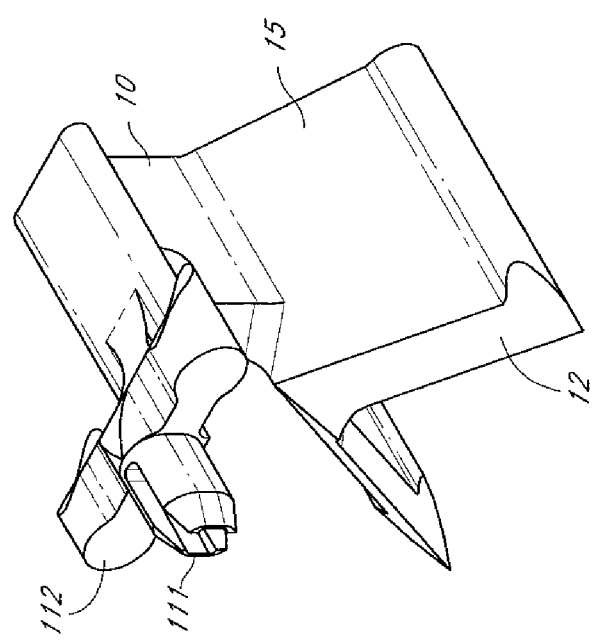
Figure 25B:
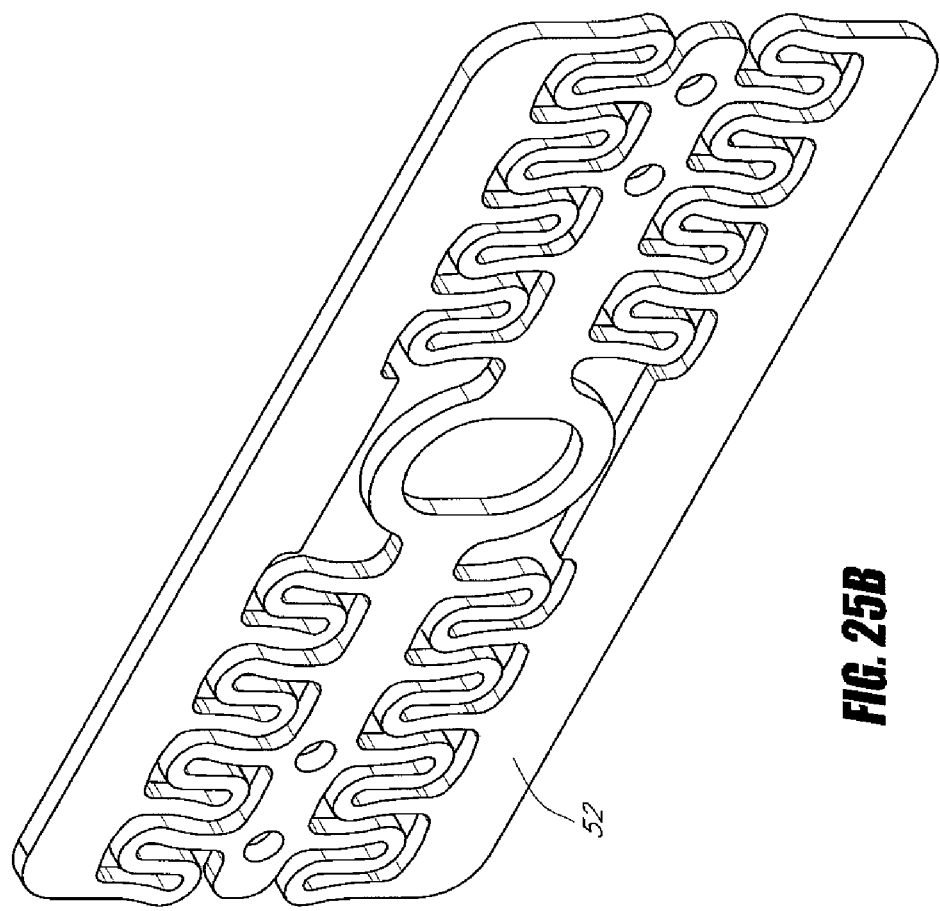

Another embodiment of an anulus reinforcement system is shown in FIGS. 25A-25C. In this embodiment, a single attachment means 111 is used that can function as a fulcrum or hinge site for a flexible barrier 52 member shown in FIG. 25B. Behind or distal to the attachment means 111 is a support member 112 or plate that is an extension of the neck 10. This feature, in some embodiments, inhibits the barrier 52 from folding backwards and may also reinforce the barrier 52. FIG. 25C shows a hood or sleeve 120 element that can be mounted on or carried by a delivery tool or instrument as described herein. The hood 120 retains the folded barrier until the anchor portion is fully established within the tissue whereupon it is retracted.

Figure 26B:
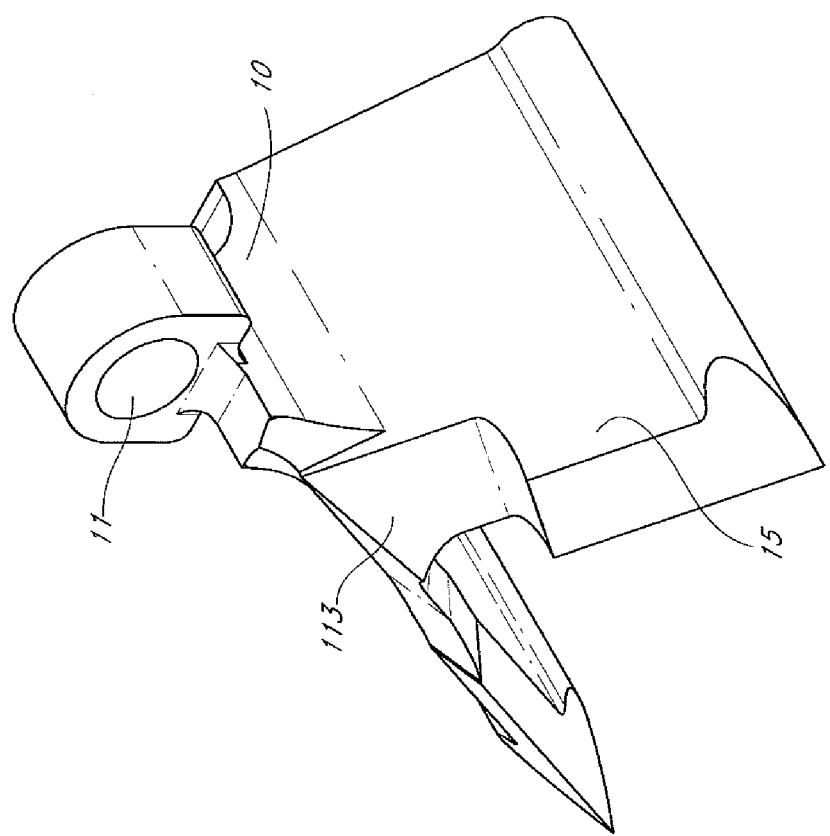
FIGS. 26A-B show a side view and perspective view of an anchor with a sharpened leading edge having a recessed region corresponding to the cupped cortical rim of a vertebral endplate.
Figure 26A:
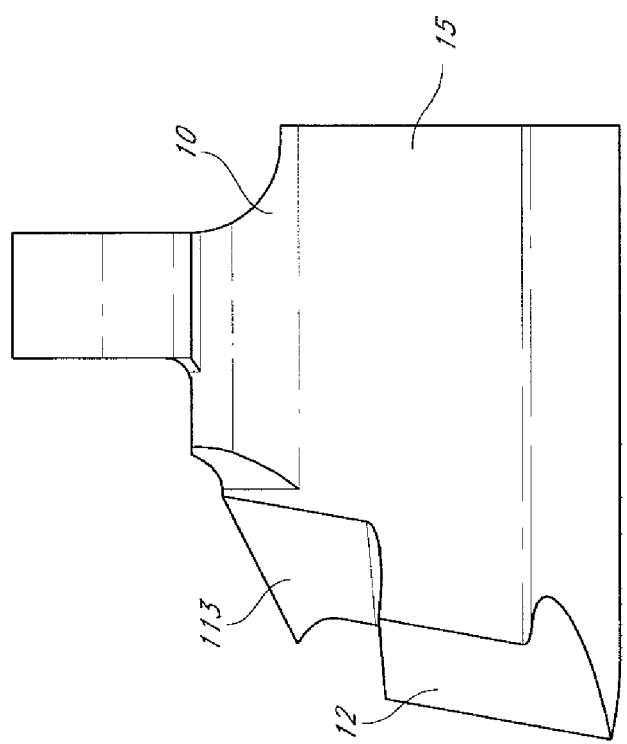

Another embodiment is shown in FIGS. 26A-26B. This embodiment shows an anchor especially adapted for use in a vertebral body and includes an upside down "V" shaped keel portion with a sharpened leading edge. The leading edges enable the anchor to be directly driven into the bone and do not require a pilot hole or pre-cut and One feature of this embodiment is the leading step in the sharpened edge which presents more cutting surface blow the surface of the bone and more forward of the distal attachment site. Alternatively, the leading edge can have multiple steps or be curved and rounded. This profile reduces the risk that the leading edge might pierce or damage the endplate (which is not flat but has a "dip" or cupped portion in the middle). This feature facilitates insertion of a longer, stronger anchor into a disc that would otherwise (because of a pronounced dip) be difficult to position at the proper height and depth into the bone without damaging the endplate.

The following Example illustrates one embodiment and is not intended in any way to limit the invention. Moreover, although the following Example describes an anchor used in a spinal application, the anchors described herein can be used throughout the animal body and have general applicability to fastener art. Such anchors can be used to join or anchor like or disparate materials or tissues together, maintain alignment of materials, reinforce a fracture within a material, and provide an attachment site along or within a materials surface.

The anchor illustrated in FIG. 26 is used by way of example. The anchor is in the form of an upside down "Y" defined by a neck portion terminating at one end into two plate-like rectangular legs forming a keel and terminating into an suture attachment site 11 in the form of a loop on the other end. The leading edge of the legs 12 and neck 10 are sharpened and the upper portion of the legs is recessed, profiled or formed with a relief 113. The relief profile 113 can correspond to an anatomical structure. In this embodiment the forward recess or relief 112 corresponds to the concavity or cupping of an endplate. The angle between the keel plates is around 90 degrees. The neck 10 is about 0.1 millimeter high and about 0.2 wide millimeters wide and extends about 0.2 millimeters. The neck 10 and attachment site 11, an "eye" or loop in this embodiment, are mounted at the trailing or aft potion of the keel 15.

The entire structure is made of nickel titanium and is machined from bar stock. To be delivered, the anchor is mounted on the distal end of a driver. The driver has a striking surface on one end and an anvil on the opposing end. The anvil has the identical cross-section as the trailing edge of the anchor and extends about 0.2 cm to allow for countersinking.

The anchor is coupled to the anvil by a forked protrusion that holds the neck and a pin that fits into the eye.

In one application, the anchor is used to secure an anulus repair device relative to a defect in the disc. A posterior-lateral approach is used to obtain access to the damaged disc. Part of the posterior elements on the opposing vertebral bodies may have to be removed in order to reach the disc. The anulus repair device is then implanted through the defect and along the inner surface of the anulus.

Next the anchor, which is mounted on the distal end of the driver, is aimed at the top edge or endplate of the inferior intervertebral body. An alignment projection forming a right angle at the tip of the drive is used to align the bottom potion of the attachment loop of the anchor with the upper surface of the endplate and to center the anchor within the defect. The anchor is then driven forward into the bone with light hammering applied to the driver. The anchor is driven roughly perpendicular to the outer surface of the vertebral body and roughly parallel to the endplate.

The depth of insertion is controlled by the 0.2 cm countersinking anvil and the depth dimension of the anchor, in this case 0.5 cm for a total depth of 0.7 cm which is still shy of the border of the cortical rim and the cupping of the endplate. Only the upper potion of the loop remains proud of the endplate surface and the annular repair device can then be connected to it with a suture.

Graft Containment

Figure 27A:
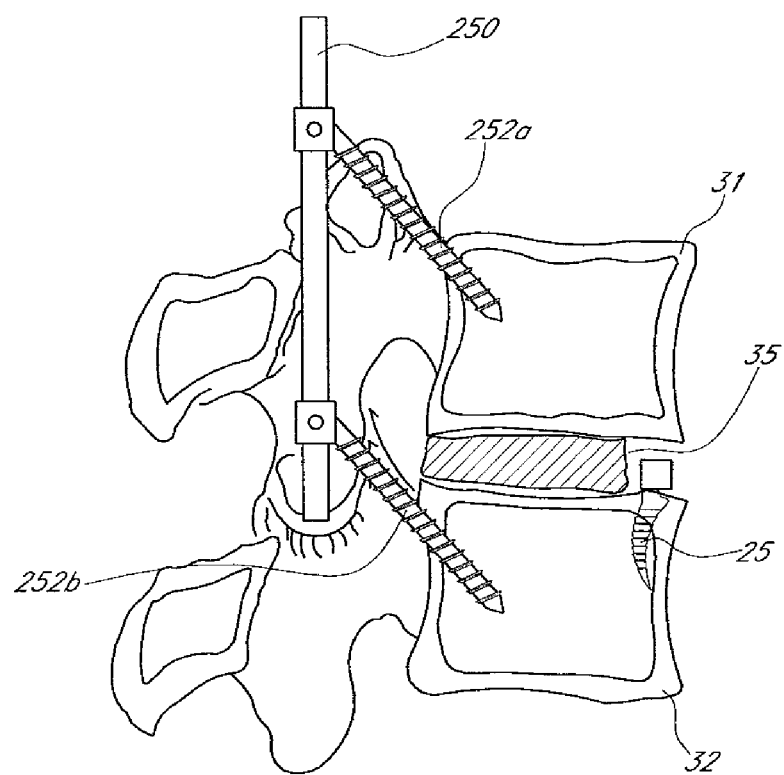
FIG. 27A illustrates an embodiment of a stabilization assembly in combination with a separate anchor.

FIG. 27A illustrates a lateral view of a stabilizer assembly 250 secured to patient tissue via a first and second fastener 252a and 252b. The stabilizer or spinal fixation assembly can comprise the embodiments disclosed in for example U.S. Pat. Nos. 6,562,040, 6,364,880 5,437,669 and 5,262,911, all herein incorporated by reference. The first fastener 252a is, in one embodiment, attached to or engaged with a superior vertebral body 31. The second fastener 252b is attached to or engaged with an inferior vertebral body 32. In this embodiment, the stabilizer assembly 250 is arranged towards the posterior of the superior and inferior vertebral bodies 31, 32. Also shown is anchor device 25 that functions as an anterior buttress or graft containment device.

In FIG. 27A, an anchor 25 is implanted in an upper anterior region of the inferior vertebral body 32. A portion of the anchor 25 extends above or is proud of an upper surface of the inferior vertebral body 32. In one embodiment, the portion of the anchor 25 extending above the surface of the inferior vertebral body 32 is arranged to block or secure a graft, frame, plate, and/or barrier 35. In this embodiment, the anchor is implanted in the anterior portion of the endplate. In other embodiments, the anchor may be implanted in the posterior portion. Additionally more than one anchor or anchor type as disclosed herein may be used in more than one location to block the implant. In one embodiment, the graft 35 comprises a femoral allograft. A wide variety of other grafts and devices, such as loose bone grafts and/or cages can also be secured or blocked by the anchor 25.

Figure 27B:
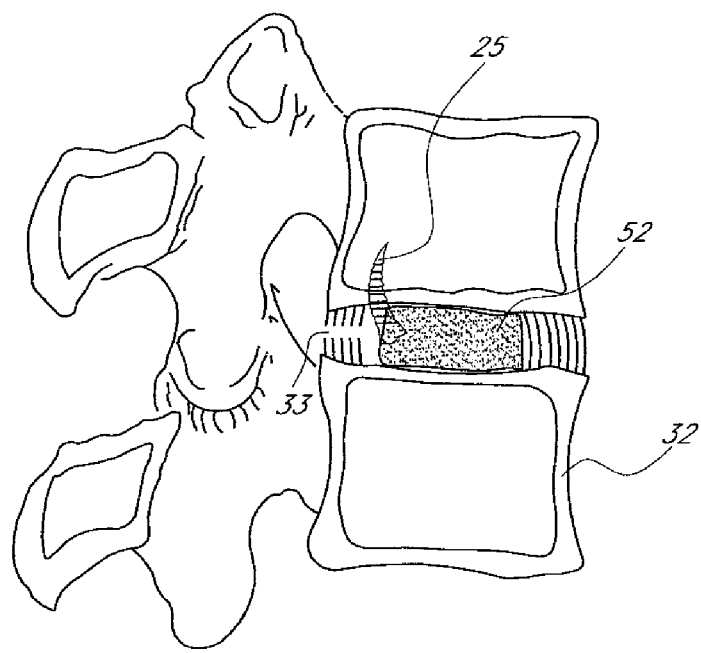
FIG. 27B illustrates an embodiment of an anchor secured to bone tissue and connected to an implant.

FIG. 27B illustrates another embodiment where an anchor 25 is attached to a lower posterior portion of a superior vertebral body 31. In addition to the curvilinear anchor depicted in the illustration, other anchors disclosed herein and included in various figures may be used for the same purpose. For example, plate-shaped or screw anchor may be used. In one embodiment, a portion of the anchor 25 is proud of the surface of the superior vertebral body 31 and is further arranged to block or secure a nonfusion intervertebral device 52. The device 52 can comprise an artificial disc or partial nucleus replacement device or other type of implant suitable for the needs of a particular implementation.

Figure 28A:
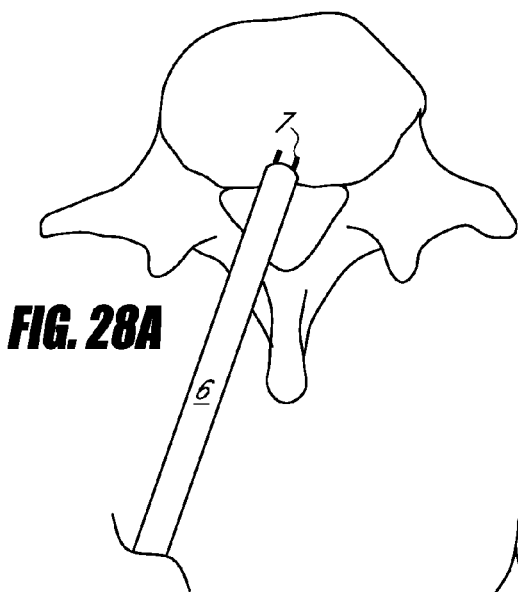
FIGS. 28A-28F illustrate various approaches of an implantation tool to target tissue.

FIGS. 28A-28F illustrate a plurality of approaches of an implantation tool 6 having one or more alignment structures 7 configured to align and locate an anchor or other implant. FIG. 28A illustrates one embodiment of a posterior lateral approach where an anchor or other implant can be driven into the posterior rim of either adjacent spinal end plate or proximal tissue.

Figure 28B:
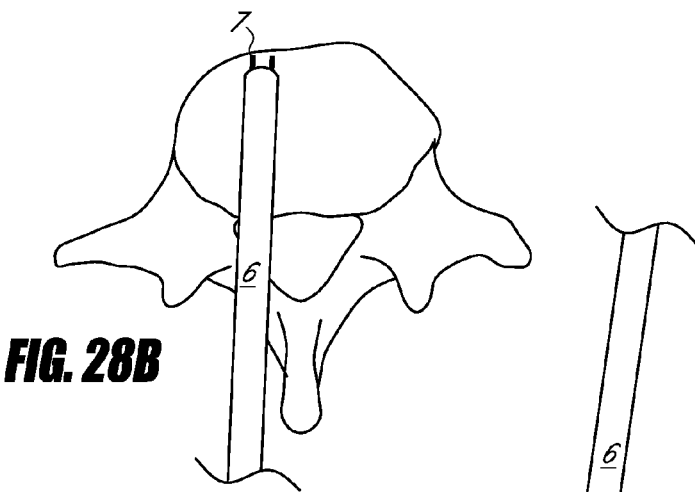

FIG. 28B illustrates an embodiment of a posterior approach between adjacent end plates and advance of the implantation tool 6 such that a distal end of the implantation tool 6 is advanced to an anterior aspect of the respective vertebral body. FIG. 28B illustrates that an anchor or other implant can be delivered to the vertebral end plate along its anterior cortical rim or tissue proximal thereto. In some embodiments, multiple anchors or other implants can be delivered along similar approaches to anchor or block native tissues and/or intervertebral devices such as one or more grafts, fusion devices, cages, anulus augmentations, nucleus augmentation devices, and the like.

Figure 28C:
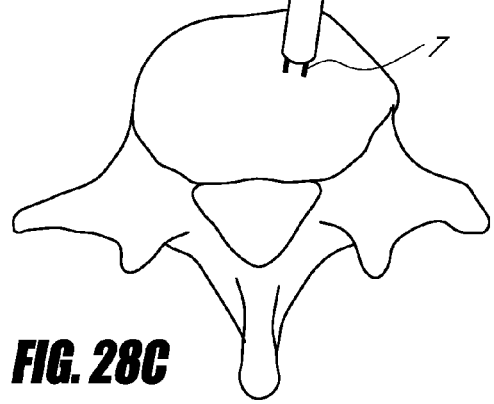
Figure 28D:
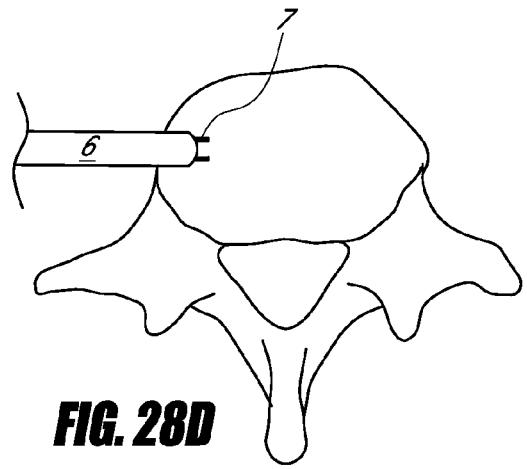
Figure 28E:
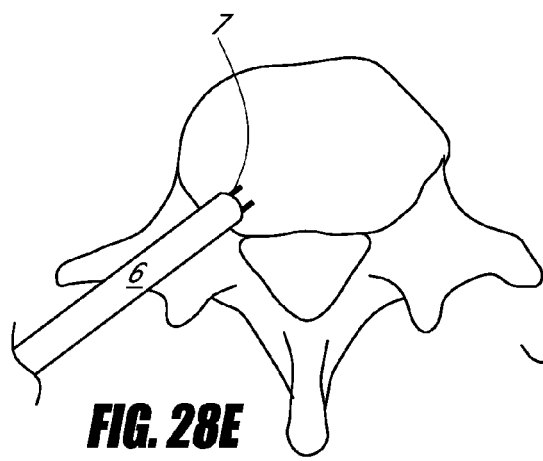

FIG. 28C illustrates an embodiment of an anterior approach for delivery of an anchor or other implant at an anterior delivery location. FIG. 28D illustrates a transpsoas approach for delivery of one or more anchors or other implants at a proximal delivery location. FIG. 28E illustrates an embodiment of a transforaminal approach of an implantation tool 6 for proximal delivery of one or more anchors or other implants.

Figure 28F:
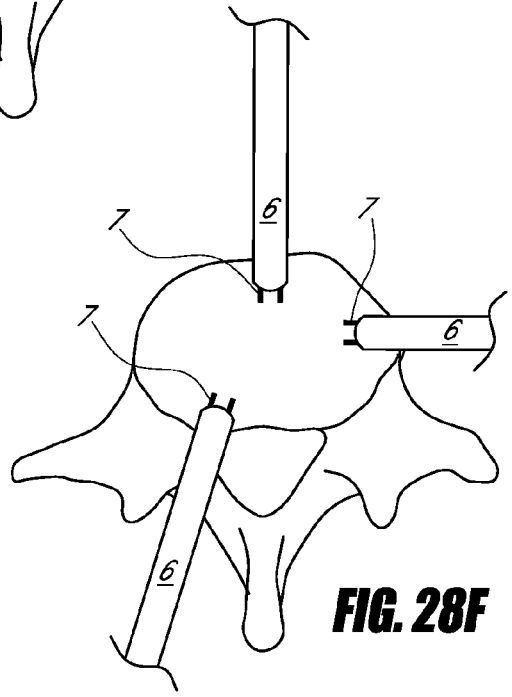

FIG. 28F illustrates multiple approaches of an implantation tool 6 for delivery of a plurality of anchors or other implants at respective delivery sites. FIGS. 28A-28F illustrate some of a wide variety of embodiments and appropriate approach vectors and delivery sites can be readily determined by the clinician based on the particular needs of the patient. In one embodiment a multitude of anchor devices are implanted about at least a portion of the periphery of a vertebral endplate forming an elevated rim or artificial uncus. In another embodiment the anchors a placed apart and connected together with one more band, mesh, tube, plate, or suture.

FIGS. 29A-29F provide lateral or side views of various embodiments of one or multiple anchors 25 arranged to block and/or provide an attachment/securing site for grafts 35 and/or implants 52. In FIGS. 29A-29F, the left and right portions of each Figure corresponds generally to the outer rim or edges of superior and inferior vertebral bodies 31, 32. In addition to the curvilinear anchors depicted in the illustrations, other anchors disclosed herein and included in the figures such as plate and keel type anchors may be employed and implanted in a like manner as disclosed in FIGS. 29A-29F. Multiple anchors may be delivered about the periphery of the endplate or uncus to partially reconstruct damaged bone and/or tissue. Anchors may be connected with one or more membranes and/or frames as described herein.

FIG. 29A illustrates a single anchor 25 implanted through a lower end plate adjacent a defect in the anulus fibrosus 23 proximal the cortical rim but extending inwardly into the inferior vertebral body 32. In this embodiment, the anchor 25 is configured to block a nonfusion intervertebral device 52 from exiting the disc space to the left of the Figure while the remaining intact anulus is blocking the device from extruding from the right side of the Figure.

FIG. 29B illustrates an anchor 25 blocking a fusion device or graft 35. In this embodiment, the anchor 25 is arranged to rest proximal to the graft 35 but does not touch the graft 35.

FIG. 29C illustrates an embodiment where an anchor 25 is secured to an inferior vertebral body 32 such that the anchor 25 is barely proud the surface of the inferior vertebral body 32. The portion of the anchor 25 proud of the surface is connected to an intervertebral device 35 that can be either a fusion or nonfusion device as illustrated and described infra.

FIGS. 29D-29F illustrate a plurality of embodiments employing multiple anchors 25 where each anchor 25 can be substantially identical to other anchors 25 or where different versions or configurations of anchors 25, 25' can be employed. FIGS. 29A-29F are simply illustrative of certain embodiments and a variety of configurations and placements can be adapted to the needs of a particular patient. Though the anchors depicted in FIGS. 27-30 are depicted as curvilinear anchors it should be understood that this is for illustrative purposes only and any anchor described herein may alternatively or additionally be used according to the methods described.

In FIG. 29F, two opposing vertebral bodies 31, 32 are shown. Along the periphery of the opposing endplates are implanted a series of anchored implants. Implants are used to augment (e.g., build up) or replace weakened, damaged or missing hard or soft tissue, such as bone or anulus. In some embodiments, the anchored implants extend the uncus or cortical rim of the endplates. In certain embodiments, the anchored implants further comprise a membrane and optionally a frame. The anchored implants comprise a head, neck or engagement surface to attach or engage an adjacent anchored implant or another device (e.g., a barrier, band, or graft). Multiple anchored implants can be interconnected or stacked to form a fence, augmented or raised surface (e.g., above the endplate) to reduce or prevent the escape of extrusion of a graft or other material (artificial or natural) from the enclosed area. In one embodiment, graft containment can be achieved effectively by using a series of interconnected anchored implants, thus augmenting the uncus and reconstructing the endplate. Opposing endplates can be reconstructed in this manner. In one embodiment, both the inferior and superior endplates are reconstructed.

Figure 30A:
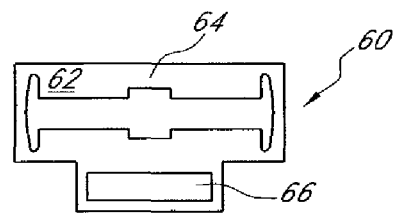
FIG. 30A illustrates a top view of one embodiment of a support member.

FIG. 30A illustrates a top view of an embodiment of a reconfigurable support member 60. The support member 60 is configured to block, provide support or serve as a barrier to inhibit herniation of tissue or migration of a graft or implant. In one embodiment, the support member 60 comprises a plurality of generally rigid elongate members 62 connected via interposed flexible connections 64. The flexible connections 64 are formed of a biocompatible resilient material to allow the support member 60 to resiliently move between a first and a second configuration. In some embodiments, the support member 60 can reconfigure itself automatically under resilient force provided by the support member 60 itself. In some embodiments, the support member 60 can be reconfigured under tension or compression force applied to the support member 60. In some embodiments, the elongate members 62 and flexible connections 64 are formed of the same or similar materials. The flexible connections 64 can comprise weakened regions of the support member 60 and/or regions where material comprising the support member 60 is thinner and/or narrower than the material in the regions of the elongate members 62.

Figure 30B:
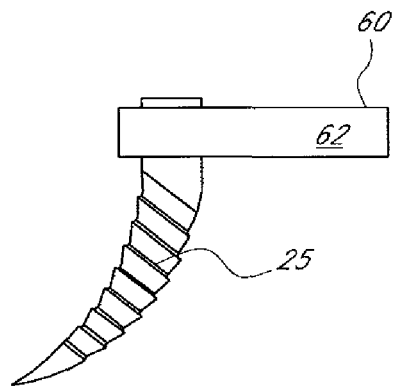
FIGS. 30B and 30C illustrate first and second configurations of an embodiment of a support member connected to an anchor.
Figure 30C:
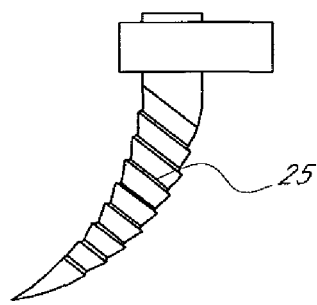

In some embodiments, the support member 60 comprises a connection portion 66 configured to engage with an anchor 25 as illustrated in FIGS. 30B and 30C. In some embodiments, the connection portion 66 engages with a corresponding anchor 25 via a friction fit. In some embodiments, the support member 60 can connect to a respective anchor 25 via suturing, one or more fasteners, biocompatible adhesives, ultrasonic welding, snap fit, or a variety of other methods, materials, and/or processes for joining separate elements. In some embodiments, the support member 60 and anchor 25 can be formed as an integral unit and need not comprise separate interconnected components.

FIG. 31A illustrates a further embodiment of a support member 60 with a corresponding anchor partially engaged with a connection region 66 of the support member 60. FIG. 31A also illustrates that the support member 60 defines a transverse dimension indicated by the designator T and a longitudinal dimension indicated by the designator L.

FIG. 31B illustrates a perspective view of the support member 60 fully engaged with an anchor 25. As previously noted, connections between the anchor 25 and support member 60 can comprise a wide variety of connection means including multiple means for connecting the support member 60 and anchor 25. In one non-limiting example, the anchor 25 can connect to the support member 60 via means for connecting comprising both a friction fit and a detent arrangement.

Figure 31C:
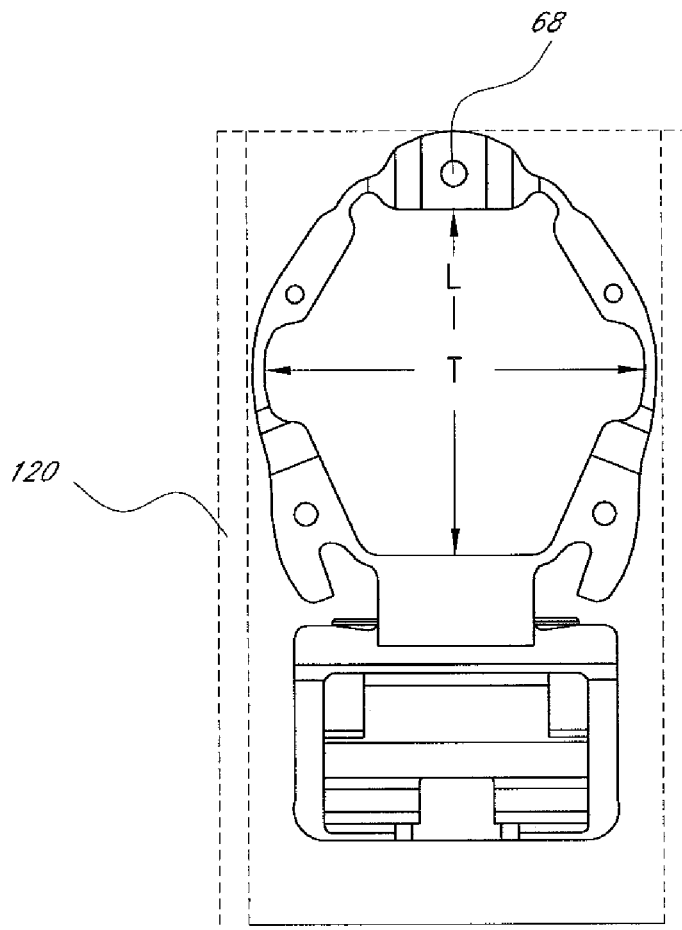
FIG. 31C illustrates a top view of an embodiment of a support member in an insertion configuration as maintained by a sleeve.

FIG. 31C illustrates a top view of the support member 60 in a configuration having a reduced transverse dimension and an elongated longitudinal dimension. In one embodiment, the configuration illustrated in FIG. 31C of the support member corresponds to a relaxed configuration for a natural configuration of the support member absent applied force. The reduced transverse dimension T of the support member 60 can facilitate advancement of the support member 60 towards a desire implantation location.

In one embodiment, the support member 60 comprises an attachment structure 68 arranged at a first or leading end of the support member 60. The attachment structure 68 can provide an attachment point for application of force to the support member 60. For example, a tension force can be applied to the leading end of the support member adjacent the attachment structure 68 to draw the leading end rearward so as to reduce the longitudinal dimension and expand the transverse dimension.

Figure 31D:
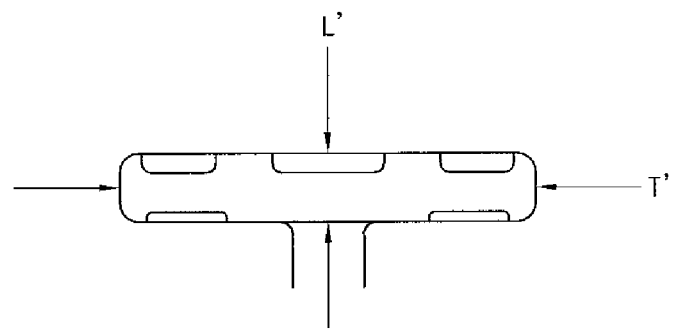
FIG. 31D illustrates a support configuration of the support member of FIG. 31C.

In some embodiments, FIG. 31C illustrates the support member in a configuration having force applied. For example, in one embodiment, a sleeve 120 can be arranged about the support member 60 to maintain a reduced transverse dimension T. Removal of the sleeve 120 can then allow the support member 60 to achieve a relaxed configuration having an expanded transverse dimension T and reduced longitudinal dimension L. In other embodiments, the configuration illustrated in FIG. 31C can be maintained by one or more sutures or clamps applied to opposed lateral sides of the support member 60 to maintain the reduced transverse dimension T. Removal or severing of such sutures or clamps can release the support member 60 to a relaxed state having an expanded transverse dimension T and a reduced longitudinal dimension L. This configuration is illustrated schematically in FIG. 31D with the reduced longitudinal dimension L' and the expanded transverse dimension T'.

Opposing Gates

Figure 32:
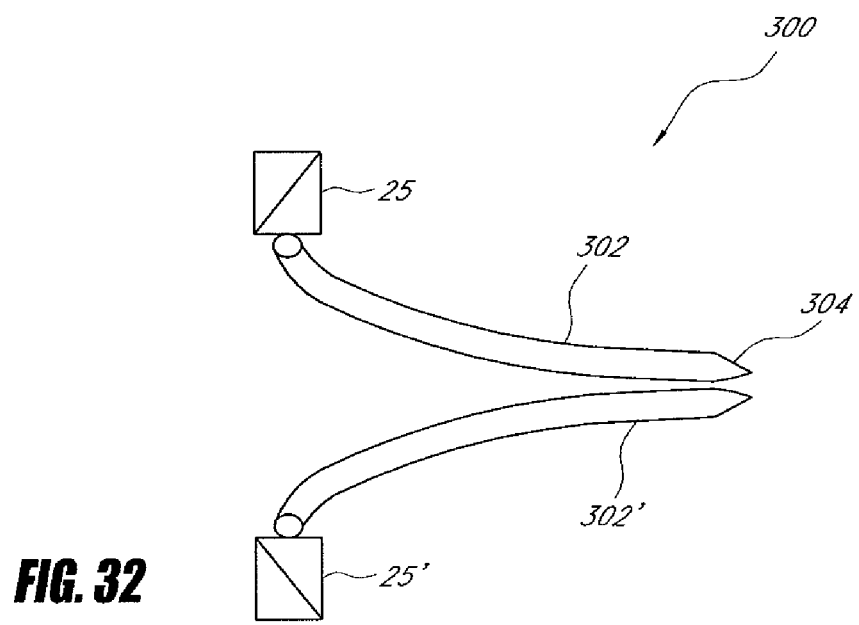
FIG. 32 illustrates an embodiment including a plurality of anchors connected to respective gate numbers.

FIG. 32 illustrates a side view of a support assembly 300 configured to support or retain patient tissue and/or a further implant member. In one embodiment, the support assembly 300 comprises a first anchor 25 and an opposed second anchor 25'. A first gate member 302 is connected or attached to the first anchor 25 and a second gate member 302' is similarly connected or attached to the corresponding second anchor 25'. In some embodiments, the gate members 302, 302' are formed of flexible material. Polymers may be used. Nitinol may also be used. In some embodiments, the gate members 302, 302' are formed of a resilient or elastic material. In some embodiments, the gate members 302, 302' can be at least partially rigid and movably attached to the respective anchor 25, 25' under resilient pre-loading for biased movement in a desired direction. Such embodiments provide the ability for opposed gate member 302, 302' to resiliently engage with each other to thereby provide an obstruction or resilient support inhibiting passage of patient tissue, fluids, and/or implanted materials from passing the support assembly 300.

Figure 33:
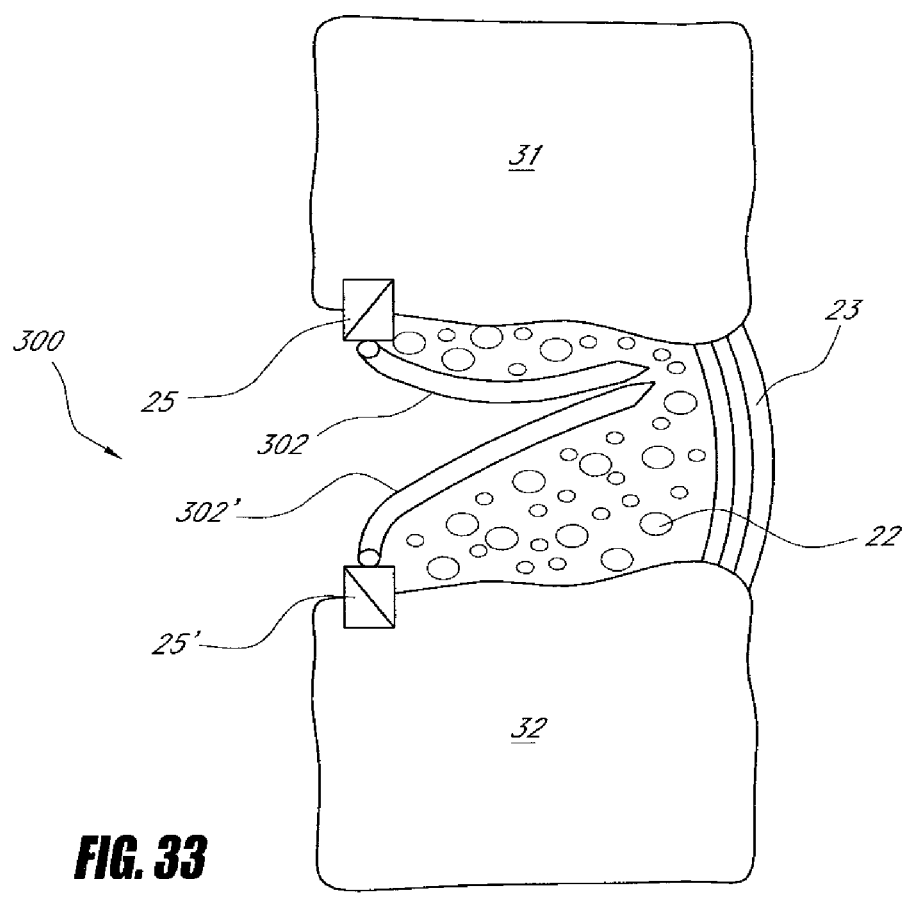
FIG. 33 illustrates an embodiment of anchors and attached gate members in one embodiment of an implanted position.

FIG. 33 illustrates a side view of a support assembly 300 in an implanted location. In this embodiment, a first anchor 25 is secured to a lower region of a superior vertebral body 31. A second anchor 25' is secured to an upper surface of an inferior vertebral body 32. Opposed first and second gate members 302, 302' resiliently engage with each other and are connected or attached to the respective anchors 25, 25'. In this embodiment, the gate members 302, 302' comprise a resilient and flexible biocompatible material. As illustrated in FIG. 33, the first and second gate members 302, 302' can flex to accommodate patient movement and variable loading resulting therefrom while maintaining a seal or blocking function facilitated by the resilient flexible engagement of the opposed gate members 302, 302'. For example, in an embodiment where the support assembly 300 is implanted to resist herniation of nucleus pulposus 22, the support assembly 300 via the resilient engagement of the opposed gate members 302, 302' can resist such herniation while accommodating relative movement of opposed end plates. A further advantage to certain embodiments of the support assembly 300 is that the moveable ability of the gate members 302, 302' inhibit passage of patient tissue, fluids and/or implanted materials yet allow the inflow of nutrients, tissue fluids and the like by providing a duckbill or reed valve configuration.

In some embodiments (including, but not limited to, FIG. 33), one or more gate members 302 can be substantially rigid and moveably attached to a respective anchor 25. A connection or coupling between a substantially rigid gate member 302 and a corresponding anchor 25 can comprise a flexible connection, a pivoting connection, and/or a hinged connection. A connection between a gate member 302 and respective anchor can further comprise a resilient or spring aspect such that the gate member 302 is urged in a particular direction of movement. In some embodiments, a support assembly 300 can comprise an integral assembly and need not comprise separate connected gate member 302 and anchor 25 components.

In one embodiment, (including, but not limited to, FIG. 33), a method of closing a defect between opposing vertebral endplates is provided. In several embodiments, a duckbill-type device is used. In one embodiment, the method comprises attaching a first gate member to a superior endplate and attaching a second gate member to an inferior endplate. Both gates have a proximal and distal end. The proximal end of the first gate is coupled to the superior endplate. The distal end of the first gate extends medially into an intervertebral disc space. The proximal end of the second gate is coupled to the inferior endplate. The distal end of the second gate extends medially into the intervertebral disc space. The method further comprises contacting the distal ends of the first and second gates to close a defect between opposing endplates. The distal end may touch or may be adjacent to one another. In one embodiment, the gates are partially or wholly positioned along an endplate beyond a defective region of the anulus. In another embodiment, the gates are partially or wholly positioned in the defect. In one embodiment, the anchor portion is in the defect and the gates are in front of the defect. A method that uses the gate system to close or barricade a defect in which the system is placed beyond the defect is advantageous in one embodiment because it reduces or prevents the extrusion or expulsion of nuclear material through the defect (which may be a weakened area vulnerable to additional damage). In one embodiment, the gates are about 2-4 mm wide, about 3-6 mm long, and about 0.5-2 mm thick.

Figure 34A:
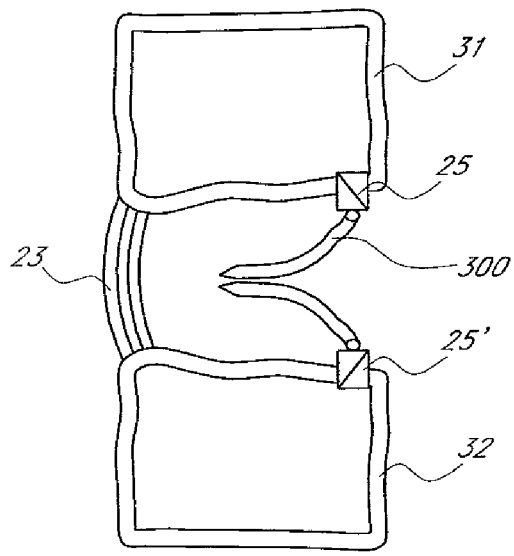
FIGS. 34A-34C illustrate a plurality of embodiments of anchors and attached gate members and corresponding implantation locations.
Figure 34B:
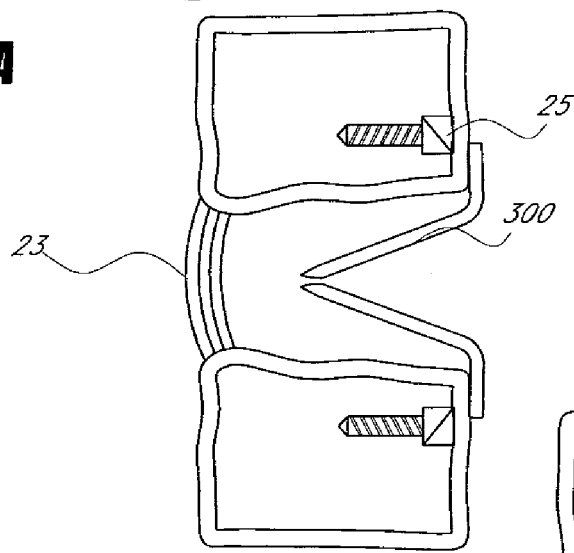
Figure 34C:
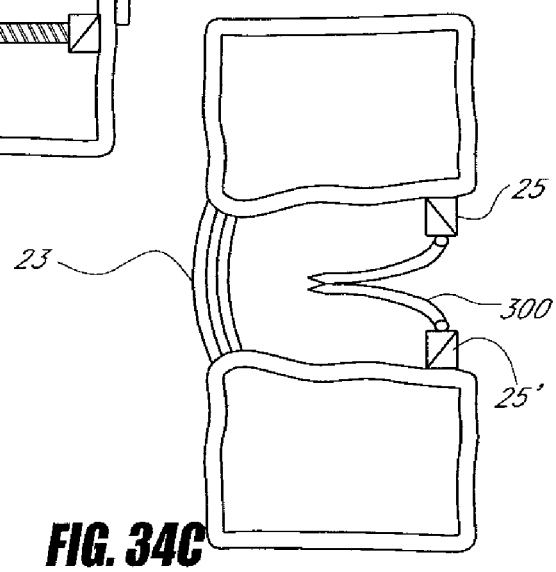

FIGS. 34A-34C illustrate additional embodiments of a support assembly 300 and various embodiments of implantation location. For example, FIG. 34A illustrates a support assembly 300 with a first anchor 25 attached generally at a lower anterior region of a superior vertebral body 31 and a second anchor 25' attached at an upper anterior corner of a inferior vertebral body 32. FIG. 34A illustrates an embodiment of the support assembly 300 implanted in a defect located generally at an anterior position and opposite intact anulus tissue 23. FIG. 34B illustrates another embodiment of support assembly 300 where the anchors 25 are configured generally as threaded or screw shaped structures. In this embodiment, the anchors 25 are positioned generally at an anterior outer surface of superior and inferior vertebral bodies 31, 32 In this embodiment, the opposed gate members 302 further extend from an interstitial region between the vertebral bodies 31, 32 outwards towards the respective anterior surfaces of the vertebral bodies 31, 32 for connection with the respective anchors 25. FIG. 34C illustrates a further embodiment where the support assembly 300 is implanted at opposed inner surfaces of a superior and inferior vertebral body 31, 32 along the endplates and within or beyond the anulus. The support assembly 300 may arranged at an posterior, anterior, or lateral position of the vertebral bodies 31, 32.

Figure 35A:
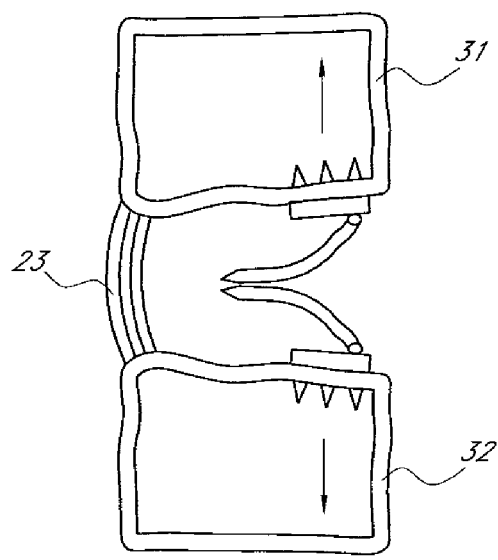
FIGS. 35A and 35B illustrate two embodiments of anchors and attached gate members and corresponding implantation configurations.
Figure 35B:
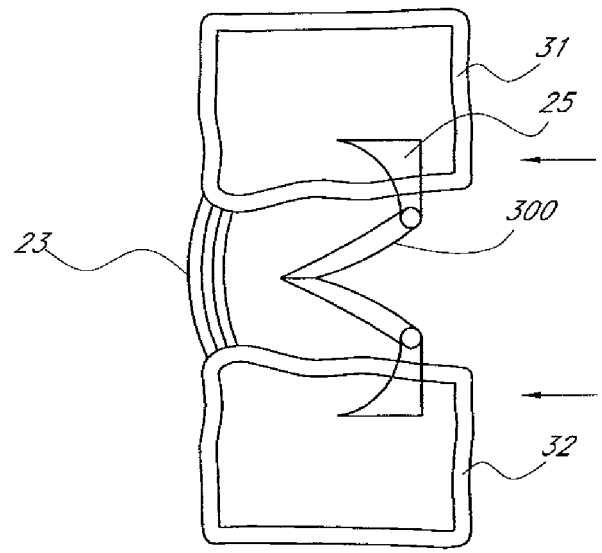

FIGS. 35A and 35B illustrate further embodiments of a support assembly 300 and various embodiments of anchor 25 configurations. FIG. 35A illustrates that the anchors 25 comprise a generally spiked or barbed plate profile configured to be driven into and attached to respective vertebral bodies 31, 32. FIG. 35A further illustrates that the opposed anchors 25 are presented to the patient tissue in a generally vertical anti-parallel approach. FIG. 35B illustrates an embodiment where the anchors 25 comprise a generally T-shaped or keel profile. FIG. 35B further illustrates an embodiment wherein the opposed anchors 25 are presented to the respective vertebral bodies 31, 32 in a generally parallel transverse approach.

FIGS. 36A-36C illustrate top views of embodiments of support assembly 300 and respective implantation locations with respect to patient tissue, such as an anulus 23. FIG. 36A illustrates that an anchor 25 can be implanted in a defect region 33 such that the anchor 25 is interposed between an inner surface 26 and an outer surface 27 of the anulus 23. FIG. 36B illustrates an embodiment where the anchor 25 is implanted substantially adjacent or flush with an outer surface 27 of the anulus 23. FIG. 36C illustrates an embodiment where the anchor 25 is implanted substantially adjacent with an inner surface 26 of the anulus 23.

FIG. 37 illustrates a further embodiment of support assembly 300 comprising a plurality of interleaved leaves or fingers 304. In some embodiments, the individual leaves or fingers 304 are generally aligned with other leaves or fingers 304 and in other embodiments the multiple leaves or fingers 304 are not generally aligned with each other.

Figure 38A:
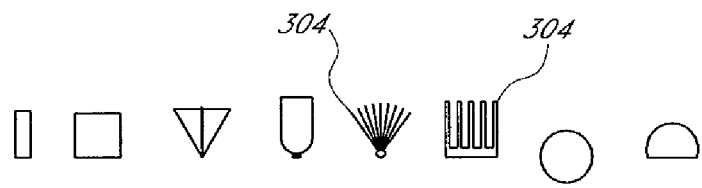
FIGS. 38A and 38B illustrate top and side schematic views respectively of various shapes and configurations of gate members.
Figure 38B:
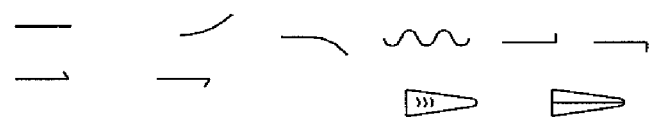

FIGS. 38A and 38B illustrate top and side views respectively of various configurations of gate member 302. As illustrated, a gate member 302 can define a generally non-square rectangular, a generally square, a triangular, a semi-circular, a circular, or an irregular profile. In some embodiments, a gate member 302 comprises a plurality of leaves or fingers 304 arranged to extend in divergent directions so as to describe a brush-like configuration. In some embodiments, a gate member 302 can comprise a plurality of leaves or fingers 304 extending generally parallel to each other so as to define a finger-like profile. Other shapes and profiles of gate member 302 are possible. FIG. 38B illustrates that gate members 302 can define a generally straight profile, an upwardly curved, a downwardly curved, a serpentine or undulating curve, an upward angled bend, a downward angled bend, angled bends of approximately zero to ninety degrees, angled bends of approximately 90 degrees, angled bends of approximately ninety to one hundred eighty degrees, concave, convex, and/or multifaceted profiles.

Figure 39A:
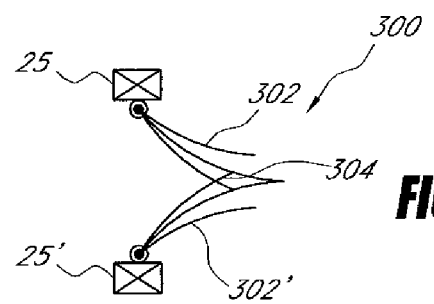
FIG. 39A illustrates an embodiment of multiple anchors and attached respective gate members where the gate members are interweaved but not aligned with each other.
Figure 39B:
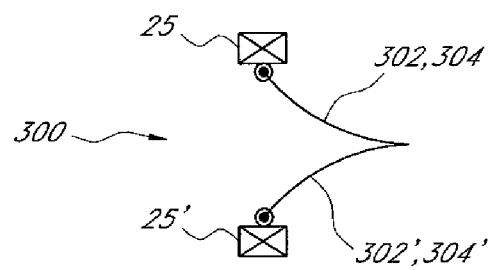
FIG. 39B illustrates an embodiment of multiple anchors and connected respective gate members wherein the gate members associated with a respective anchor are substantially aligned with each other.

FIG. 39A illustrates an embodiment of support assembly 300 comprising opposed gate members 302, 302' each having a plurality of interleaved leaves or fingers 304. In this embodiment, the individual leaves or fingers 304 of each gate member 302 extend along different paths as seen in side view or are not generally aligned with each other. FIG. 39B illustrates an embodiment of support assembly 300 having opposed gate members 302, 302' each having a plurality of individual leaves or fingers 304. In this embodiment, the individual leaves or fingers 304 of each gate member 302 are generally aligned with each other as seen in side view.

FIG. 38C illustrates further embodiments of gate members 302 including a concave multifaceted three dimensional profile, a concave generally smooth monotonic profile, and a profile combining both generally smooth curved portions and generally flat or flange contours.

FIGS. 40A and 40B illustrate embodiments of support assemblies 300 comprising opposed gate members 302 having a concave profile. In one embodiment as illustrated in FIG. 40A, opposed gate members 302, 302' are substantially mirror images of each other having similar shapes, sizes and contours. The opposed gate members 302, 302' are further aligned so as to engage with each other to form a substantially continuous occlusion or seal aspect of the support assembly 300. FIG. 40B illustrates another embodiment where the opposed gate members 302, 302' are similar in shape and contour, however can have different sizes. In the embodiment illustrated in FIG. 40B, the opposed gate members 302, 302' are configured and arranged to engage with each other in a nested configuration.

FIG. 41 illustrates a further embodiment of support assembly that can be similar to any previously described embodiment of support assembly 300. In the embodiment illustrated in FIG. 41, a connector 306 is provided to clamp, connect or provide a pivotal axis between the opposed gate members 302. The connector 306 can be provided in alternative or in combination with a resilient or self-engaging aspect of the gate members 302 to provide additional resistance to separation of the opposed gate members 302. The embodiment illustrated in FIG. 41 can be preferred in implementations where the sealing or blocking function provided by the support assembly 300 is preferably provided in a bi-directional manner.

Threaded Keel Anchor

FIGS. 42A and 42B illustrate in side and end views respectively embodiments of a first anchor structure 310 and a second anchor structure 312. The first and second anchor structures 310, 312 can be secured or connected to each other, for example via a fastener 314. The first anchor structure comprises a first threaded profile 316 configured to allow the first anchor structure 310 to threadably engage with patient tissue in a well known manner. The first anchor structure 310 further comprises a second threaded profile configured to threadably engage with the fastener 314.

The second anchor structure 312 comprises an attachment structure 322 that can be configured as an attachment point for sutures and/or for connection to a separate implant (not illustrated). The second anchor structure 312 also comprises a foot or keel structure 324. The foot or keel structure 324 is configured to secure and align the second anchor structure 312 for connection with the first anchor structure 310. The foot or keel portion 324 can be further configured to engage with patient tissue to secure the second anchor structure 312 thereto.

FIGS. 43A-43D illustrate embodiments of an implantation and attachment process for the first and second anchor structures 310, 312. As illustrated in FIG. 43A, a pilot hole can be formed in patient tissue, for example comprising an anulus. As shown in FIG. 43B, the first anchor structure 310 can be threadably inserted into the pilot hole via a combination of rotational and/or translational forces. As illustrated in FIG. 43C, the second anchor structure 312 can then be laterally driven into the patient tissue and into engagement with the first anchor structure 310, for example into the second threaded profile 320. FIG. 43D illustrates in end view that the fastener 314 can be threadably engaged with the second threaded profile 320 of the first anchor structure 310 to secure and connect the second anchor structure 312 in position.

FIGS. 44A and 44B illustrates another embodiment of a first anchor structure 330 and a second anchor structure 332. The first anchor structure 330 comprises a first engagement surface 334 configured and sized to engage with a cooperating second engagement surface 336 of the second anchor structure 332. The first anchor structure may be a screw. The second anchor structure may be a keel terminating in a collar or other such engagement surface. The second anchor structure may have a void or hole that facilitates coupling to an implant (e.g., a barrier).

FIGS. 45A-45C illustrate embodiments of introduction processes for securing the first and second anchor structures 330, 332 to each other and to patient tissue. As illustrated in FIG. 45A, an opening or pilot hole 342 can be formed in patient tissue (e.g., vertebral body) 340. FIG. 45B illustrates that the second anchor structure 332 is introduced into the desired location in the patient tissue 340 via a generally linear translational introduction. However, it should be noted that the opening 342 need not be formed prior to introduction of the second anchor structure 332. For example, the second anchor structure 332 can be introduced to the patient tissue 340 before formation of the opening 342. Formation of the opening 342 is optional and may be omitted. For example, depending on the relative size of the first anchor structure 330 and the characteristics of the patient tissue 340, the first anchor structure 330 can comprise a self-drilling aspect reducing or eliminating the need to form the opening 342. FIG. 45C illustrates a further process wherein the first anchor structure 330 is threaded into the patient tissue 340 and further so as to engage the first and second engagement surfaces 334, 336. Thus, the second anchor structure 332 is secured and positioned both by its contact with the patient tissue 340 and via connection with the first anchor structure 330 which is also engaged with the patient tissue 340.

FIGS. 46A and 46B illustrate in perspective and side views respectively embodiments of a support implant 350 configured for closing, blocking, reinforcing, and/or repairing defects, openings, or weakened areas in a variety of patient tissues. In some embodiments, the support implant 350 is particularly adapted for use in the intervertebral disc region, such as for reinforcing a weakened anulus and/or for closing defects. The support implant can inhibit herniation of disc material or augmentation implants outside the anulus or into defects in the anulus. Embodiments of the support implant 350 provide these benefits while limiting interference with spinal joint movement including flexion, extension, and lateral bending movement.

The support implant 350 comprises an anchor 25 that can be formed according to any of the previously described embodiments of anchor 25. In one embodiment, the anchor 25 describes a generally T-shaped profile having two keel portions extending generally at right angles to each other. The anchor 25 can include solid features, roughness features, leading edges, or any other combination of features and profiles as described herein.

The support implant 350 further comprises a support structure 352. The support structure 352 can comprise one or more of meshes, grafts, patches, gates, membranes, stents, plugs, frames, and the like, suitable for augmenting, fortifying, bulking, closing, blocking, occluding, and/or delivering one or more therapeutic and diagnostic agents to weakened or damaged tissues. The support structure 352 can be expandable, can be concave or convex along one or multiple axes, oversized with respect to a defect region, correspond generally to the size of the defect region, or be sized to cover all or a portion of a region of intact tissue.

FIGS. 47A and 47B illustrate an anterior-posterior view and a lateral view respectively of embodiments of support implant 350. FIGS. 47A and 47B are further presented as radiographic images, for example as may be obtained via radiographic imaging of the support implant 350 in an implanted location. As seen in FIGS. 47A and 47B, the support implant 350 comprises a first marker 354*a* and a second marker 354*b*. The markers 354*a*, 354*b* can comprise iridium, platinum, platinum-iridium alloys, or other materials configured to provide an enhanced in vivo image, for example as may be obtained with radiographic imaging. It will be appreciated that some embodiments of the support structure 352 can comprise biocompatible materials which can be difficult to image in the implantation environment. The markers 354 provide an enhanced ability to image the support implant 350 and thereby determine the location and orientation of components of the support implant 350 that may be otherwise difficult to determine.

FIG. 48 and Detail A thereof provide a schematic side view illustration of embodiments of a support implant 350 comprising a moveable support structure 352. In one embodiment, the support implant 350 comprises a moveable joint 356 between the support structure 352 and an anchor 25. In some embodiments, the moveable joint 356 defines a pivotable or hinged connection between the support structure 352 and the anchor 25. In one embodiment, the support implant 350 further defines first and second stop structures 360*a* and 360*b* configured to limit the range of motion of the support structure 352. In some embodiments, the support structure 352 is resiliently biased for movement in a desired direction.

Figure 49:
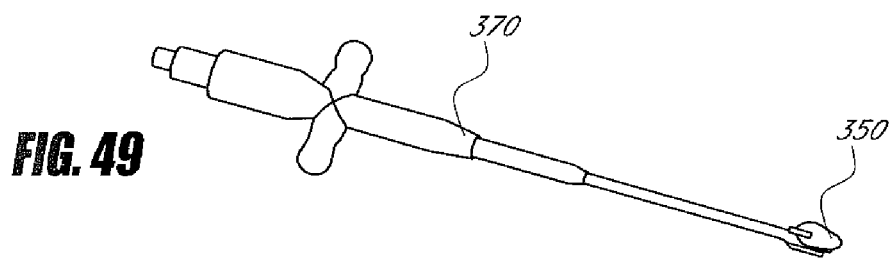
FIG. 49 illustrates an embodiment of a delivery tool configured to facilitate the implantation of embodiments of support implants.

FIG. 49 illustrates an embodiment of a delivery tool 370 configured to hold and deliver embodiments of support implants 350. Structure and operation of the delivery tool 370 will be described in greater detail with respect to FIGS. 50A-50E and 51 which illustrate a deployment sequence employing the support implant 350 and delivery tool 370.

Figure 50A:
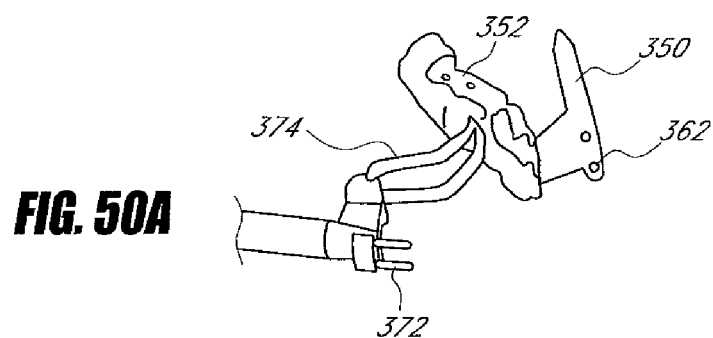

As shown in FIG. 50A, a distal end of the delivery tool 370 comprises first guide structure 372. The first guide structure 372 is configured to engage with corresponding guide structures 362 of the support implant 350. The first guide structure 372 can be configured as one or more of pins, posts, slots, grooves, dovetails, or other structures configured to maintain an alignment and orientation between the delivery tool 370 and the support implant 350. In some embodiments, the first guide structure 372 engages with guide structures 362 formed in the anchor 25.

Figure 50B:
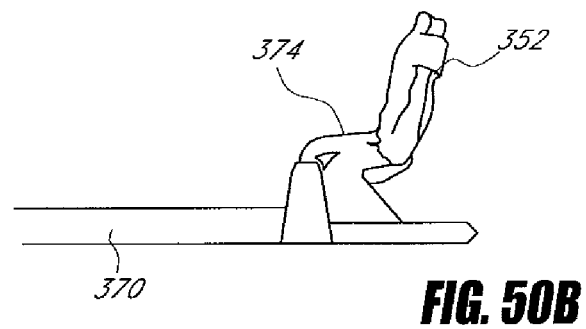

The delivery tool 370 further comprises second guide structures 374. The second guide structures 374 are configured to engage with the support structure 352 and maintain the support structure 352 at a desired orientation and position with respect to the anchor 25. For example, FIG. 50B illustrates the support implant 350 engaged with both the first and second guide structures 372 and 374.

FIGS. 50C, 50D, and 50E illustrate a progression of the support implant 350 engaging with the delivery tool 370. An end plate guide of the delivery tool 370 advances towards the support implant 350 and urges the second guide structures 374 to induce the support structure 352 into adjacency with the anchor 25. The adjacency of the support structure 352 to the anchor 25 provides a reduced cross-sectional profile, for example as illustrated in FIG. 50E, to facilitate introduction of the support implant 350 to the desired implant location.

FIG. 51 illustrates the support implant 350 and engaged delivery tool 370 at an implant location. In this embodiment, the implant location comprises a corner of patient tissue 340, such as a vertebral body 31, 32. The support implant 350 and delivery tool 370 define in one embodiment a pair of adjacent first and second locating surfaces 380, 382. The first and second locating surfaces 380, 382 can be positioned to contact the patient tissue 340 to inhibit further movement of the support implant 350 or delivery tool 370 in multiple dimensions.

Figure 52A:
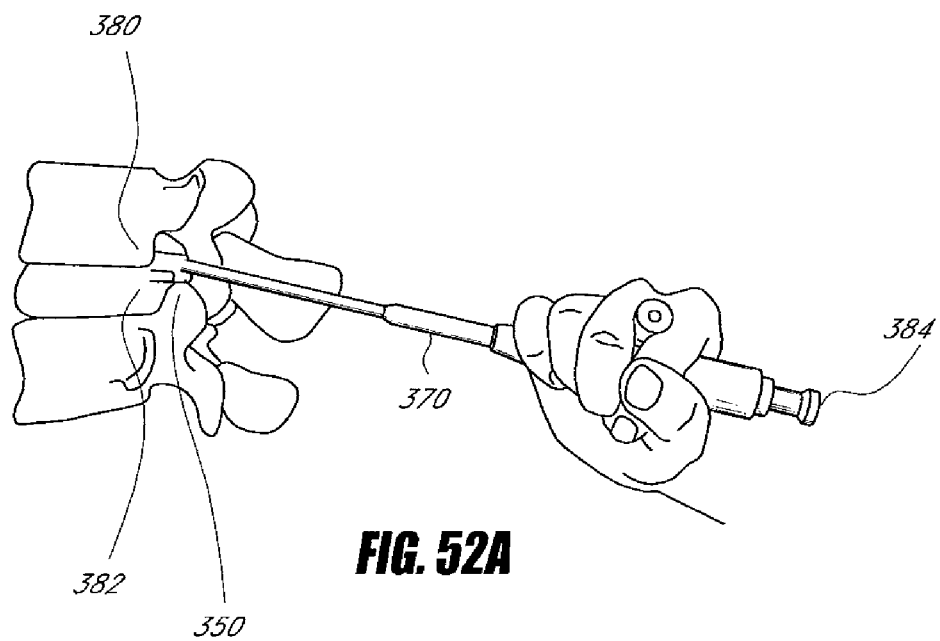
FIGS. 52A-52E illustrate a plurality of configurations of a support implant deployed at various implantation locations.
Figure 52B:
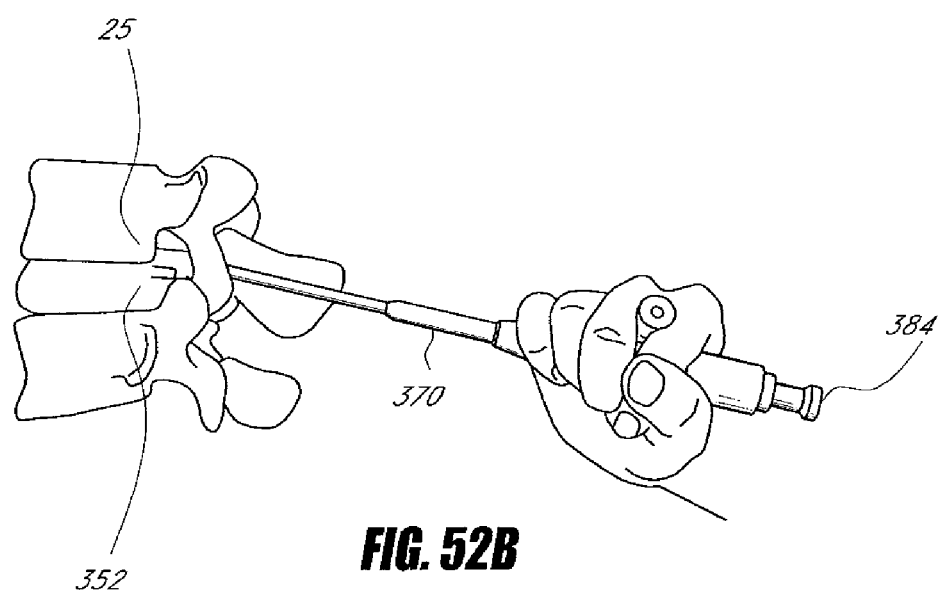

As illustrated in FIGS. 52A and 52B, force can be applied, for example at a driving surface 384 of the delivery tool 370 to urge the anchor 25 into anchoring tissue. The delivery tool 370 can then be withdrawn thereby releasing engagement between the first guide structure 372 and the anchor and the second guide structure 374 and the support structure 352. The support structure 352 is then released to expand or move into a desired deployed location.

Figure 52C:
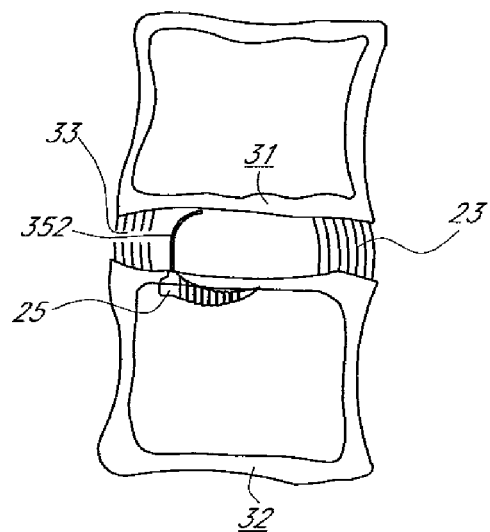
Figure 52D:
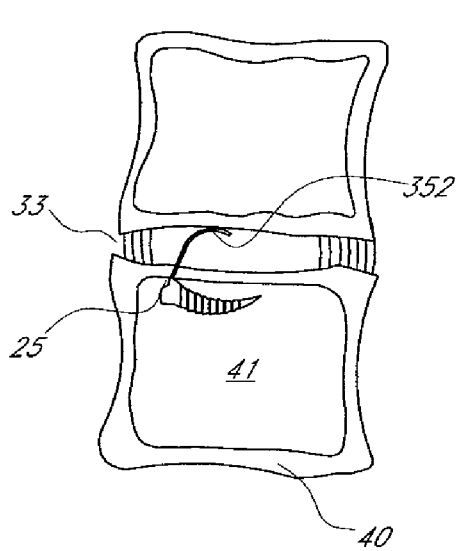
Figure 52E:
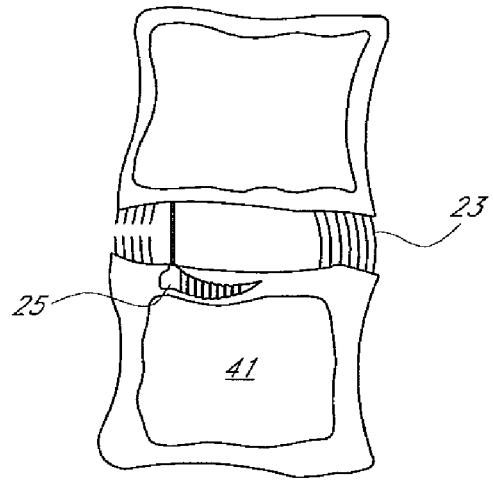

FIGS. 52C-52E illustrate a variety of embodiments of deployment positions for the support implant 350. FIG. 52C illustrates that the anchor 25 is driven to extend substantially within cortical bone 40 but also to extend along an interface between the cortical bone 40 and adjacent cancellous bone 41. FIG. 52C further illustrates that the moveable support structure 352 extends to obstruct or occlude a defect 33 in the anulus 23. Movement of the moveable support structure 352 can be inhibited by one or more stop structures 360 as previously described and/or via interference with adjacent patient tissue, for example a superior vertebral body 31. Support structure 352 can extend proximally from the anchor 25 at roughly perpendicular to the endplate in which the anchor 25 is implanted and then extend distally at an angle roughly parallel to the opposing endplate.

FIG. 52D illustrates an embodiment where the anchor 25 is driven into position to anchor in both cortical bone 40 and cancellous bone 41. FIG. 52E illustrates an embodiment where the anchor 25 is driven to secure substantially solely to cortical bone 40 with little to no contact with cancellous bone 41. FIG. 52E further illustrates the anchor 25 deployed at a more medial location as compared to the more posterior locations of anchor 25 illustrated in FIGS. 52C and 52D.

Figure 53A:
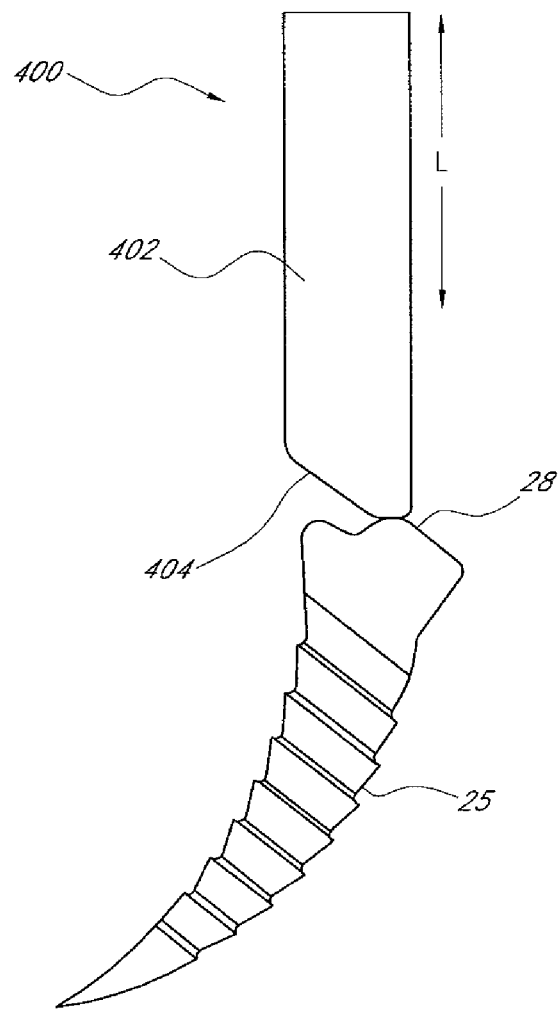
FIGS. 53A-53C illustrate an embodiment of an implantation process and cooperating anchor and delivery tool.
Figure 53B:
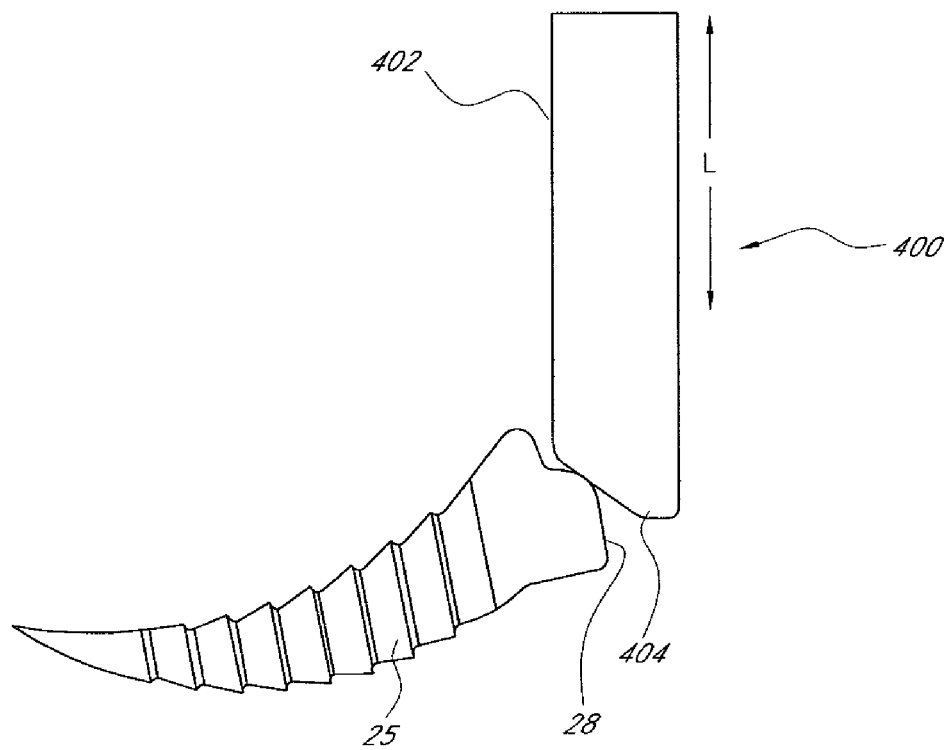
Figure 53C:
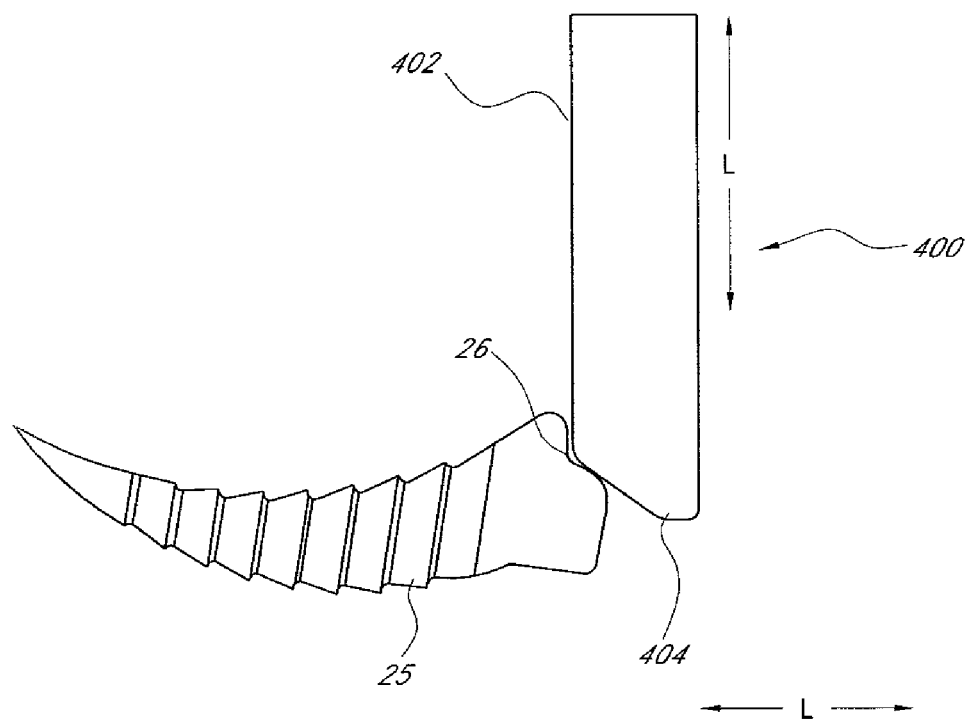

With reference to the curvilinear anchors and delivery devices depicted inter alia in FIGS. 2-4, FIGS. 53A-53C illustrate an embodiment of a delivery tool 400 adapted to drive one or more anchors into a desired implantation or anchor location in patient tissue (patient tissue not illustrated). FIGS. 53A-53C also illustrate embodiments of a deployment sequence employing the delivery tool 400 and anchor 25.

As illustrated in FIG. 53A, the delivery tool 400 comprises an urging member 402. The urging member 402 is configured to apply a translational force to the anchor 25. The urging member 402 can provide force to the anchor 25 arising from impact force, hydraulic pressure, pneumatic pressure, electromagnetic force, threaded motion, and the like.

The urging member 402 defines an engagement profile 404 at a distal or driving end of the urging member 402. The engagement profile 404 can comprise one or more beveled or curved profiles configured to engage with cooperating engagement profile 28 of the anchor 25.

FIG. 53 illustrates an initial or first contact position between the urging member 402 and the anchor 25 and respective engagement profiles 404, 28. As illustrated in FIG. 53A, the anchor 25 initially translates substantially along a longitudinal axis L upon initial contact with patient tissue. However, contact between the beveled or curved engagement profiles 404, 28 and curvature of the anchor 25 result in a camming action inducing the anchor 25 to rotate or curve towards a transverse axis T during the progressive introduction of the anchor 25 into patient tissue. In the views provided in FIGS. 53A-53C, the anchor 25 rotates by approximately ninety degrees in a clockwise direction. As shown in FIG. 53C, during final stages of introduction of the anchor 25 into patient tissue, the anchor 25 expands substantially along the transverse axis T with significantly reduced relative motion along the longitudinal axis L of movement of the urging member 402.

FIGS. 53A-53C further illustrate a progressive camming or sliding movement between the opposed engagement profiles 404 and 28. The particular profiles or contours illustrated in FIGS. 53A-53C are simply illustrative of one example and a variety of curves and profiles can be provided in various embodiments of the delivery tool 400 and anchor 25 depending on the needs of a particular application and the characteristics of the target patient tissue.

Figure 54A:
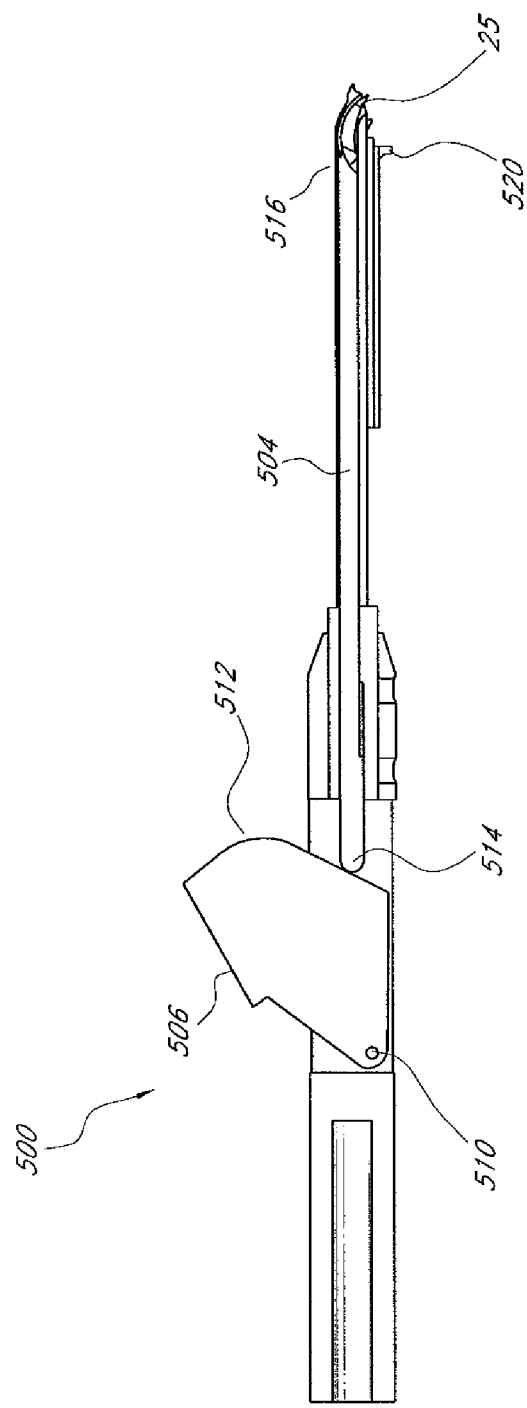
FIGS. 54A-54C illustrate another embodiment of a delivery tool and embodiments of operation of the tool at various stages of an implantation procedure.
Figure 54B:
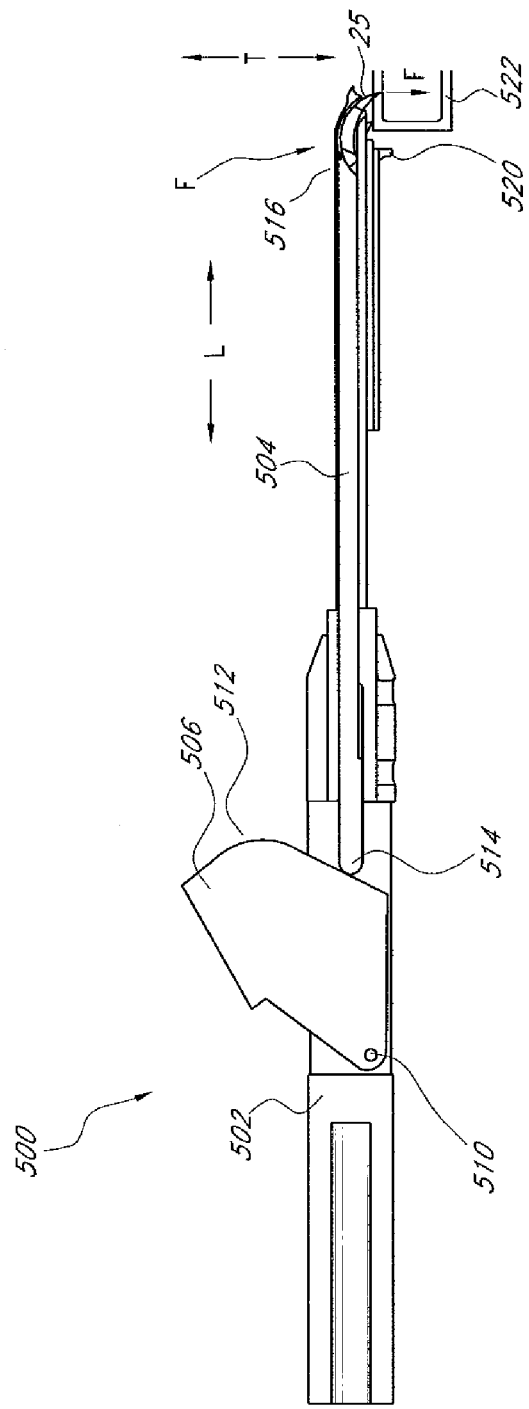
Figure 54C:
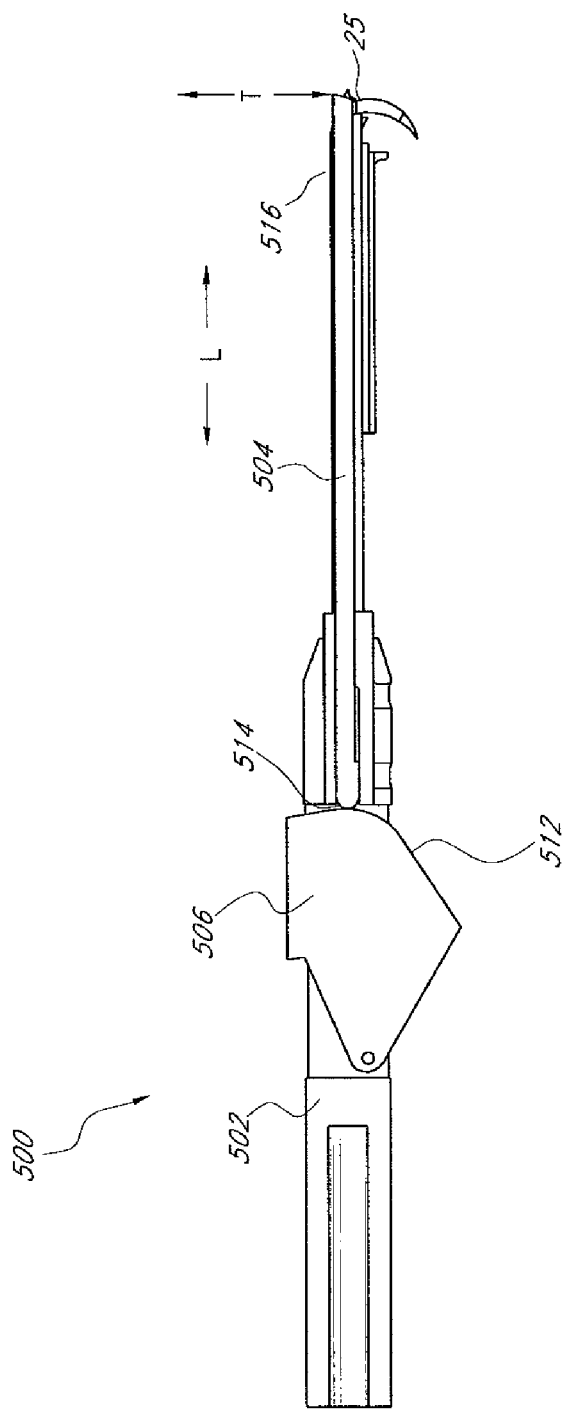

FIGS. 54A-54C illustrate another embodiment of a delivery tool 500 and sequence of operation of the delivery tool 500 in advancing an anchor 25 into a desired location in target tissue 522. The delivery tool 500 comprises a guide body 502. The guide body 502 is configured to provide a user a grasping surface for manipulating and holding the delivery tool 500. The delivery tool 500 further comprises an urging member 504 to transmit force from the delivery tool 500 to one or more anchors 25.

The delivery tool 500 further comprises a drive member 506. The drive member 506 is attached via a hinged connection 510 to the guide body 502. The hinged connection 510 can comprise one or more of a pivot, pin, axle, hinge, bearings, bushings, and the like. The hinged connection 510 provides pivoting or hinged movement between the drive member 506 and the guide body 502.

The delivery tool 500 further comprises a first cam surface 512 arranged generally at a forward surface of the drive member 506. The first cam surface 512 engages with a cooperating second cam surface 514 provided at a proximal end of the urging member 504. The first and second cam surfaces 512, 514 cooperate such that hinged or pivoting movement of the drive member 506 induces a sliding relative motion between the first and second cam surfaces 512, 514 to urge or advance the urging member 504 outwards. In various embodiments, one or both of the first and second cam surfaces 512, 514 can include substantially flat surfaces and curved surfaces. The curved surfaces can describe varying radii of curvature along different portions of the first and/or second cam surfaces 512, 514.

The delivery tool 500 also comprises a depth stop 520 that in some embodiments is adjustable in position or location. As illustrated in FIG. 54B, the depth stop 520 provides a blocking or locating function with respect to the target tissue 522 inhibiting undesired relative motion between the delivery tool 500 and the target tissue 522.

FIG. 54B further illustrates a generally transversely oriented force applied to the drive member 506 indicated by the designator $F_1$ and arrow directed generally inwardly towards the delivery tool 500 along a substantially transverse axis T where the delivery tool 500 extends substantially along a longitudinal axis L. In use, a user would hold the delivery tool 500 in a desired position, for example by grasping the guide body 502. As the user holds the delivery tool 500 in the desired location, the generally transversely directed force $F_1$ applied to the drive member 506 is coupled to the distal end of the delivery tool 500 to a second generally transverse force $F_2$ directed towards the target tissue 522. In this embodiment, the delivery tool 500 acts as a third class lever to transmit force applied to the drive member $F_1$ as a similarly directed force $F_2$ at the distal end of the delivery tool 500.

As previously noted, in some embodiments, for example as illustrated and described with respect to FIGS. 53A-53C, an anchor 25 can curve or rotate during an introduction procedure to transition from a generally longitudinal approach through a transition into a substantially transverse approach. As the anchor 25 begins and continues transverse motion into the target tissue 522, a reaction or recoil force $F_3$ is generated tending to drive the distal end of the delivery tool 500 and the attached anchor 25 away from the target tissue 522. As the force $F_2$ at the distal end of the delivery tool 500 is opposite to the reaction or recoil force $F_3$, these forces will tend to counteract each other helping to maintain the distal end of the delivery tool 500 at the desired location and facilitating more accurate and easier introduction of the anchor 25 into the target tissue 522.

As previously noted, engagement profiles 404 and 28 can be provided on the distal end of the urging member 504 and the anchor 25 respectively to facilitate the transition of advancement of the anchor 25 from generally longitudinal motion transitioning to generally transverse motion. The contour and relative position of the engagement profiles 404 and 28 can be adapted for more efficient transmission of force particularly through the transition from generally longitudinal to generally transverse movement while maintaining the delivery tool 500 in substantially the same position and orientation.

FIG. 54C illustrates an embodiment of the delivery tool 500 and engaged anchor 25 at a generally terminal step in an advancement procedure of the anchor 25. It can be seen that the anchor 25 in this embodiment extends substantially in a transverse direction. FIG. 54C illustrates further advantages of the delivery tool 500 in providing a self-limiting function. The engagement between the drive member 506 and the guide body 502 via the hinged connection can be configured such that motion of the drive member 506 is limited with respect to the guide body 502. The dimensions and contours of the urging member 504 and drive member 506 and the first and second cam surfaces 512 and 514 can preferably be selected such that the inward movement limit of the drive member 506 corresponds to a desired limit of advancement of the anchor 25 with respect to the distal end of the delivery tool 500. This provides the advantage of automatically limiting the extent of protrusion of the urging member 504 and can provide more repeatable advancement of the anchor 25 to a desired implantation depth and along a desired introduction path.

Figure 55A:
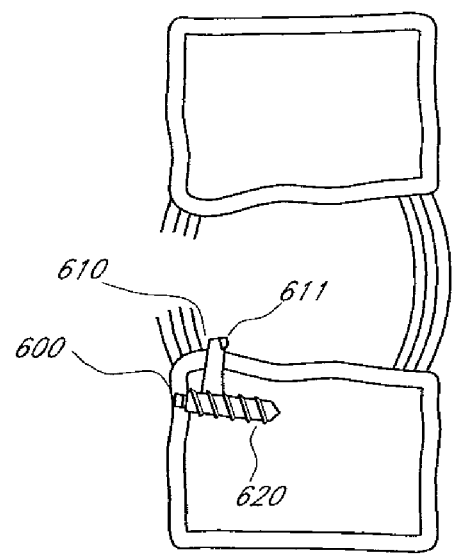

FIG. 55A illustrates an embodiment of anchor 600 comprising a neck/keel portion 610 and a screw portion 620 that is implanted along the axis of an anulotomy and disc access, just below or above the disc space into an adjacent vertebral body. The neck/keel portion 610 can be independently rotatable so as to extend from the screw portion 620 toward the disc space, providing an anchoring platform and site 611 from which to attach sutures, graft containment devices, and/or other medical devices. The screw portion 620 has an outer or major diameter that includes the threads. The base of the threads defines an inner diameter or minor diameter that forms an axle or rod to support the threads. In FIG. 55B the anchor 600 is illustrated including the distal tip 613 of the screw portion 620 which can be drill-tipped (for self drilling anchors), or blunt or cone shaped for anchors that are pre-drilled in a previous step in the procedure.

In various embodiments one or more lateral projections in the form of neck, keel, fin, or plate can be mounted along the length of a screw or proximal to either end thereof. The attachment of the keel 610 to the screw portion 620 may provide for substantially free and independent rotation of the screw portion 620 without imparting a significant rotational force upon the keel 610. Alternatively the keel 610 can be connected or attached to the screw portion 620 such that it is inhibited from rotation before and/or after the screw portion 620 has been implanted.

Figure 56A:
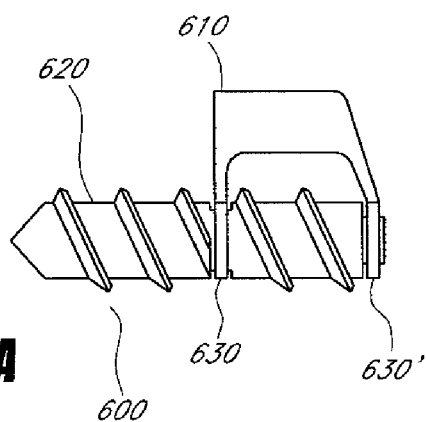
FIGS. 56A and 56B illustrate embodiments of an implantable support anchor in side view and end view respectively.
Figure 56B:
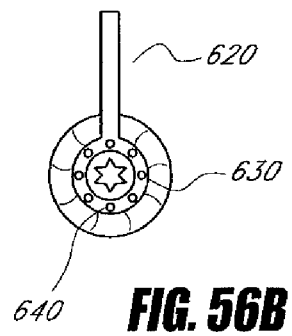
Figure 56C:
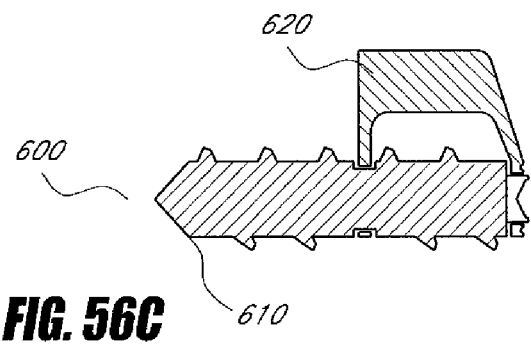
FIGS. 56C and 56D illustrate the embodiments of an implantable support anchor of FIGS. 55A and 55B and an embodiment of driver adapted for use therewith.

In one or more of the embodiments the keel 610 can be aligned in a desired direction such as vertically, e.g. extending away from the vertebral endplate and into the disc space. The keel 610 can be attached to the screw portion 620 in a number of ways. FIGS. 56A-C illustrate various views of a screw and keel anchor assembly 600. In FIG. 56A, the keel 610 forms a ring 630 at two locations, both with outer diameters equal to or less than the screw's minor diameter, and generally encircling the screw's axle at a region where there are no threads and a reduced axle diameter. The screw portion 620 "captures" the keel's 610 ring 630 or rings and allows the screw to spin freely about the keel 610.

Figure 56D:
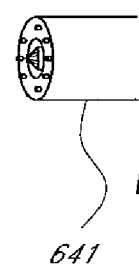

The most proximal end of the proximal ring 630' of the keel 610 as illustrated in FIG. 56B may also include one or more features 640 that allow a driver to restrain rotation and align the keel 620 in the desired direction. In the illustration this is a series of small holes in the keel ring 630 and small pins in a corresponding driver 641 (FIG. 56C). FIG. 56C illustrates the anchor 600 and one embodiment of driver 641 (FIG. 56D). The driver 641 also may have a shoulder (not illustrated) that rests on the bone when the bone anchor is fully advanced that inhibits advancing the screw 620 beyond a desired depth.

In certain other embodiments, there may be more than one neck, keel, fin, plate, or projection, joined together or independently to the screw, in one or more directions. The keel may be bifurcated, form a ring or loop and/or comprise a neck and a bridge attachment site. FIG. 57A illustrates an embodiment of the anchor device 600 in which there is neck portion defining an attachment site 611 and a bifurcated keel 610 and 610'. In this embodiment the keels and neck portion are mounted at the distal tip 613 of the screw. The screw portion 620 can be concentric or offset off axis about which the one or more keels extend. FIG. 57B is substantially similar to the embodiment illustrated in FIG. 57A except that the attachment site 611 and keels 610, 610' are mounted at the proximal end of the screw portion 620 of the anchor 600.

Figure 57C:
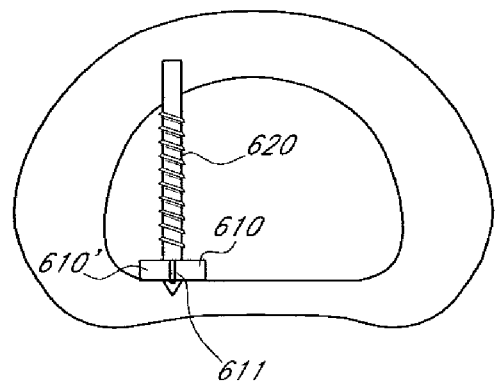
FIGS. 57C and 57D illustrate schematic side views of the embodiments illustrated by FIGS. 57A and 57B in an implanted position.
Figure 57D:
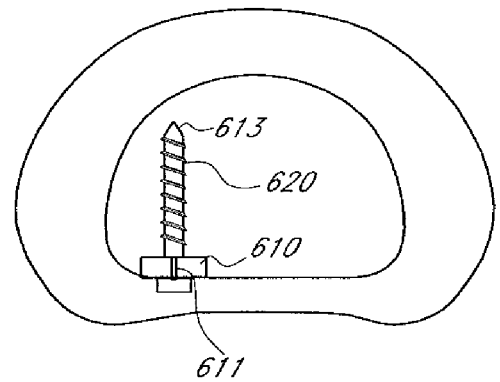

FIG. 57C illustrates embodiments of implants similar to the implant illustrated in FIG. 57A in an implanted orientation within an intervertebral disc. In this case the implant was delivered from an anterior surgical approach and the keel 610 and attachment site 611 of the implant are situated at the posterior lateral portion of the endplate. Turning to FIG. 57D, an implant similar to the implant illustrated in FIG. 57B is provided and has been delivered via a posterior lateral surgical approach.

Further embodiments can include the addition of features to control the alignment and depth of an anchor, in relation to the surgical access and desired final implantation location of either the keel, the screw, or both. Besides the use of stops for depth control, an indicator and/or the use of X-ray imaging to visualize screw depth, an alignment pin oriented along the end of the keel parallel to the axis of the screw can facilitate visual or physical alignment of the screw and keel toward the desired location. Various lengths of screws and length and depth of keels, relative to the countersunk bony surface, can provide a range of options in terms of patient anatomy to properly place the strongest and most convenient anchor and neck keel platform.

In other embodiments, the keel itself need not extend perpendicular from the screw's longitudinal axis, but can be jogged to one or more sides of the screw, and/or angled toward or away from the distal end of the screw as needed to accommodate target anatomy. In some embodiments, the keel or lateral projection can be mounted or coupled at or along a medial portion of the screw, at a distal end, at a proximal end, or anywhere else along its length.

Various embodiments of keel/screw anchor device described herein can also be adapted to resist back-out or unscrewing or other undesired movement after implantation by the addition of a locking or engaging feature. For example, once implanted to a desired depth with the bone, the keel, fin, plate, and/or projection locks or engages the screw. In this position the screw is inhibited from rotating because the torque and/or translation force acting on the keel is resisted by the shear force of the bone.

Delivery methods described herein may alternatively or in addition include the delivery of bone cement or any suitable adhesive within, though, or adjacent the implant. The step of delivering bone cement such as polymethylmetacrylate (PMM) can also be used to fill in the area left by a countersunk anchor to aid to prevent further fracture, back-out of the screw or keel and to aid in healing if the cement is admixed with prophylactic antibiotics other agents.

In some embodiments, anchors can be driven at trajectories other than parallel to an endplate ranging from 1-360 and preferably 10-80 degrees. FIG. 58A illustrates an embodiment wherein a screw and keel type anchor 600 is implanted in an inferior endplate at about 45 degrees relative to the endplate. In FIG. 58B two anchors 700, 700' with a neck and keel are implanted in the inferior and superior endplates of a vertebral body. In this embodiment, the anchors 700, 700' are implanted at angles of approximately 10-25 degrees.

The anchors depicted in FIGS. 58A-B (and the other anchors throughout the disclosure) can be implanted flush to the vertebral body or endplate or countersunk. In other embodiments, anchors are driven at or proximal to the intersection or edge of a vertebral body endplate and vertebral body outer surface.

Figure 59A:
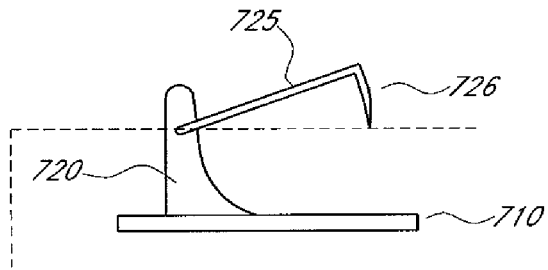
FIGS. 59A and 59B illustrate side views of embodiments of implantable support anchor having a movable arm.
Figure 59B:
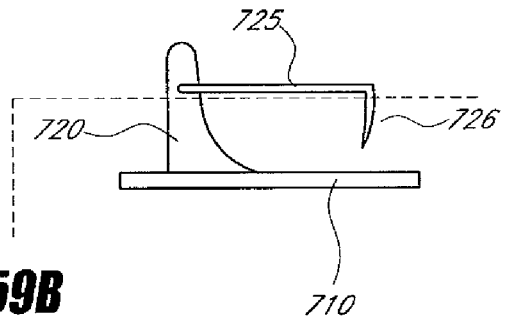
Figure 59C:
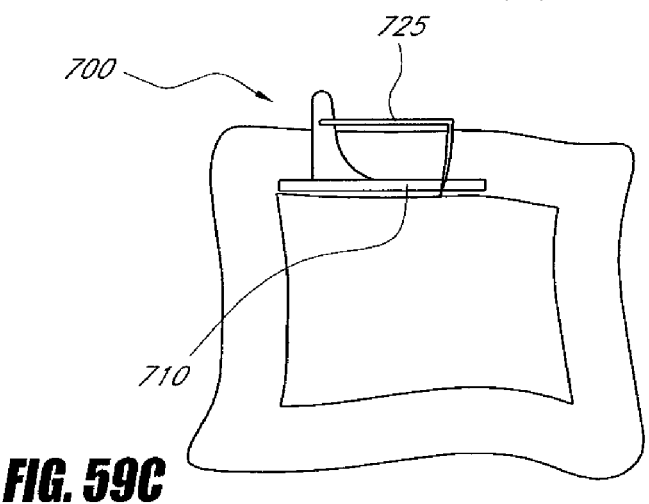
FIG. 59C illustrates a schematic side view of the embodiments illustrated by FIGS. 59A and 59B in an implanted position.
Figure 59D:
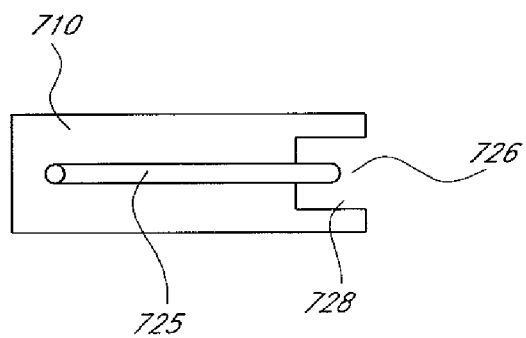
FIG. 59D is a top view of the embodiments illustrated by FIGS. 59A and 59B.

FIGS. 59A-D illustrate an embodiment involving a locking or back-out feature for an anchor. FIG. 59A is a side view of an anchor having a plate-like lower keel 710 and a neck 720 extending generally perpendicularly therefrom. The neck 720 and keel 710 can further comprise various features described infra. Along the neck 720 is arranged an arm or extension 725 that is rotatably or flexibly engaged to the neck and terminates in one or more barb, hook, or angled projection 726. In other embodiments, the extension 725 is a separate floating member that slides along the neck 720. In use, as illustrated schematically in FIG. 58B, the arm 725 is raised as the neck 720 and keel 710 are driven across and into a bone surface. When the desired implantation side is reached, the arm 726 can be driven downward by striking it along its longitudinal axis and/or released from a flexed raised position such that it rotates downward to engage and at least partially penetrates the bone surface, such as an endplate. The arm 725 can pivot freely or be under tension to compress the bone between the plate and the arm 725. Further embodiments of this locking feature include arm 725 that extends beyond the plate as illustrated in FIG. 59C and a plate 710 with voids or a "U" shaped tip 728 or engagement zone as depicted in FIG. 59D that function to engage or couple the angled projection 726 with the plate 710.

Any of the devices or methods herein may be used to anchor or attach implants, grafts, tendons, patches, orthodontia, sutures, etc. in a variety of orthopedic applications including the knee, shoulder, wrist, cranium, ankle, heel and jaw.

Modifications can be made to the embodiments disclosed herein without departing from the spirit of the present invention. For example, method steps need not be performed in the order set forth herein. Further, one or more elements of any given figure described herein can be used with other figures. The titles and headings used herein should not be used to limit the scope of any embodiments. Features included under one heading may be incorporated into embodiments disclosed under different headings. Therefore, it should be clearly understood that the forms of the present invention are illustrative only and are not intended to limit the scope of the present invention. Further, no disclaimer of subject matter is intended and the scope of the embodiments disclosed herein should be ascertained from a full and fair reading of the claims.

What is claimed is:

1. A method of reconstructing and augmenting a vertebral endplate surface, comprising:

identifying a vertebral body having an outer surface and a vertebral endplate surface adjacent a damaged tissue;

driving first and second anchors into the outer surface of said vertebral body and along and across a cupped cortical rim of said vertebral endplate surface adjacent said damaged tissue;

wherein each of said first and second anchors comprises an upper neck and a lower bone engagement portion;

positioning the lower bone engagement portion below said vertebral endplate surface adjacent said damaged tissue;

recessing the lower bone engagement portion within the outer surface of the vertebral body;

inserting augmentation material along said vertebral endplate surface adjacent said damaged tissue;

wherein the augmentation material comprises a proximal portion and a distal portion;

coupling an attachment site of said upper neck of said first anchor to the proximal portion of the augmentation material; and coupling an attachment site of said upper neck of said second anchor to the distal portion of the augmentation material, thereby reconstructing and augmenting said vertebral endplate.

2. The method of claim 1, further comprising positioning said augmentation material to contact said vertebral endplate surface adjacent said damaged tissue.

3. The method of claim 1, wherein said augmentation material comprises a mesh, scaffold, band or suture.

4. The method of claim 1, wherein said lower bone engagement portion comprises a shaft, prong, plate or keel.

5. The method of claim 1, wherein the first and second anchors are driven into said outer surface and along said vertebral endplate at an angle of about 0 to 90 degrees.

6. The method of claim 1, wherein the first and second anchors are driven into said outer surface and along said vertebral endplate at an angle of about 0 to 20 degrees.

7. The method of claim 1, wherein the step of connecting the attachment sites of said first anchor and said second anchor comprises forming a band around the entire periphery of the endplate.

8. The method of claim 1, wherein said damaged tissue comprises tissue bordering a section of removed tissue.

\* \* \* \* \*